US012692527B2

(12) United States Patent
Muranaka et al.

(10) Patent No.: US 12,692,527 B2
(45) Date of Patent: Jul. 28, 2026

(54) GLUCURONOSYLTRANSFERASE, GENE ENCODING SAME AND METHOD FOR USING THE SAME

(71) Applicants: OSAKA UNIVERSITY, Suita (JP); NATIONAL AGRICULTURE AND FOOD RESEARCH ORGANIZATION, Tsukuba (JP)

(72) Inventors: Toshiya Muranaka, Suita (JP); Hikaru Seki, Suita (JP); Soo Yeon Chung, Suita (JP); Masao Ishimoto, Tsukuba (JP); Susumu Hiraga, Tsukuba (JP); Yukiko Satou, Tsukuba (JP)

(73) Assignees: OSAKA UNIVERSITY, Suita (JP); NATIONAL AGRICULTURE AND FOOD RESEARCH ORGANIZATION, Tsukuba (JP)

( * ) Notice: Subject to any disclaimer, the term of this patent is extended or adjusted under 35 U.S.C. 154(b) by 798 days.

(21) Appl. No.: 17/769,627

(22) PCT Filed: Oct. 16, 2020

(86) PCT No.: PCT/JP2020/039175
§ 371 (c)(1),
(2) Date: Sep. 1, 2022

(87) PCT Pub. No.: WO2021/075572
PCT Pub. Date: Apr. 22, 2021

(65) Prior Publication Data
US 2022/0403437 A1      Dec. 22, 2022

(30) Foreign Application Priority Data

Oct. 17, 2019    (JP) ................................. 2019-190060

(51) Int. Cl.
*C12P 19/56* (2006.01)
*C12N 1/16* (2026.01)
(Continued)

(52) U.S. Cl.
CPC ................ *C12P 19/56* (2013.01); *C12N 1/16* (2013.01); *C12N 9/1051* (2013.01);
(Continued)

(58) Field of Classification Search
None
See application file for complete search history.

(56) References Cited

U.S. PATENT DOCUMENTS

2004/0021072 A1    2/2004   Soudakov et al.
2004/0031072 A1    2/2004   La Rosa et al.
(Continued)

FOREIGN PATENT DOCUMENTS

JP        5526323 B2      6/2014
JP        5771846 B2      9/2015
(Continued)

OTHER PUBLICATIONS

Xie et al. UniProt Database, Acc. No. A0A445KH18, Direct submission, "A reference-grade wild soybean genome." Sep. 2018.*
(Continued)

*Primary Examiner* — Amjad Abraham
*Assistant Examiner* — Dequantarius Javon Speed
(74) *Attorney, Agent, or Firm* — Oblon, McClelland, Maier & Neustadt, L.L.P.

(57) ABSTRACT

Glucuronosyltransferase 1 gene which catalyzes glucuronic acid transfer to the hydroxyl group at the 3-position in an oleanane-type triterpenoid is identified. Glucuronosyltransferase 1 gene having a desired activity, derived from a Fabaceae plant (soybean, *Glycyrrhiza*, and *Lotus japonicus*),
(Continued)

and containing nucleotide sequences represented by SEQ ID Nos: 2, 4, and 6, respectively, is provided.

3 Claims, 18 Drawing Sheets

Specification includes a Sequence Listing.

(51) Int. Cl.
    *C12N 9/10*         (2006.01)
    *C12N 15/81*       (2006.01)

(52) U.S. Cl.
    CPC .... *C12N 15/815* (2013.01); *C12Y 204/01017* (2013.01); *C12N 2800/102* (2013.01)

(56)                References Cited

U.S. PATENT DOCUMENTS

| | | |
|---|---|---|
| 2011/0173724 A1 | 7/2011 | Muranaka et al. |
| 2012/0246760 A1 | 9/2012 | Muranaka et al. |
| 2016/0046912 A1 | 2/2016 | Muranaka et al. |
| 2019/0059390 A1 | 2/2019 | Djonovic et al. |
| 2021/0204505 A1 | 7/2021 | Djonovic et al. |

FOREIGN PATENT DOCUMENTS

| | | |
|---|---|---|
| JP | 6344774 B2 | 6/2018 |
| WO | WO 2016/200987 A1 | 12/2016 |
| WO | WO 2019/090181 A1 | 5/2019 |
| WO | WO 2020/049572 A1 | 3/2020 |

OTHER PUBLICATIONS

Seki, H., Ohyama, K., Sawai, S., Mizutani, M., Ohnishi, T., Sudo, H., . . . & Muranaka, T. (2008). Licorice β-amyrin 11-oxidase, a cytochrome P450 with a key role in the biosynthesis of the triterpene sweetener glycyrrhizin. Proceedings of the National Academy of Sciences, 105(37), 14204-14209. (Year: 2008).*

Nomura, Y., Seki, H., Suzuki, T., Ohyama, K., Mizutani, M., Kaku, T., . . . & Muranaka, T. (2019). Functional specialization of UDP-glycosyltransferase 73P12 in licorice to produce a sweet triterpenoid saponin, glycyrrhizin. The Plant Journal, 99(6), 1127-1143. (Year: 2019).*

Nazari, S., Rameshrad, M., & Hosseinzadeh, H. (2017). Toxicological effects of *Glycyrrhiza glabra* (licorice): a review. Phytotherapy research, 31(11), 1635-1650. (Year: 2017).*

Lazar, E., Vicenzi, E., Van Obberghen-Schilling, E., Wolff, B., Dalton, S., Watanabe, S., & Sporn, M. B. (1989). Transforming growth factor α: An aromatic side chain at position 38 is essential for biological activity. Molecular and cellular biology, 9(2), 860-864. (Year: 1989).*

Nonaka, T., Kametani, F., Arai, T., Akiyama, H., & Hasegawa, M. (2009). Truncation and pathogenic mutations facilitate the formation of intracellular aggregates of TDP-43. Human molecular genetics, 18(18), 3353-3364. (Year: 2009).*

Schmutz et al. (2010). Genome sequence of the palaeopolyploid soybean. Nature, 463:178-183. (Year: 2010).*

UniProt Database Submission, Accession ID: 11KFY7_SOYBN. Schmutz et al. (2010). Genome sequence of the palaeopolyploid soybean. Nature, 463:178-183, submitted Jun. 13, 2012. (Year: 2010).*

Combined Chinese Office Action and Search Report issued Aug. 12, 2023 in Chinese Patent Application No. 202080087149.1 (with English Translation of Category of Cited Documents), 10 pages.

Xie et al., "Cellulose Synthase-like protein G1 [Glycine soja]", GenBank, RZC10151.1, Feb. 13, 2019, 1 page.

International Search Report dated Dec. 15, 2020 in PCT/JP2020/039175, 3 pages.

Gibson, "Glycyrrhiza in Old and New Perspectives", Lloydia—The Journal of Natural Products, 1978, vol. 41, No. 4, pp. 348-354.

AOA445kh18, SubName: Full=Cellulose synthase-like protein G1, UniProt Sequence Revision History [online], May 8, 2019 uploaded, [retrieved: Nov. 30, 2020], UniProt in particular, sequence, 4 pages.

Jozwiak et al., "Plant terpenoid metabolism co-opts a component of the cell wall biosynthesis machinery", Nature Chemical Biology, 2020, vol. 16, pp. 740-748 (13 total pages).

Partial Supplementary European Search Report issued Nov. 8, 2023 in European Patent Application No. 20877715.1, 13 pages.

Chung, S. et al., "A cellulose synthase-derived enzyme catalyses 3-O-glucuronosylation in saponin biosynthesis," Nature Communications, vol. 11, No. 5664, 2020, 11 pages.

Xu, G. et al., "A novel glucuronosyltransferase has an unprecedented ability to catalyse continuous two-step glucuronosylation of the glycyrrhetinic acid to yield glycyrrhizin," New Phytologist, vol. 212, 2016, 13 pages.

Extended European Search Report issued Apr. 4, 2024 in European Patent Application No. 20877715.1, 13 pages.

"Cellulose synthase-like protein G1," Database UniProt [Online], Database accession No. A0A1S2Y5C3, Apr. 12, 2017, XP093138170, 2 pages.

"Cellulose synthase-like protein D3," Database UniProt [Online], Database accession No. G7IYF6, Jan. 25, 2012, XP093138219, 7 pages.

Young, N. et al., "The Medicago genome provides insight into the evolution of rhizobial symbioses," Nature, vol. 480, No. 7378, Dec. 1, 2011, XP093024788, pp. 520-524.

Extended European Seach Report dated Mar. 11, 2025, in European Patent Application No. 24208479.6 (10 pages).

Hikaru Seki et al., Triterpene Functional Genomics in Licorice for Identification of CYP72A154 Involved in the Biosysnthesis of Glycyrrhizin, The Plant Cell, vol. 23: 4112-4123, Nov. 2011, www.plantcell.org , 2011, American Society of Plant Biologists (12 pages).

Israel Office Action dated Dec. 8, 2025, in Israel Patent Application No. 292111 (4 pages).

\* cited by examiner

Fig. 1

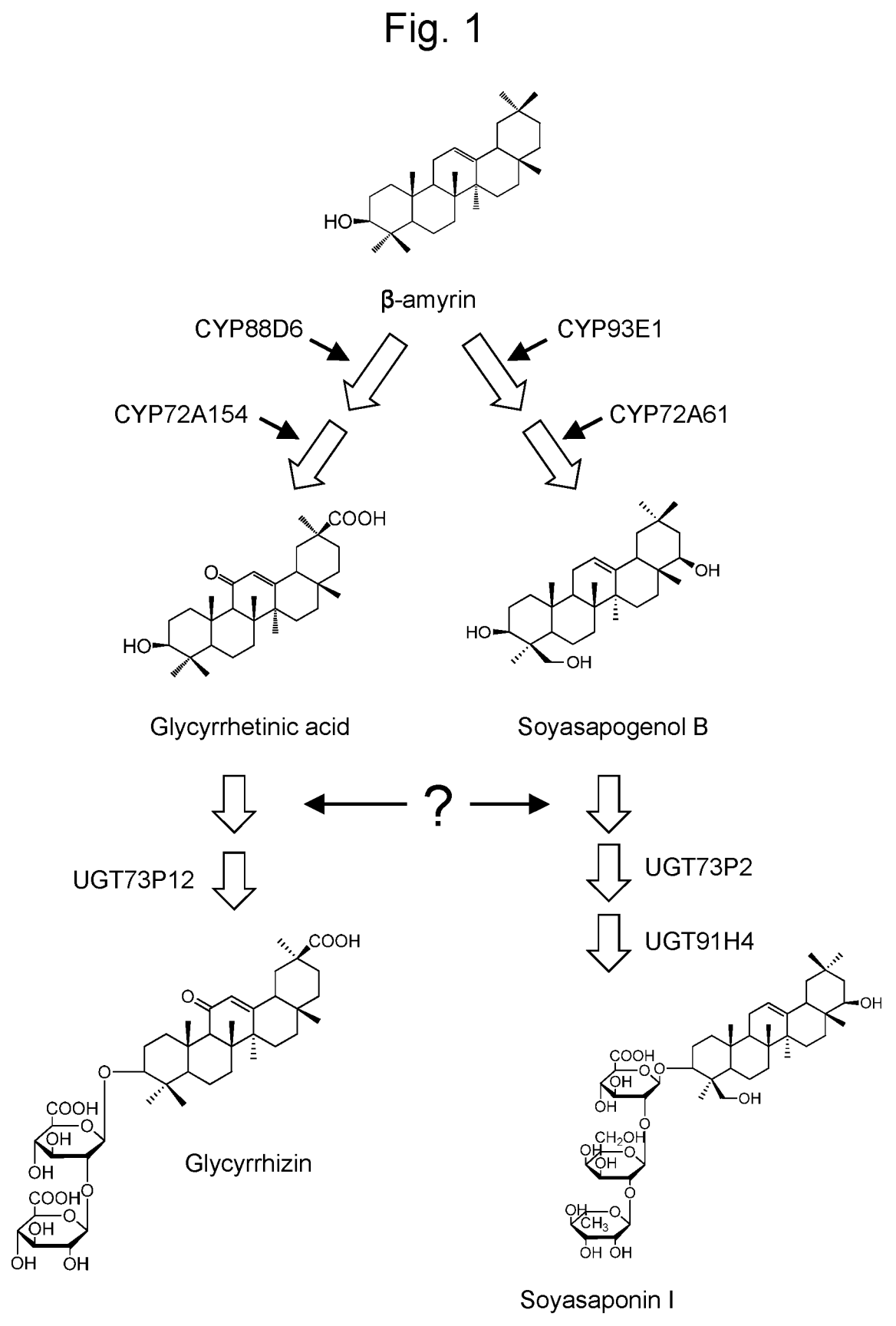

β-amyrin

CYP88D6

CYP72A154

CYP93E1

CYP72A61

Glycyrrhetinic acid

Soyasapogenol B

?

UGT73P12

UGT73P2

UGT91H4

Glycyrrhizin

Soyasaponin I (a)

(b)

(a)    Sample A (Glyma.06G324300)

(b)    Sample B (Glyur003152s00037491)

(c)    Sample C (Lj3g3v1981230)

(d)    Sample D (Negative control)

(a)    Sample E (Glyma.06G324300)

(b)    Sample F (Glyur003152s00037491)

(c)    Sample G (Lj3g3v1981230)

(d)    Sample H (Negative control)

(a)

Glycyrrhetinic acid
(Sugar acceptor, Target ion=470)

Glyma.06G324300

Glycyrrhetinic acid monoglucuronide
(Product, Target ion=646)

(b)

(×10⁷)

Glycyrrhetinic acid m/z: 470

Intensity

Time (min)

(c)

Glycyrrhetinic acid
monoglucuronide (×10⁵)

m/z: 646

Intensity

Time (min)

(a)

Glycyrrhetinic acid
(Sugar acceptor, Target ion=470)

Glyur003152s00037491

Glycyrrhetinic acid monoglucuronide
(Product, Target ion=646)

(b)

(a)

Glycyrrhetinic acid
(Sugar acceptor, Target ion=470)

Lj3g3v1981230

Glycyrrhetinic acid monoglucuronide
(Product, Target ion=646)

(b)

(c)

(a)

Glycyrrhetinic acid
(Sugar acceptor, Target ion=470)

Empty vector

Glycyrrhetinic acid monoglucuronide
(Product, Target ion=646)

(b)

(a)

Soyasapogenol B
(Sugar acceptor, Target ion=458)

Individual sample

Soyasapogenol B monoglucuronide
(Product, Target ion=634)

(b)      Sample M (Glyma.06G324300)

Soyasapogenol B monoglucuronide m/z: 634

(c)      Sample N (Glyur003152s00037491)

Soyasapogenol B monoglucuronide m/z: 634

(d)      Sample O (Lj3g3v1981230)

Soyasapogenol B monoglucuronide m/z: 634

(e)      Sample P (Negative control)

m/z: 634

Fig. 12-1
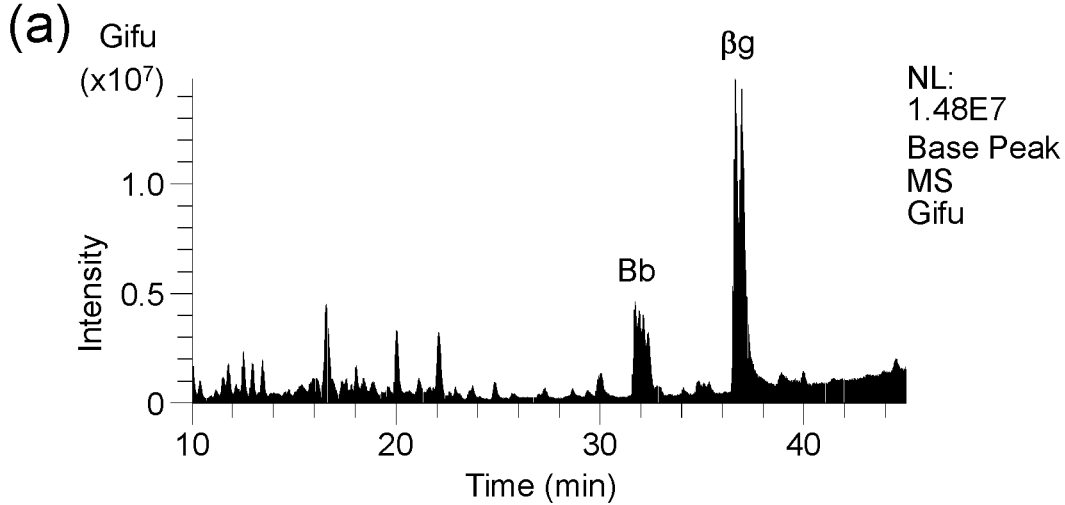
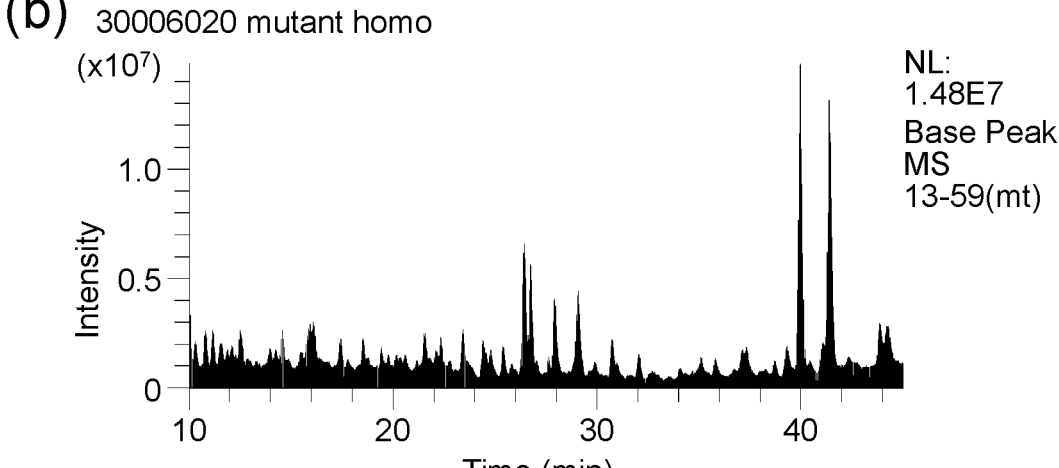
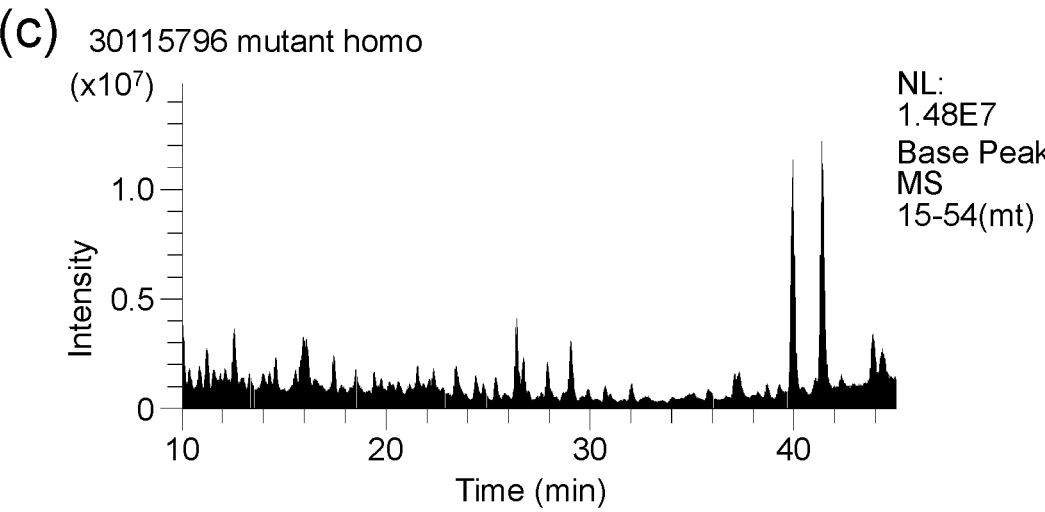

Fig. 12-2
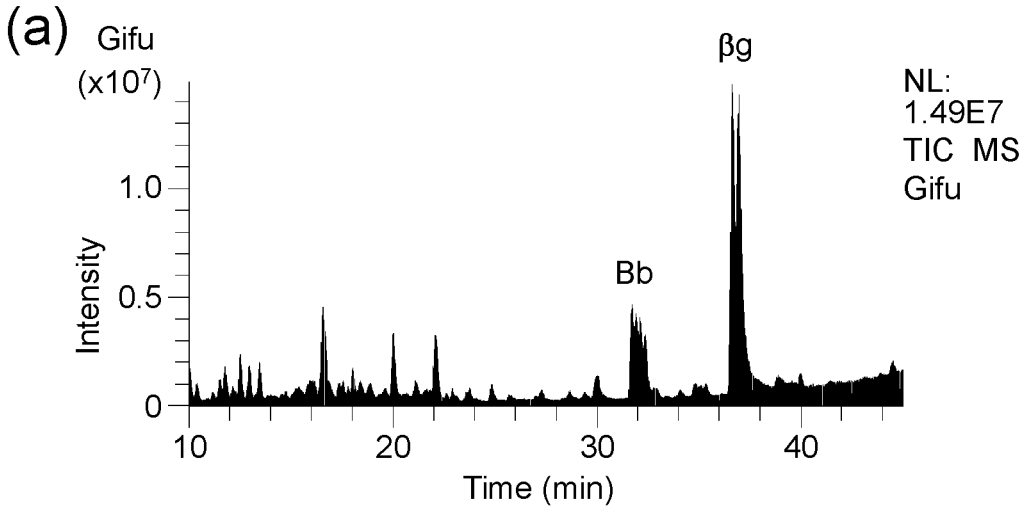
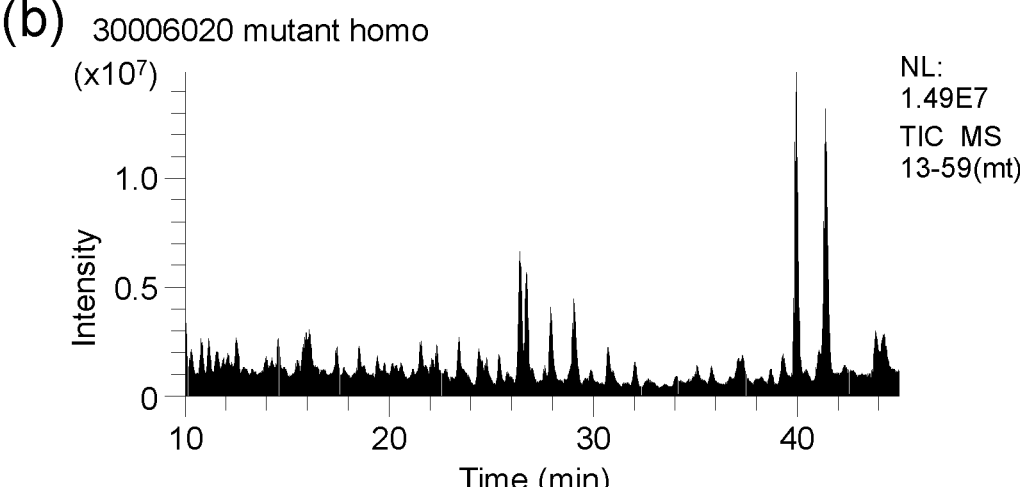
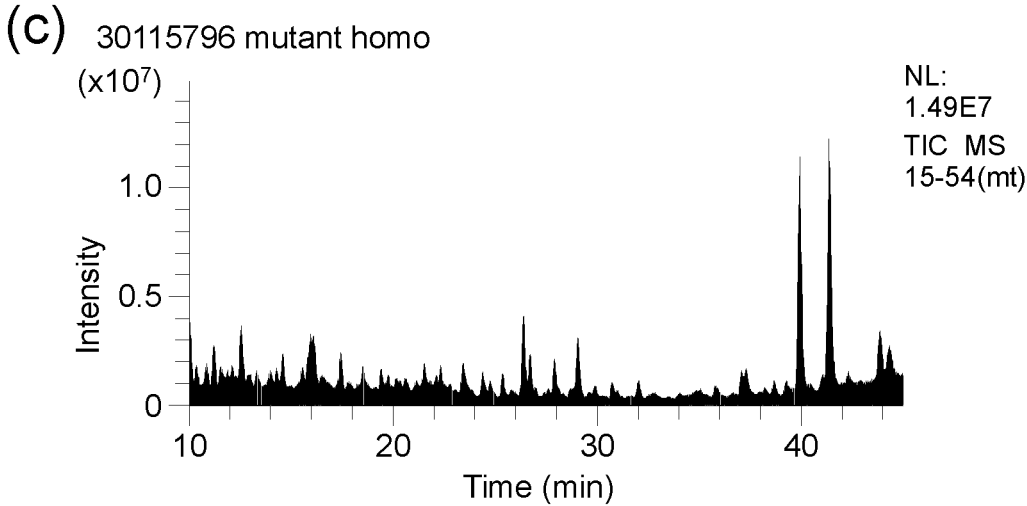

(a)  pG35N_empty / Gifu (b)  pG35N_empty / 30115796

(c)  pG35N_GmCsL / 30115796

(d)  pG35N_GuCsL / 30115796

(e)  pG35N_LjCsL / 30115796

GmCsL: Glyma.06G324300
GuCsL: Glyur003152s00037491
LjCsL: Lj3g3v1981230

(a)  Sample Q (AsCSyGT)

(b)  Sample R (Glyma.04G255400)

(c)  Sample S (Glyma.11G151800)

(a)  Sample T (AsCSyGT)

(b)  Sample U (Glyma.04G255400)

(c)  Sample V (Glyma.11G151800)

(a)

Ursolic acid
(Sugar acceptor, Target ion=455)

Ursolic acid monoglucuronide
(Product, Target ion=631)

(b)   Sample W (Glyma.11G151800)

(c)   Sample X (Negative control)

(a)

Betulinic acid
(Sugar acceptor, Target ion=455)

Betulinic acid monoglucuronide
(Product, Target ion=631)

(b) Sample Y (Glyma.11G151800)

(c) Sample Z (Negative control)

GLUCURONOSYLTRANSFERASE, GENE ENCODING SAME AND METHOD FOR USING THE SAME

TECHNICAL FIELD

The present invention relates to an enzyme for transferring glucuronic acid to the hydroxyl group at the 3-position in an oleanane-type triterpenoid, a gene encoding the enzyme, and a method for producing glycyrrhizin.

BACKGROUND ART

*Glycyrrhiza* (*Glycyrrhiza uralensis*) is a Fabaceae perennial herbaceous plant. Root and stolon of the plant are known as important Chinese herbal medicines (Kampo medicine), "licorice (*Glycyrrhiza* spp.)", and widely used throughout the world. The main active ingredient contained in licorice is glycyrrhizin which is an oleanane-type triterpenoid saponin (Non-Patent Literature 1). Various studies have been conducted on glycyrrhizin for its usefulness in view of herbal medicine and pharmacology, thremmatological aspects, and the like.

In order to stably and continuously provide high-quality glycyrrhizin serving as a medicinal drug by a biological production system, for example, establishment of optimal production conditions by using a gene involved in a glycyrrhizin biosynthetic system or the expression level of the gene as a marker, selection of a high glycyrrhizin production strain, or breeding of the high glycyrrhizin production plant by introducing a synthase gene is required. Therefore, it is indispensable to identify group of genes involved in the glycyrrhizin biosynthetic pathway.

Glycyrrhizin is biologically synthesized from β-amyrin, which is commonly contained in plants and belongs to an oleanane-type triterpenoid, as a starting material, through two-step oxidation reactions and two-step glycosylation reactions. β-amyrin is known as a precursor substance, from which glycyrrhizin and soyasaponin I are biologically synthesized in a triterpenoid saponin biosynthetic pathway, in short, it serves as a branching point for biosynthesis of glycyrrhizin and soyasaponin I (FIG. 1).

As shown in FIG. 2, up to the present, as biosynthetic enzymes involved in the pathway from β-amyrin to glycyrrhizin, two types of oxidases have been known, namely, CYP88D6 (β-amyrin 11-oxidase; Patent Literature 1) and CYP72A154 (11-oxo-β-amyrin 30-oxidase; Patent Literature 2), which respectively catalyze each of the two-step oxidation reactions for biologically synthesizing glycyrrhetinic acid (which is an aglycone of glycyrrhizin) from β-amyrin. In addition, among the biosynthetic enzymes catalyzing two-step glycosylation reactions to biologically synthesize glycyrrhizin from the resulting glycyrrhetinic acid, a glycosyltransferase UGT73P12 (UDP-glycosyltransferase 73P12; Patent Literature 3), which catalyzes the second-step glycosylation reaction, has been known. Many skilled scientists in this field have repeatedly attempted to isolate glycosyltransferase, namely glucuronosyltransferase 1, which catalyzes the first-step of the glycosylation reaction of transferring glucuronic acid directly to glycyrrhetinic acid. Despite all their efforts, they could not have isolated the enzyme yet, which was a bottleneck in synthesizing glycyrrhizin from β-amyrin in a biological production system or in vitro synthetic system. Therefore, they have failed to stably and continuously provide a sufficient amount of glycyrrhizin.

CITATION LIST

Patent Literature

Patent Literature 1: Japanese Patent No. 5526323
Patent Literature 2: Japanese Patent No. 5771846
Patent Literature 3: Japanese Patent No. 6344774

Non-Patent Literature

Non-Patent Literature 1: Gibson, M. R., 1978, Lloydia— the journal of Natural Products, 41 (4): 348-354

SUMMARY OF INVENTION

Technical Problem

In order to solve the above-mentioned problem, the present invention is aimed at isolating a glucuronosyltransferase 1 gene, which catalyzes glucuronic acid transfer to the hydroxyl group at the 3-position of an oleanane-type triterpenoid including glycyrrhetinic acid. The present invention is also aimed at preparing and providing a biological expression system capable of biologically synthesizing a large amount of glycyrrhizin from β-amyrin in an individual or a cell using the gene expression system for glucuronosyltransferase 1.

Solution to Problem

In the biosynthetic pathway from β-amyrin to glycyrrhizin, many skilled persons in the art have attempted to isolate the last remnant glucuronosyltransferase 1 from *Glycyrrhiza*. However, glucuronosyltransferase I could not have been isolated for many years. Therefore, the present inventors considered that there is some difficult factor in the isolation of glucuronosyltransferase 1 from *Glycyrrhiza* plants, and attempted to isolate the glucuronosyltransferase 1 from plants other than *Glycyrrhiza* plants. In Fabaceae plants to which *Glycyrrhiza* plants belong, there is generally a pathway for biologically synthesizing soyasaponin I from β-amyrin via soyasapogenol B as an intermediate product (FIG. 1). Soyasapogenol B, an oleanane-type triterpenoid, has a hydroxyl group at the 3-position, while the final product, soyasaponin I, has glucuronic acid bound at the 3-position. It is like a case where glycyrrhetinic acid, which is an intermediate product and is also an oleanane-type triterpenoid, has a hydroxyl group at the 3-position, whereas glycyrrhizin, which is a final product, has glucuronic acid bound at the 3-position. That is, glucuronosyltransferase 1 that functions in the biosynthetic pathway from β-amyrin to glycyrrhizin may also function in the biosynthetic pathway from β-amyrin to soyasaponin I. Based on the hypothesis, the present inventors attempted to isolate genes having glucuronic acid transfer activity 1 from soy beans (*Glycine max*) having a pathway for biologically synthesizing soyasaponin I from β-amyrin. As a result, the present inventors succeeded in isolating a cellulose synthase analogous gene whose specific function is unknown. The transglycosylation activity of this enzyme was verified using soyasapogenol B as a sugar acceptor substrate. As a result, it was found that glucuronic acid is transglycosylated to the hydroxyl group at the 3-position in soyasapogenol B. This enzyme activity was similar in a case where the sugar acceptor substrate is glycyrrhetinic acid. Thus, the present inventors shifted from *Glycyrrhiza* plants to soybean as a plant from which glucuronosyltransferase 1 is derived, and succeeded in identifying glucuronosyltransferase 1 which could not have been isolated before. The present invention is based on the research results, and provides the following.

(1) A polypeptide having an activity to transfer glucuronic acid to the hydroxy group at the 3-position in an oleanane-type triterpenoid, and comprising any one of amino acid sequences of the following (a) to (c), or a fragment thereof having the activity:

(a) an amino acid sequence represented by any one of SEQ ID NOs: 1, 3, and 5, (b) an amino acid sequence derived from the amino acid sequence represented by any one of SEQ ID NOs: 1, 3, and 5 by deletion, replacement or addition of one or a plurality of amino acids, and (c) an amino acid sequence polypeptide having 80% or more identity with the amino acid sequence represented by any one of SEQ ID NOs: 1, 3, and 5.

(2) The polypeptide according to (1), wherein the oleanane-type triterpenoid is selected from the group consisting of β-amyrin, 11-oxo-β-amyrin, 30-hydroxy-11-oxo-β-amyrin, 30-hydroxy-β-amyrin, 24-hydroxy-β-amyrin, 11-deoxoglycyrrhetinic acid, glycyrrhetinic acid, oleanolic acid, medicagenic acid, soyasapogenol B, soyasapogenol A, hederagenin, camelliagenin, and saikogenin.

(3) The polypeptide according to (1) or (2), which is derived from a Fabaceae plant.

(4) A polynucleotide encoding the polypeptide according to any one of (1) to (3).

(5) The polynucleotide according to (4), comprising any one of nucleotide sequences of the following (a) to (d):

(a) a nucleotide sequence represented by any one of SEQ ID NOs: 2, 4, and 6, (b) a nucleotide sequence derived from the nucleotide sequence represented by any one of SEQ ID NOs: 2, 4, and 6 by deletion, replacement or addition of one or a plurality of nucleotides, (c) a nucleotide sequence having 80% or more identity with the nucleotide sequence represented by any one of SEQ ID NOs: 2. 4, and 6, or (d) a nucleotide sequence capable of hybridizing with a complementary nucleotide sequence to the nucleotide sequence represented by any one of SEQ ID NOs: 2, 4, and 6 under high stringent conditions.

(6) A CSyGT (Cellulose synthase superfamily-derived glycosyltransferase 1) expression vector including the polynucleotide according to (4) or (5).

(7) A transformant comprising the polynucleotide according to (4) or (5) or the CSyGT expression vector according to (6), or a progeny thereof having the polynucleotide or the CSyGT expression vector.

(8) The transformant or a progeny thereof according to (7), wherein a host is a Fabaceae plant.

(9) The transformant or a progeny thereof according to (7), wherein a host is a yeast.

(10) The polypeptide according to any one of (1) to (3), prepared by adding a sugar chain derived from the yeast obtained from the transformant or a progeny thereof according to (9).

(11) The polypeptide according to (10), wherein the sugar chain derived from the yeast is high mannose-type sugar chain.

(12) A method for producing a polypeptide having an activity to transfer glucuronic acid to the hydroxy group at the 2-position of glucuronic acid in an oleanane-type triterpenoid, comprising the steps of culturing the transformant or a progeny thereof according to (7) or (8), and extracting the polypeptide according to any one of (1) to (3) from the culture.

(13) A gene recombinant for producing glycyrrhizin, capable of biologically synthesizing β-amyrin and comprising all expression vectors of the following (A) to (D):

(A) a CYP88D6 expression vector encoding a protein having an activity of oxidizing the 11-position in an oleanane-type triterpenoid and comprising a polypeptide containing any one of amino acid sequences of the following (a) to (c):

(a) an amino acid sequence represented by SEQ ID NO: 7, (b) an amino acid sequence derived from the amino acid sequence represented by SEQ ID NO: 7 by deletion, replacement or addition of one or a plurality of amino acids, and (c) an amino acid sequence having 80% or more identity with the amino acid sequence represented by SEQ ID NO: 7, (B) a CYP72A154 expression vector encoding a protein having an activity of oxidizing the 30-position in an oleanane-type triterpenoid and comprising a polypeptide containing any one of amino acid sequences of the following (d) to (f):

(d) an amino acid sequence represented by any one of SEQ ID NOs: 9, 11 and 13, (e) an amino acid sequence derived from the amino acid sequence represented by any one of SEQ ID NOs: 9, 11, and 13 by deletion, replacement or addition of one or a plurality of amino acids, or (f) an amino acid sequence having 80% or more identity with the amino acid sequence represented by any one of SEQ ID NOs: 9, 11, and 13, (C) an UGT73P12 expression vector encoding a protein having an activity to transfer glucuronic acid to the hydroxy group at the 2-position of glucuronic acid in an oleanane-type triterpenoid monoglucuronide and comprising a polypeptide containing any one of amino acid sequences of the following (g) to (i):

(g) an amino acid sequence represented by SEQ ID NO: 15, (h) an amino acid sequence derived from the amino acid sequence represented by SEQ ID NO: 15 by deletion, replacement or addition of one or a plurality of amino acids, or (i) an amino acid sequence having 80% or more identity with the amino acid sequence represented by SEQ ID NO: 15, and (D) a CSyGT expression vector according to (6).

(14) The gene recombinant according to (13), wherein a host is a Fabaceae plant.

(15) A method for producing glycyrrhizin from β-amyrin, comprising a step of culturing the gene recombinant according to (13) or (14).

The specification incorporates the contents disclosed in the specification of Japanese Patent Application No. 2019-190060 based on which the priority of the present application is claimed.

Advantageous Effects of Invention

According to the present invention, there is provided a polypeptide having an activity to transfer glucuronic acid to the hydroxy group at the 3-position in an oleanane-type triterpenoid, a polynucleotide encoding the polypeptide, or use thereof.

BRIEF DESCRIPTION OF DRAWINGS

FIG. 1 shows biosynthetic pathways of glycyrrhizin and soyasaponin I in a triterpenoid saponin biosynthetic system.

FIG. 12-1 shows LC-PDA/MS/MS analysis results of *Lotus japonicus* Glyma.06G324300 homologous gene loss-of-function mutant extract. (a) shows a base peak ion chromatogram of a plant extract derived from wild-type (Gifu), and (b) and (c) show base peak ion chromatograms of plant extracts derived from transposon insertion homozygous mutants (30006020 and 30115796, respectively).

FIG. 12-2 shows LC-PDA/MS/MS analysis results of *Lotus japonicus*-Glyma.06G324300 homologous gene loss-of-function mutant extract. (a) shows a total ion chromatogram of a plant extract derived from wild-type (Gifu), and (b) and (c) show total ion chromatograms of plant extracts derived from transposon insertion homozygous mutants (30006020 and 30115796, respectively).

Figure 17:
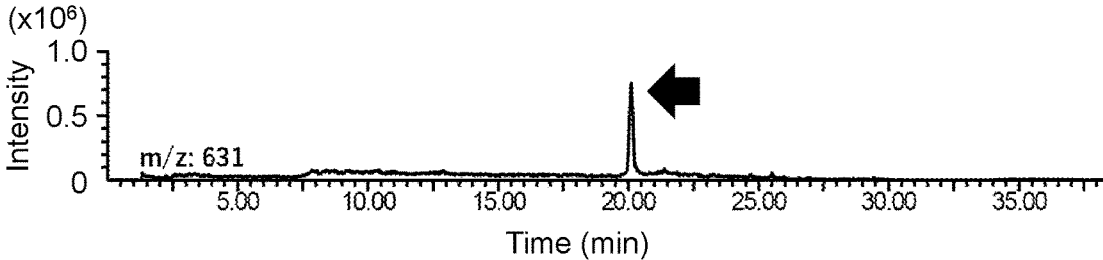
Figure 17:
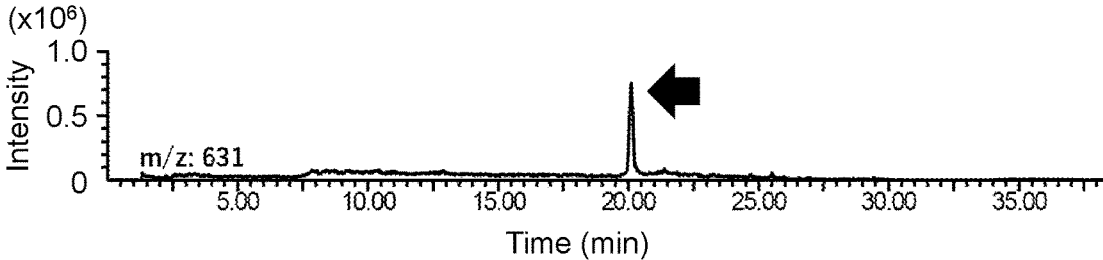
Figure 17:
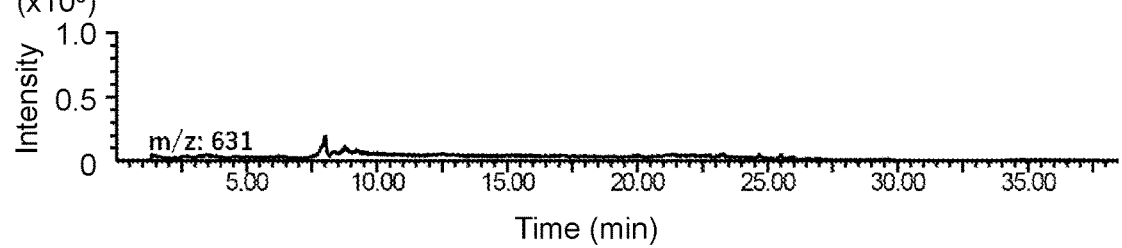

FIG. 17 shows metabolite analysis results in soy bean-derived Glyma.11g151800 gene-introduced yeast, to which betulinic acid was fed. (a) is a conceptual diagram showing envisaged conversion reactions to betulinic acid monoglucuronide when Glyma.11g151800 feeding assay extract (sample Y) was used. (b) shows detection results of betulinic acid monoglucuronide generated by Glyma.11g151800 when sample Y was added. The peak pointed by a solid arrow shows betulinic acid monoglucuronide. (c) shows detection results of betulinic acid monoglucuronide when sample Z as a negative control was added.

DESCRIPTION OF EMBODIMENTS

1. Glucuronosyltransferase 1 (CSyGT)

1-1. Summary

A first aspect of the present invention relates to glucuronosyltransferase 1 and a fragment thereof having glucuronic acid transfer activity 1, and nucleic acid encoding them. The glucuronosyltransferase 1 of the present invention has an activity to catalyze a glycosylation reaction of glucuronic acid to the hydroxyl group at the 3-position of glycyrrhetinic acid which is generated from β-amyrin via two-step oxidation reaction, in a synthetic pathway peculiar to the genus *Glycyrrhiza* that biologically synthesizes glycyrrhizin from β-amyrin which can be biologically synthesized by many plants. The glucuronosyltransferase 1 of the present invention or the like enables not only sugar transfer of glucuronic acid to the hydroxyl group at the 3-position of oleanane-type triterpenoids including glycyrrhetinic acid, but also creation of a biological production system from β-amyrin to glycyrrhizin using a plant other than a *Glycyrrhiza* plant as a host, by combining with known enzyme involving in a biosynthetic pathway from β-amyrin to glycyrrhizin. Thereby, high quality glycyrrhizin can be stably and continuously provided.

1-2. Definition of Terms

The terms frequently used herein are defined as follows:
In the specification, the "glucuronosyltransferase 1 (CSyGT)" (often referred to as "CSyGT" in the specification) refers to an enzyme catalyzing a sugar transfer reaction to an oleanane-type triterpenoid having the hydroxyl group at the 3-position carbon, the sugar transfer reaction including transferring a single glucuronic acid, a kind of sugar, to the hydroxyl group of the oleanane-type triterpenoid. The term "first" as used herein means to have the first transglycosylation activity in a two-step sugar transfer reaction at the hydroxyl group at the 3-position of the oleanane-type triterpenoid. The specific configuration of glucuronosyltransferase 1 will be described later.

In the specification, "fragment thereof having glucuronic acid transfer activity 1" refers to an active fragment of the glucuronosyltransferase 1.

In the specification, "glucuronic acid transfer activity 1" refers to an activity of the CSyGT to catalyze a sugar transfer reaction, that is, an activity to transfer glucuronic acid to the hydroxyl group at the 3-position in an oleanane-type triterpenoid. Owing to the activity, an oleanane-type triterpenoid monoglucuronide is produced from an oleanane-type triterpenoid. Note that, in the specification, CSyGT and a fragment thereof having glucuronic acid transfer activity 1 are often collectively referred to as "polypeptide having glucuronic acid transfer activity 1" or "glucuronosyltransferase 1 or the like (CSyGT or the like)". Note that, in the specification, glucuronosyltransferase 1 and the like may be a glycoprotein prepared by adding different sugar chains. For example, glucuronosyltransferase 1 and the like prepared by adding a plant-derived sugar chain, and glucuronosyltransferase 1 and the like prepared by adding a yeast-derived sugar chain are both included in glucuronosyltransferase 1 and the like in the specification.

The "oleanane-type triterpenoid" refers to C30 isoprenoid having a pentacyclic oleanane skeleton and comprised of 6 isoprene units, and corresponds to aglycone of glycyrrhizin which is a final objective product in the invention. The oleanane-type triterpenoid described in the specification refers to an oleanane-type triterpenoid having the hydroxyl group (OH group) at the 3-position, unless otherwise indicated. Specific examples of the oleanane-type triterpenoid are not limited, but include β-amyrin, 11-oxo-β-amyrin, 30-hydroxy-11-oxo-β-amyrin, 30-hydroxy-β-amyrin, 24-hydroxy-β-amyrin, 11-deoxoglycyrrhetinic acid, glycyrrhetinic acid, oleanolic acid, medicagenic acid, soyasapogenol B, soyasapogenol A, hederagenin, camelliagenin, and saikogenin. All of them can be substrates for glucuronosyltransferase 1 of the present invention. Owing to glucuronic acid transfer activity, β-amyrin-3-O-monoglucuronide, 11-oxo-β-amyrin-3-O-monoglucuronide, 30-hydroxy-11-oxo-β-amyrin-3-O-monoglucuronide, 30-hydroxy-β-amyrin-3-O-monoglucuronide, 24-hydroxy-β-amyrin-3-O-monoglucuronide, 11-deoxoglycyrrhetinic acid-3-O-monoglucuronide, glycyrrhetinic acid-3-O-monoglucuronide, oleanolic acid-3-O-monoglucuronide, medicagenic acid-3-O-monoglucuronide, soyasapogenol B-3-O-monoglucuronide, soyasapogenol A-3-O-monoglucuronide, hederagenin-3-O-monoglucuronide, camelliagenin-3-O-monoglucuronide, and saikogenin-3-O-monoglucuronide are biologically synthesized from the substrate.

In the specification, Fabaceae plants are not limited to Glycyrrhiza plants, but include all plant species belonging to the Fabaceae family according to plant taxonomy. Examples thereof include an Arachis plant, a Cicer plant, an Aspalathus plant, a Dalbergia plant, a Pterocarpus plant, a Desmodium plant, a Lespedeza plant, an Uraria plant, a Galegeae plant, an Astragalus plant, a Glycyrrhiza plant, an Oxytropis plant, an Augyrocytisus plant, a Cytisus plant, a Genista plant, a Spartium plant, a Hedysarum plant, a Cyamopsis plant, an Indigofera plant, a Lotus japonicus (Lotus) plant, a Lupinus plant, a Wisteria plant, a Cajanus plant, a Canavalia plant, an Erythrina plant, a soybean (Glycine) plant, a Hardenbergia plant, a Lablab plant, a Mucuna plant, a Phaseolus plant, a Psophocarpus plant, a Pueraria plant, a Vigna plant, a Robinia plant, a Castanospermum plant, a Maackia plant, an Ormosia plant, a Sophora plant, a Styphnolobium plant, a Medicago plant, a Trigonella plant, a Trifolium plant, a Lathyrus plant, a Lens plant, a Pisum plant and a Vicia plant. Glycyrrhiza plants to which G. uralensis belongs, and their related species, Medicago plants, have a biosynthetic pathway for glycyrrhetinic acid which is a substrate of CSyGT in biologically synthesizing glycyrrhizin. Therefore, they are suitable for Fabaceae plants of the present invention. Specific examples of the Glycyrrhiza plant include G. glabra, G. inflata, G. aspera, G. eurycarpa, G. pallidiflora, G. yunnanensis, G. lepidota, G. echinata, and G. acanthocarpa. Specific examples of the Medicago plant include M. truncatula.

1-3. Configuration

The glucuronosyltransferase 1 of the present invention (CSyGT) is a polypeptide consisting of amino acid sequences represented by any one of SEQ ID NOs: 1, 3, and 5. These polypeptides respectively corresponds to soy bean (Glycine max) derived wild-type CSyGT(GmCSyGT), Glycyrrhiza (G. uralensis) derived wild-type CSyGT(GuCSyGT), and Lotus japonicus-(Lotus japonicus) derived wild-type CSyGT (LjCSyGT). Glycyrrhiza-derived GuCSyGT has 81% amino acid identity with soybean-derived GmCSyGT. Lotus japonicus-derived LjCSyGT has 82% amino acid identity with soy bean-derived GmCSyGT.

CSyGT may have orthologs in many other plant species other than the above described plant species, especially in the Fabaceae plant species. The CSyGT of the present invention includes, in addition to such heterologous wild-type CSyGT orthologs, homologous wild-type CSyGT paralogs and mutant CSyGT that have glucuronic acid transfer activity 1. Examples of such heterologous wild-type CSyGT orthologs and mutant CSyGT include amino acid sequence derived from the amino acid sequence represented by any one of SEQ ID NOS: 1, 3, and 5 by deletion, replacement or addition of one or a plurality of amino acids, or polypeptides having 80% or more, 82% or more, 85% or more, 87% or more, 90% or more, 91% or more, 92% or more, 93% or more, 94% or more, 95% or more, 96% or more, 97% or more, 98% or more, or 99% or more and less than 100% amino acid identity with the amino acid sequence represented by any one of SEQ ID NOs: 1, 3, and 5. In fact, as opposed to soy bean GmCSyGT, GuCSyGT and LjCSyGT are Glycyrrhiza and Lotus japonicus CSyGT orthologs, respectively, and have 80% or more amino acid identity as described above. Specific examples of mutant CSyGT having glucuronic acid transfer activity 1 includes without limitation splicing variants, mutants based on SNPs.

In the specification, the term "plurality" refers to, for example, 2 to 20, 2 to 15, 2 to 10, 2 to 7, 2 to 5, 2 to 4 or 2 to 3. "Amino acid identity" refers to the ratio (%) of the number of matched amino acid residues to the total number of amino acid residues in the amino acid sequences of the two polypeptides to be compared, when aligned by inserting gaps in one or both as necessary to maximize the number of matched amino acid residues. Alignment of the two amino acid sequences for calculating amino acid identity can be done using known programs such as Blast, FASTA, ClustalW, etc.

In the specification, "replacement (of amino acid)" refers to replacement within a group of conservative amino acids having similar properties such as charge, side chains, polarity, and aromaticity, among 20 amino acids constituting naturally occurring protein. Examples include replacement within a group of uncharged polar amino acids having slightly polar sidechains (Gly, Asn, Gln, Ser, Thr, Cys, Tyr), replacement within a group of branched chain amino acids (Leu, Val, Ile), replacement within a group of neutral amino acids (Gly, Ile, Val, Leu, Ala, Met, Pro), replacement within a group of neutral amino acids having hydrophilic side chains (Asn, Gln, Thr, Ser, Tyr, Cys), replacement within a group of acidic amino acids (Asp, Glu), replacement within a group of basic amino acids (Arg. Lys, His), and replacement within a group of aromatic amino acid (Phe, Tyr, Trp). Amino acid replacements within these groups are preferred because they are known to be less likely to cause changes in the properties of polypeptides.

In the present aspect, the "active fragment thereof" refers to a polypeptide fragment containing a region of glucuronosyltransferase 1 and having glucuronic acid transfer activity 1. An example is a polypeptide fragment containing a substrate-binding site of glucuronosyltransferase 1. An example of the substrate of the glucuronosyltransferase 1 of the present invention includes the above-described oleanane-type triterpenoid. Glycyrrhetinic acid is preferred. The length of the amino acids of the polypeptide constituting the active fragment is not particularly limited. The region may consist of continuous amino acids of, for example, at least 10, 15, 20, 25, 30, 50, 100 or 150 in (a) to (c) polypeptides.

Note that, in the specification, CSyGT and an active fragment thereof are often collectively referred to as "CSyGT and the like (glucuronosyltransferase 1 and the like)".

According to the CSyGT or the like of the present invention, an oleanane-type triterpenoid monoglucuronide can be obtained by transglycosylating glucuronic acid to the hydroxyl group at the 3-position, using an oleanane-type triterpenoid as a sugar acceptor substrate by glucuronic acid transfer activity 1.

In the biosynthetic system of glycyrrhizin in *Glycyrrhiza*, the pathway for biosynthesis from β-amyrin, which is an oleanane-type triterpenoid and also said to be an original substance, to glycyrrhetinic acid has already been known, and it is also possible to be artificially biosynthesized. Further, the pathway for biologically synthesizing glycyrrhizin, in which glucuronic acid is further transglycosylated to glycyrrhetinic acid monoglucuronide prepared by transglycosylating one molecule of glucuronic acid to glycyrrhetinic acid, has also been known. That is, in the pathway for biologically synthesizing glycyrrhizin from β-amyrin, only the pathway of biologically synthesizing glycyrrhetinic acid monoglucuronide by transglycosylating glucuronic acid to glycyrrhetinic acid has been unknown. However, the present invention has revealed all of the biosynthetic pathways of glycyrrhizin in *Glycyrrhiza*, which enables in vitro synthesis from β-amyrin to glycyrrhizin. Further, since β-amyrin can be biologically synthesized from a lot of plant species other than *Glycyrrhiza*, in vivo synthesis system using ordinary ones among such plant species as a host can also be utilized. Furthermore, an organism can be used together with a gene biologically synthesizing β-amyrin so as to enable in vivo synthesis system using the organism as a host, even if the organism is other than a plant, as long as the organism does not contain β-amyrin but can biologically synthesize a precursor of β-amyrin.

2. Glucuronosyltransferase 1 Gene (CSyGT Gene) and Active Fragment Thereof

2-1. Summary

A second aspect of the present invention relates to a polynucleotide encoding the polypeptide (CSyGT and the like) described in the first aspect, that is, a glucuronosyltransferase 1 gene and an active fragment thereof. The polynucleotide of the present invention enables the construction of the recombinant vector of the third aspect described below.

2-2. Configuration

The "glucuronosyltransferase 1 gene" (often referred to herein as "CSyGT gene") refers to a polynucleotide encoding CSyGT described in the first aspect. The nucleotide sequence of the polynucleotide is not particularly limited as long as the polynucleotide encodes CSyGT. The polynucleotide is preferably a polynucleotide encoding a wild-type CSyGT containing amino acid sequence represented by SEQ ID NOs: 1, 3 or 5. Examples include a polynucleotide encoding soybean-derived wild-type GmCSyGT consisting of the amino acid sequence represented by SEQ ID NO: 1, specifically for example, a polynucleotide consisting of the nucleotide sequence represented by SEQ ID NO: 2, that is, soy bean-derived wild-type GmCSyGT gene. Further, examples include a polynucleotide encoding *Glycyrrhiza*-derived wild-type GuCSyGT consisting of the amino acid sequence represented by SEQ ID NO: 3, specifically for example, a polynucleotide consisting of the nucleotide sequence represented by SEQ ID NO: 4, that is, *Glycyrrhiza*-derived wild-type GuCSyGT gene. In addition, examples include a polynucleotide encoding *Lotus japonicus*-derived wild-type LjCSyGT consisting of the amino acid sequence represented by SEQ ID NO: 5, specifically for example, a polynucleotide consisting of the nucleotide sequence represented by SEQ ID NO: 6, that is, *Lotus japonicus*-derived wild-type LjCSyGT gene.

In addition, heterologous ortholog of the wild-type CSyGT gene, and mutant CSyGT genes maintaining the enzyme activity are also included. Examples of such CSyGT genes include polynucleotides containing nucleotide sequences derived from the wild-type CSyGT gene by deletion, replacement or addition of one or a plurality of nucleotides. Specifically, included are, for example, polynucleotides containing nucleotide sequences derived from any nucleotide of soy bean-derived wild-type GmCSyGT gene (for example, polynucleotide consisting of the nucleotide sequence represented by SEQ ID NO: 2), *Glycyrrhiza*-derived wild-type GuCSyGT gene (for example, polynucleotide consisting of the nucleotide sequence represented by SEQ ID NO: 4), and *Lotus japonicus*-derived wild-type LjCSyGT gene (for example, polynucleotide consisting of the nucleotide sequence represented by SEQ ID NO: 6) by deletion, replacement, or addition of one or a plurality of nucleotides.

Further, examples include polynucleotides containing nucleotide sequences having 80% or more, 85% or more, 87% or more, 90% or more, 95% or more, or 99% or more and less than 100% amino acid identity of nucleotide identity with the wild-type CSyGT gene. Specifically, included are, for example, polynucleotides containing nucleotide sequence having 80% or more, 85% or more, 87% or more, 90% or more, 95% or more, or 99% or more and less than 100% nucleotide identity with nucleotide sequence of any one of soy bean-derived wild-type GmCSyGT gene (for example, polynucleotide consisting of the nucleotide sequence represented by SEQ ID NO: 2), *Glycyrrhiza*-derived wild-type GuCSyGT gene (for example, a polynucleotide consisting of the nucleotide sequence represented by SEQ ID NO: 4), and *Lotus japonicus*-derived wild-type LjCSyGT gene (for example, polynucleotide consisting of the nucleotide sequence represented by SEQ ID NO: 6).

Also included is a polynucleotide containing a nucleotide sequence which hybridizes with a nucleotide fragment consisting of nucleotide sequence complementary to the partial nucleotide sequence of the wild-type CSyGT gene under high stringent conditions, and having the enzyme activity.

In the specification, "stringent condition" means a condition under which a non-specific hybrid is less likely to be formed. In the specification, "high stringent condition" refers to a condition under which a non-specific hybrid is still less likely to be formed, or is not formed. Generally, in the reaction condition, the lower the salt concentration and the higher the temperature, the higher the stringent conditions. For example, it corresponds to, for example, a condition of washing with 0.1×SSC and 0.1% SDS at 50° C. to 70° C., 55° C. to 68° C., or 65° C. to 68° C. in washing after hybridization. In addition, stringency of hybridization can be increased by appropriately combining other conditions such as probe concentration, probe nucleotide length, and hybridization time.

In the present aspect, "active fragment thereof" refers to a fragment of CSyGT gene, in which a polypeptide encoded by the fragment has CSyGT activity. Substantially, a polynucleotide encoding the active fragment of CSyGT described in the first aspect corresponds thereto. Therefore, the length of the nucleotide sequence of the polynucleotide constituting the active fragment, that is, the nucleotide number may be three time the amino acid sequence in the active fragment of CSyGT described in the first aspect.

According to the polynucleotide of the present invention or an active fragment thereof, a recombinant vector capable of expressing CSyGT and an active fragment thereof in a host cell can be constructed.

Note that, in the specification, CSyGT gene and an active fragment thereof are often collectively referred to as "CSyGT gene or the like (glucuronosyltransferase 1 gene or the like)".

The CSyGT gene and the like of the present aspect can be isolated from a suitable plant, for example, a Fabaceae plant by a known method. For example, based on the nucleotide sequence of the soy bean-derived wild-type GmCSyGT gene represented by SEQ ID NO: 2, a primer pair having an appropriate nucleotide sequence length is designed. A specific example includes the primer pair represented by SEQ ID NOs: 17 and 18. The GmCSyGT gene can be obtained by using the pair and performing a nucleic acid amplification reaction such as PCR using a nucleic acid derived from soybean DNA library or genomic DNA library as a template. The polynucleotide of the present invention can be also obtained from the library or the like by hybridization using a nucleic acid fragment consisting of a part of the nucleotide sequence represented by SEQ ID NO: 2 as a probe. As to these methods, the methods described in Green & Sambrook, Molecular Cloning, 2012, Fourth Ed., Cold Spring Harbor Laboratory Press may be referred to.

3. Recombinant Vector

3-1. Summary

A third aspect of the present invention relates to a recombinant vector. The recombinant vector of the present invention contains the polynucleotide described in the second aspect, and is capable of cloning CSyGT gene and the like or expressing CSyGT and the like in a host cell. In the present aspect, in particular, CSyGT expression vectors expressing CSyGT and the like are preferably applicable.

3-2. Configuration

The recombinant vector of the present invention can be constructed by introducing the polynucleotide described in the second aspect into an appropriate recombinant vector. The type of vector is not particularly limited and may appropriately be selected depending upon the purpose such as cloning (transformation) or gene expression, or depending upon the host to be introduced. A plant transformation vector or (gene) expression vector is particularly preferable.

In the present invention, "(gene) expression vector" is a gene expression system capable of transporting a polynucleotide encoding an included polypeptide into a target plant cell and expressing the polypeptide. An example includes an expression vector utilizing a plasmid or a virus. In the present invention, CSyGT expression vectors expressing CSyGT and the like integrating CSyGT gene and the like corresponds thereto.

In a case of expression vectors utilizing plasmids (hereinafter often referred to as "plasmid expression vector"), as a plasmid, for example but not limited to, pPZP-based, pSMA-based, pUC-based, pBR-based, pBluescript-based (Agilent Technologies), pTriEX™-based (TAKARA BIO INC.), or pBI-based, pRI-based or pGW-based binary vector or the like may be utilized.

In a case of expression vectors utilizing viruses (hereinafter often referred to as "virus expression vector"), as a virus, cauliflower mosaic virus (CaMV), bean golden mosaic virus (BGMV), tobacco mosaic virus (TMV) or the like can be used.

The recombinant vector includes expression regulatory regions of promoter and terminator. In addition, the recombinant vector can also include enhancers, poly-A addition signals, 5'-UTR (untranslated region) sequences, labelled or selective marker genes, multi-cloning sites, replication origins, and the like. Types of those mentioned above are not particularly limited so long as they can exert their function in a host cell. Those known in the art can be appropriately selected depending on the host into which they are introduced. The case where a plant cell or a plant is used as a host is preferable.

As a promoter, various promoters such as overexpressed promoters, constitutive promoters, site-specific promoters, time-specific promoters, and/or inducible promoters can be used. Specific examples of an overexpressed and constitutive promoter, which is operatable in plant cells include a cauliflower mosaic virus (CaMV)-derived 35S promoter, a promoter of a Ti plasmid-derived nopaline synthase gene (Pnos), a corn-derived ubiquitin promoter, a rice plant-derived actin promoter, and a tobacco-derived PR protein promoter and the like. Small subunits (Rubisco ssu) promoters of ribulose diphosphate carboxylase of various plant species, or histone promoters can also be used. As a workable promoter in bacterial cells, e.g., a promotor of a maltogenic amylase gene of *Bacillus stearothermophilus*, *a*-amylase gene of *Bacillus licheniformis*, a BAN amylase gene of *Bacillus amyloliquefaciens*, an alkaliprotease gene of *Bacillus subtillis* or a xylosidase gene of *Bacillus pumilus*: a PR or PL promoter of phage lambda: or lac, trp or tac promoter of *E. coli* and the like is mentioned. As a workable promoter in yeast host cells, e.g., a promoter derived from a yeast glycolytic gene, an alcohol dehydrogenase gene promoter, a TPII promoter or an ADH2-4c promoter and the like is mentioned. As a workable promoter in fungus, an ADH3 promoter or a tpiA promoter and the like is mentioned. As a workable promoter in animal cells, an SV40 early promoter, an SV40 late promotor or a CMV promoter and the like is mentioned. As a workable promoter in insect cells, a polyhedrin promoter, a P10 promoter, a basic protein promoter of a baculovirus, i.e., *Autographa californica* polyhedrosis, a baculovirus immediate early gene 1 promoter or a baculovirus 39K delayed early gene promoter and the like is mentioned.

As a terminator, for example, a terminator of a nopaline synthase (NOS) gene, a terminator of an octopine synthase (OCS) gene, a CaMV 35S terminator, a 3' terminator of *E. coli* lipopolyprotein lpp, a trp operon terminator, an amyB terminator or a terminator of an ADH1 gene and the like is mentioned. The sequence is not particularly limited as long as it is a sequence capable of terminating the transcription of the gene transcribed by the promoter.

As an enhancer, e.g., an enhancer region including an upstream sequence within the CaMV 35S promoter is mentioned. The enhancer is not particularly limited so long as it can enhance the expression efficiency of nucleic acids or the like encoding active peptides.

As a selecting marker gene, a drug resistant gene (for example, a tetracycline resistant gene, an ampicillin resistant gene, a kanamycin resistant gene, a hygromycin resistant gene, a spectinomycin-resistant gene, a chloramphenicol resistant gene or a neomycin resistant gene): a fluorescent or luminescent reporter gene (for example, luciferase, β-galactosidase, β-glucuronidase (GUS) or green fluorescent protein (GFP)): or an enzyme gene such as a neomycin phosphotransferase II (NPT II) gene or a dihydrofolate reductase gene and the like is mentioned.

According to the recombinant vector of the present invention, e.g., the operation and/or expression of the polynucleotide described in the second aspect can be easily controlled. In addition, expression of CSyGT in the host cell can be operated.

4. Transformant or a Progeny Thereof

4-1. Summary

A fourth aspect of the present invention relates to a transformant or a progeny thereof. The transformant or the progeny thereof of the present invention contains the polynucleotide described in the second aspect or the recombinant vector described in the third aspect in the cell, and is capable of cloning CSyGT gene and the like, and/or expressing CSyGT and the like. According to the transformant of the present invention, CSyGT and the like can be stably biologically synthesized using in vivo expression system.

4-2. Configuration

In the specification, the "transformant" refers to a host transformed by introducing the polynucleotide described in the second aspect or the recombinant vector described in the third aspect.

The host to be transformed is not particularly limited. For example, bacteria such as *Escherichia coli* or *Bacillus subtilis*; yeast such as a budding yeast (*Saccharomyces cerevisiae*), a fission yeast (*Schizosaccharomyces pombe*) or methanol utilizing yeast (*Pichia pastoris*): fungus such as *Aspergillus, Neurospora, Fuzarium* or *Trichoderma*; a monocotyledonous plant or dicotyledonous plant: or a plant cell, a mammal cell or an insect cell (for example, sf9 or sf21) is mentioned. A Fabaceae plant or yeast is preferred.

The transformant of the present invention includes a clone having the same genetic information. For example, if a host is a single cell microbe which asexually reproduces, such as *E. coli* and yeast, a newly produced clone from a first-generation transformant by e.g., fissuration or budding, is also included in the transformant of the invention. If a host is a plant, a part of a plant body taken from a first-generation transformant, for example, a plant tissue such as epidermis, phloem, parenchyma, xylem or fibrovascular bundle, a plant organ such as a leaf, a petal, a stem, a root or a seed: a clone obtained from a plant cell by plant tissue culture, cuttage, grafting or layering: or a newly produced clone by asexual reproduction from a vegetative reproduction organ, which is obtained from a first-generation transformant, such as rhizome, tuberous root, corm or runner, is also included in the transformant of the invention.

The transformant of the present invention may further have one or more other polynucleotides or recombinant vectors, in addition to the polynucleotide described in the second aspect or a recombinant vector described in the third aspect. The other polynucleotides herein refer to polynucleotides except the polynucleotide described in the second aspect. For example, β-amyrin synthase gene, CYP88D6 or CYP72A154 or any one of the oleanane-type triterpenoid monoglucuronide synthase genes corresponds thereto. The other recombinant vectors refer to recombinant vectors except the recombinant vector described in the third aspect.

The transformant of the present invention can be prepared by introducing a polynucleotide or recombinant vector as mentioned above into an appropriate host.

As a method for introducing a polynucleotide or recombinant vector as mentioned above, a method known in the art such as an *agrobacterium* method, a PEG-calcium phosphate method, an electroporation method, a liposomal method, a particle-gun method or a microinjection method can be used. The polynucleotide introduced may be integrated into the genomic DNA of a host or may be present while keeping the state of the polynucleotide (for example, still present in a foreign vector) just introduced. Furthermore, the polynucleotide introduced may be continuously maintained in a host cell like a case where the polynucleotide is integrated into the genomic DNA of a host or may be temporarily retained.

After the polynucleotide described in the second aspect or the recombinant vector described in the third aspect is introduced into a host by the aforementioned method, whether the desired polynucleotide is introduced or not can be checked by e.g., a PCR method, a Southern hybridization method, a Northern hybridization method or an in-situ hybridization.

In the specification, the "progeny thereof" is a progeny obtained by sexual reproduction of a first-generation transformant and means a host having the polynucleotide described in the second aspect or the recombinant vector described in the third aspect of the present invention in an expressible state, and preferably a host progeny having the polynucleotide or the polynucleotide described in the second aspect in the recombinant vector in an expressible state. For example, if the transformant is a plant, a seedling of the transformant corresponds thereto. The generation of the progeny is not a matter.

According to the transformant of the present aspect, an oleanane-type triterpenoid present in a host cell can be converted into an oleanane-type triterpenoid monoglucuronide by enhancing the expression of the polynucleotide introduced. In addition, by changing the host of the transformant, glucuronosyltransferase 1 to which a different sugar chain is added can be obtained. For example, when the host of the transformant is yeast, glucuronosyltransferase 1 to which a high mannose type sugar chain is added is expressed, unlike the case where a Fabaceae plant is used as a host. It is because glycosylation reactions in yeast are different from those in plants (Strasser R. Glycobiology, 2016, 26(9): 926-939).

5. Method for Producing Glucuronosyltransferase 1 and Active Fragment Thereof (CSyGT, Etc.)

5-1. Summary

A fifth aspect of the present invention relates to a method for producing CSyGT and the like, the method comprising culturing transformant of the fourth aspect or a progeny thereof and extracting a polypeptide having glucuronic acid transfer activity 1 described in the first aspect, that is, CSyGT and the like, from a culture thereof. According to the method for producing the polynucleotide of the present invention, CSyGT and the like can be obtained stably and in a large amount by using the host as a biological production system.

5-2. Method

The production method of the present invention includes a culturing step and an extraction step as essential steps. Hereinafter, each step will be specifically described.

(1) Culturing Step

In the present aspect, "culturing step" is a step of culturing a transformant of the fourth aspect or a progeny thereof. As for the transformant or the progeny thereof used in the present invention, it is preferable to use a transformant that can over-express or constitutively express the polypeptide described in the first aspect or a progeny thereof. For example, in a case of a transformant having the recombinant vector described in the third aspect or a progeny thereof, it is preferable that the recombinant vector is an expression vector containing an over-expression promoter or a constitutive promoter. As for the transformant of the fourth aspect or a progeny thereof, any host may be acceptable, but is preferably a Fabaceae plant or yeast. By changing the host, it is possible to obtain glycoproteins to which a different sugar chain is added, even if the same glucuronosyltransferase 1 described in the first step is expressed.

As a medium for culturing, a medium suitable for culturing a host may be appropriately used. As the medium, a medium known in the art can be used. Although the medium is not limited, if culture is made by using bacteria such as *E. coli* as a host, for example, LB medium or M9 medium and the like is mentioned. If culture is made by using a yeast as a host, YPD medium, YPG medium, YPM medium, YPDM medium or SMM medium and the like, is mentioned. If culture is made by using a plant as a host, an appropriate culture soil or a hydroponic culture medium and the like is mentioned.

The medium may appropriately contain, for example, a carbon source (e.g., glucose, glycerin, mannitol, fructose, lactose), a nitrogen source (e.g., an inorganic nitrogen source such as ammonium sulfate, ammonium chloride: an organic nitrogen source such as a casein digest, a yeast extract, polypeptone, BACTO tryptone, a beef extract), an inorganic salt (e.g., sodium diphosphate, potassium diphosphate, magnesium chloride, magnesium sulfate, calcium chloride), a vitamin (e.g., vitamin B1), and a drug (an antibiotic substance such as ampicillin, tetracycline, kanamycin).

The culture conditions are not particularly limited as long as they are appropriate conditions for expressing a polynucleotide. A culture is performed usually at a temperature of 10 to 45° C., 15 to 40° C. or 18 to 37° C., if necessary, while aerating, under irradiation, and/or with stirring for several hours to several hundreds of hours.

(2) Extraction Step

In the present aspect, "extraction step" refers to a step of extracting CSyGT and the like from the culture obtained in the culturing step.

In the specification, "culture" refers to a culture supernatant or a cultured transformant. The CSyGT and the like secreted from the transformant may be contained not only in the cells of the transformant but also in the content supernatant.

To recover the polypeptide described in the first aspect from a culture, the polypeptide present in the culture is extracted by a known method and purified, as needed. For example, a desired polypeptide can be obtained by a solvent extraction method, a salting-out method, a solvent precipitation method, a dialysis method, an ultrafiltration method, a gel electrophoresis method, a gel filtration chromatography, ion exchange chromatography, reversed phase chromatography and affinity chromatography and the like, singly or in appropriate combination. Specifically, see the method of Hayashi et al. (Hayashi et al., 1996, Phytochemistry, 42:665-666) and the method of Noguchi et al. (Noguchi et al., 2007, J. Biol. Chem., 282:23581-23590) mentioned above. It is also possible to recover the desired polypeptide described in the first aspect of interest based on a host-specific sugar chain. For example, when the transformant of the fourth aspect or a progeny thereof is yeast, the expressed polypeptide of the present invention has a high mannose type sugar chain added thereto. Therefore, the polypeptide can also be extracted and purified using mannose-binding lectin (for example, UDA lectin, BC2L-A lectin, etc.).

6. Gene Recombinant for Producing Glycyrrhizin

6-1. Summary

The sixth aspect of the present invention is a gene recombinant for producing glycyrrhizin. The gene recombinant contains an expression vector that expresses one set of enzymes required for the biosynthetic pathway from β-amyrin to glycyrrhizin in *Glycyrrhiza* plants, i.e., a set of four enzymes that catalyze a two-step oxidation reaction and a two-step glycosylation reaction. The gene recombinant of the invention can biologically synthesize glycyrrhizin from β-amyrin in organism cells, and thus can be used as a biological production system for glycyrrhizin.

6-2. Configuration 6-2-1. Included Expression Vector

The gene recombinant of the present invention characteristically contains at least an expression vector that contains a polynucleotide encoding a set of four enzymes and/or an active fragment thereof required for the biosynthetic pathway from β-amyrin to glycyrrhizin in a host cell. If necessary, it may further contain an expression vector containing a polynucleotide encoding a β-amyrin synthase gene. The four enzymes are polypeptides that catalyze respectively the first-step oxidation reaction and the second-step oxidation reaction of B-amyrin, the first-step glycosylation reaction and the second-step glycosylation reaction of oleanane-type triterpenoids. Expression vectors containing each enzyme or an active fragment thereof are shown in (1) to (4) below and will be specifically described. In (1) through (4), each of the four expression vectors is described separately, but the gene for each enzyme may be contained in different expression vectors, or two or more of them may be contained in the same expression vector.

(1) CYP88D6 expression vector

"CYP88D6 expression vector" contains a gene encoding a polypeptide having an activity of oxidizing the 11-position in an oleanane-type triterpenoid, that is, CYP88D6 and an active fragment thereof (often referred to herein as "CYP88D6 and the like") and a fragment thereof (often referred to herein as "CYP88D6 gene and the like"). Therefore, CYP88D6 and the like are expressed by the CYP88D6 expression vectors in the gene recombinant.

Specific examples of the CYP88D6 include, but are not limited to, CYP88D6 derived from *Glycyrrhiza* (*G. uralensis*) consisting of the amino acid sequence represented by SEQ ID NO: 7. Further, a polypeptide having the first-step oxidation activity and consisting of the amino acid sequence derived from the amino acid sequence represented by SEQ ID NO: 7 by deletion, replacement or addition of one or a plurality of amino acids, or consisting of the amino acid sequence having 80% or more identity with the amino acid sequence represented by SEQ ID NO: 7, is also illustrated.

Without limitation, in the gene recombinant of the present invention, 11-oxo-β-amyrin can be produced by mainly using endogenous or exogenous β-amyrin as a substrate and oxidizing the 11-position thereof by a catalytic activity of CYP88D6 and the like expressed by the CYP88D6 expression vector. Alternatively, 30-hydroxy-11-oxo-β-amyrin can be produced by using 30-hydroxy-β-amyrin as a substrate and oxidizing the 11-position thereof. Further alternatively, glycyrrhetinic acid can be produced by using 11-deoxoglycyrrhetinic acid as a substrate and oxidizing the 11-position thereof.

The configuration of the plasmid region in the CYP88D6 expression vector is equivalent to that of the expression vector in the recombinant vector described in the third aspect. The recombinant vector described in Japanese Patent No. 5526323 may also be used.

(2) CYP72A154 Expression Vector

"CYP72A154 expression vector" contains a gene encoding a polypeptide having an activity of oxidizing the 30-position in an oleanane-type triterpenoid, that is, CYP72A154 and an active fragment thereof (often referred to herein as "CYP72A154 and the like") and a fragment thereof (often referred to herein as "CYP72A154 gene and the like"). Therefore, CYP72A154 and the like are expressed by the CYP72A154 expression vectors in the gene recombinant.

Specific examples of the CYP72A154 include, but are not limited to, *Glycyrrhiza* (*G. uralensis*)-derived CYP72A154 consisting of the amino acid sequence represented by SEQ ID NO: 9, *Glycyrrhiza glabra* (*G. glabra*)-derived CYP72A154 consisting of the amino acid sequence represented by SEQ ID NO: 11, and *M. truncatula* (*Medicago truncatula*)-derived CYP72A63 consisting of the amino acid sequence represented by SEQ ID NO: 13. Further, a polypeptide having the second-step oxidation activity and consisting of the amino acid sequence derived from the amino acid sequence represented by any one of SEQ ID NOs: 9, 11, and 13 by deletion, replacement or addition of one or a plurality of amino acids, or consisting of the amino acid sequence having 80% or more identity with the amino acid sequence represented by any one of SEQ ID NOs: 9, 11, and 13, is also illustrated.

Without limitation, in the gene recombinant of the present invention, 30-hydroxy-β-amyrin and 30-hydroxy-11-oxo-β-amyrin can be produced, respectively, mainly using β-amyrin and 11-oxo-β-amyrin as substrates and oxidizing the 30-position by a catalytic activity of CYP72A154 and the like expressed by the CYP72A154 expression vector. In addition, glycyrrhetinic acid can be produced by using 30-hydroxy-11-oxo-β-amyrin as a substrate and further oxidizing the 30-position thereof.

The configuration of the plasmid region in the CYP72A154 expression vector is equivalent to that of the expression vector in the recombinant vector described in the third aspect. The recombinant vector described in Japanese Patent No. 5771846 may also be used.

(3) UGT73P12 Recombinant Vector

The "UGT73P12 recombinant vector" contains a gene encoding a polypeptide having an activity of transferring glucuronic acid to the hydroxy group at the 2-position of the glucuronic acid in an oleanane-type triterpenoid monoglucuronide, that is, UGT73P12 and an active fragment thereof (often referred to herein as "UGT73P12 and the like") and a fragment thereof (often referred to herein as "UGT73P12 gene and the like"). Therefore, in the gene recombinant, UGT73P12 and the like are expressed by the UGT73P12 expression vectors.

Specific examples of the UGT73P12 include, but are not limited to, UGT73P12 derived from *Glycyrrhiza* (*G. uralensis*) consisting of the amino acid sequence represented by SEQ ID NO: 15. Further, a polypeptide having the second-step glycosylation activity and consisting of the amino acid sequence derived from the amino acid sequence represented by SEQ ID NO: 15 by deletion, replacement or addition of one or a plurality of amino acids, or consisting of an amino acid sequence having 80% or more identity with the amino acid sequence represented by SEQ ID NO: 15, is also illustrated.

The configuration of the plasmid region in the UGT73P12 expression vector is equivalent to that of the expression vector in the recombinant vector described in the third aspect. The recombinant vector described in Japanese Patent No. 6344774 may also be used.

(4) CSyGT Expression Vector

Since the "CSyGT expression vector" corresponds to the CSyGT expression vector in the CSyGT recombinant vector described in the third aspect, detailed description thereof will be omitted here.

6-2-2. Gene Recombinant for Producing
Glycyrrhizin

The "gene recombinant for producing glycyrrhetinic acid" of the present invention refers to a transformant into which an expression vector containing at least the set of four enzyme genes is introduced, or a progeny thereof having the set of enzyme genes. Therefore, the basic configuration may be the same as that of the transformant described in the fourth aspect and the progeny thereof, except that the types of the expression vectors included are different. However, since the present invention is a gene recombinant capable of biologically synthesizing glycyrrhizin from β-amyrin in the cell, it is preferably a host capable of biologically synthesizing β-amyrin, which is the starting material in the biosynthetic system, in the cell. The biosynthesis of β-amyrin in the host may be based on an endogenous synthetic system, or on an exogenous synthetic system. Since β-amyrin, which is an oleanane-type triterpenoid, can be biologically synthesized by many plants, the host of the present invention is preferably a plant when based on an endogenous synthetic system. Plant species with high-amyrin synthesis capacity, high fertility, and easy to grow, are preferred. A plant relatively related to *Glycyrrhiza*, that is, a Fabaceae plant is more preferred. For example, a species belonging to the genus *Glycyrrhiza*, a species belonging to the genus Soybean, a species belonging to the genus *Lotus japonicus* and the like may be included. On the other hand, when the biosynthesis of β-amyrin is based on an exogenous synthetic system, the host itself may be a species that cannot biologically synthesize β-amyrin. For example, by introducing an expression vector containing a β-amyrin synthase gene into an yeast, a transformant of the yeast can be used as a host capable of biologically synthesizing B-amyrin in the cell.

According to the present invention, even a host that could not biologically synthesize glycyrrhizin in the past, it becomes able to biologically synthesize glycyrrhizin as a metabolite of β-amyrin, which is used as a starting material.

7. Method for Producing Glycyrrhizin

7-1. Summary

The seventh aspect of the present invention is a method for producing glycyrrhizin. The production method of the present invention is characterized in that glycyrrhizin is produced from β-amyrin by using the gene recombinant for producing glycyrrhizin of the sixth aspect as a biological production system.

According to the production method of the present invention, glycyrrhizin, which was expensive in the past, can be stably obtained and in a large amount without extraction from *Glycyrrhiza*.

7-2. Method

The production method of the present invention comprises a culturing step as an essential step, and "extraction step" as an optional step.

(1) Culturing Step

The "culturing step" in the present aspect may be basically equivalent to the culture step described in the fifth aspect. When the gene recombinant is a plant, a method for culturing a plant under known conditions may be applied. According to the present step, glycyrrhizin is produced in the gene recombinant for producing glycyrrhizin of the sixth aspect.

(2) Extraction Step

"Extraction step" in this aspect may be basically equivalent to the extraction step described in the fifth aspect. If the gene recombinant is a plant, the same method as that for extracting glycyrrhizin from *Glycyrrhiza* can be used.

According to the production method of the present invention, glycyrrhizin can be obtained stably and in a large amount from various gene recombinants, without extraction from *Glycyrrhiza*.

EXAMPLES

The present invention will be described by way of examples below.

Example 1: Isolation of Soy Bean-Derived Cellulose Synthase Analogous Gene Glyma.06G324300

Matured seeds of greenhouse-grown soy bean (*Glycine max*) "Williams 82" variety were collected. Total RNA was prepared by using an RNA extraction reagent, RNeasy Plant Mini Kit (QIAGEN) in accordance with the attached protocol. Using the total RNA (200 ng) obtained, a first-strand cDNA was synthesized by use of QuantiTech Reverse Transcription Kit (QIAGEN) in accordance with the attached protocol. A cycle of PCR was repeated 30 times by use of PrimeSTAR GXL DNA Polymerase (TAKARA BIO INC.) at an annealing temperature of 55° C. and a reaction temperature of 68° C., using the 5-fold diluted first-strand cDNA (1 μL for each) as a template and oligo DNA molecules corresponding to the N terminal and C terminal of the polypeptide estimated from Glyma.06G324300, respectively, as a forward primer (SEQ ID NO: 17) and a reverse primer (SEQ ID NO: 18). Note that 12 nucleotides (AAAAAGCAGGCT) are artificially added to the 5' terminal of the forward primer and 12 nucleotides (AGAAAGCTGGGT) are artificially added to the 5' terminal of the reverse primer, for the reason that the nucleotides are required for nucleotide sequence specific recombination reaction (GATEWAY attBx attP reaction) in cloning into pDONR™221 (Thermo Fisher Technologies). The DNA fragment, which was amplified from seed-derived first-strand cDNA, was cloned to pDONR™221 by the nucleotide sequence specific recombination reaction (GATEWAY attBx attP reaction) using Gateway BP Clonase II Enzyme Mix (Thermo Fisher Technologies). The polynucleotide sequences of the resultant three independent clones were determined. The sequence thus obtained is represented by SEQ ID NO: 2. The polypeptide sequence estimated from the aforementioned sequence is represented by SEQ ID NO: 1.

Example 2: Search for *Glycyrrhiza*-Derived Glyma.06G324300 Homologous Gene Glyma.06G324300 homologous gene was searched as a candidate for Glyma.06G324300 orthologue gene by gene homology search from *Glycyrrhiza* (*Glycyrrhiza uralensis*), which belongs to the same Fabaceae plant as soybean and is known to biologically synthesize glycyrrhizin. Using BLAST homology search function in genome information database of *Glycyrrhiza*, i.e., *Glycyrrhiza uralensis* GDB (http-colon-slash-slash ngs-data-archive.psc.riken.jp/Gur-genome/index.pl), a type of nucleotide sequence Glyur003152s00037491, which may encode a protein having high amino acid identity with Glyma.06G324300, was found. The polypeptide estimated from Glyur003152s00037491 had an amino acid identity of 81% with that of Glyma.06G324300.

Example 3: Isolation of *Glycyrrhiza*-Derived Glyma.06G324300 Homologous Gene Total RNA was prepared from root of *Glycyrrhiza* using RNA extraction reagent, PureLink Plant RNA Reagent (Thermo Fisher Scientific). Using the total RNA (1 μg) obtained, a first-strand cDNA was synthesized by use of SMART RACE cDNA amplification kit (Clontech) in accordance with the attached protocol. A cycle of PCR was repeated 30 times by use of PrimeSTAR Max DNA Polymerase (TAKARA BIO INC.) at an annealing temperature of 55° C. and a reaction temperature of 72° C., using the first-strand cDNA (2 μL) as a template and oligo DNA molecules corresponding to the N terminal and C terminal of the polypeptide estimated from Glyur003152s00037491, respectively, as a forward primer (SEQ ID NO: 19) and a reverse primer (SEQ ID NO: 20). Note that 4 nucleotides (cacc) are artificially added to the 5' terminal of the forward primer, for the reason that the nucleotides are required for cloning into pENTR™/D-TOPO (registered trademark) entry vector (Thermo Fisher Technologies). The DNA fragment, which was amplified, was cloned to pENTR™/D-TOPO entry vector. The nucleotide sequences of the resultant four independent clones were determined. As a result, the nucleotide sequence of Glyma.06G324300 homologous gene of *Glycyrrhiza* thus obtained is represented by SEQ ID NO: 4. The polypeptide sequence estimated from the nucleotide sequence is represented by SEQ ID NO: 3. The amino acid sequence represented by SEQ ID NO: 3 had an identity of 82% with the amino acid sequence represented by SEQ ID NO: 1.

Example 4: Search for *Lotus japonicus*-Derived Glyma.06G324300 Homologous Gene In the same manner as in Example 2, Glyma.06G324300 homologous gene was searched as a candidate for a *Lotus japonicus*-derived Glyma.06G324300 orthologue gene. Using BLAST homology search function in genome information database of *L. japonicus*, i.e., miyakogusa.jp (http-colon-slash-slash www.kazusa.or.jp/lotus/release1/index-.html), a type of nucleotide sequence, Lj3g3v1981230, which may encode a protein having high amino acid identity with Glyma.06G324300, were found. The polypeptide estimated from Lj3g3v1981230 had an amino acid identity of 81.4% with that of Glyma.06G324300.

Example 5: Isolation of *Lotus japonicus*-Derived Glyma.06G324300 Homologous Gene Using the total RNA (1 μg) obtained from *Lotus japonicus*, a first-strand cDNA was synthesized by use of SMART RACE cDNA amplification kit (Clontech) in accordance with the attached protocol. A cycle of PCR was repeated 30 times by use of PrimeSTAR Max DNA Polymerase (TAKARA BIO INC.) at an annealing temperature of 55° C. and a reaction temperature of 72° C., using the first-strand cDNA (2 μL) as a template and oligo DNA molecules corresponding to the N terminal and C terminal of the polypeptide estimated from Lj3g3v1981230, respectively, as a forward primer (SEQ ID NO: 37) and a reverse primer (SEQ ID NO: 38). Note that 4 nucleotides (cacc) are artificially added to the 5' terminal of the forward primer, for the reason that the nucleotides are required for cloning into pENTR™/D-TOPO (registered trademark) entry vector (Thermo Fisher Technologies). The DNA fragment, which was amplified, was cloned to pENTR™/D-TOPO entry vector. The polynucleotide sequences of the resultant two independent clones were determined. As a result, the nucleotide sequence of Glyma.06G324300 homologous gene of *Lotus japonicus* thus obtained is represented by SEQ ID NO: 6. The polypeptide sequence estimated from the nucleotide sequence of SEQ ID NO: 6 is represented by SEQ ID NO: 5. The amino acid sequence represented by SEQ ID NO: 5 had an identity of 82% with the amino acid sequence represented by SEQ ID NO: 1.

Example 6: Construction of Destination Vector for Yeast Expression

In order to investigate the expected transglycosylation activity of Glyma.06G324300 isolated in Examples 1, 3, and 5 and a homologous protein thereof, an expression vector for each protein was constructed using a yeast expression system.

The yeast (*Saccharomyces cerevisiae*) INVScl strain used does not contain endogenous UDP-glucuronic acid, which is to be a glycosyl donor substrate, in the glycosylation reaction expected for the candidate gene product. Therefore, a UDP-glucose dehydrogenase (UGD) gene, which synthesizes UDP-glucuronic acid using UDP-glucose endogenously in yeast as a substrate, was introduced into a destination vector for yeast expression. Specifically, a cycle of PCR was repeated 30 times by use of PrimeSTAR Max DNA Polymerase (TAKARA BIO INC.) at an annealing temperature of 55° C. and a reaction temperature of 72° C., using cDNA of *Arabidopsis thaliana*-derived UGD (AtUGD2) as a template and oligo DNA molecules corresponding to the N terminal and C terminal of the polypeptide, respectively, as a forward primer (SEQ ID NO: 21) and a reverse primer (SEQ ID NO: 22). Note that 15 nucleotides upstream of the cloning position of the destination vector and 4 nucleotides (aaaa), 19 nucleotides in total, are artificially added to the 5' terminal of the polynucleotide represented by SEQ ID NO: 23 (gggggccgcactag) of the forward primer, for the reason that the nucleotides are required for in-fusion cloning. Further, note that 15 nucleotides downstream of the cloning position of the destination vector are added to the 3' terminal of the polynucleotide represented by SEQ ID NO: 24 (atccatcgatactag) of the reverse primer. Destination vector pESC-HIS-GW was produced by introducing Gateway cassette A (Thermo Fisher Technologies) at the SrfI restriction enzyme site in MCS2 of pESC-HIS (registered trademark) yeast expression vector (Agilent Technologies). The Destination vector pESC-HIS-GW was treated with SpeI restriction enzyme, mixed with DNA fragments amplified from cDNA, and the DNA fragment represented by SEQ ID NO: 25 is introduced at MCS1 in pESC-HIS-GW using In-Fusion (registered trademark) HD Cloning Kit (TAKARA BIO INC.), to obtain the destination vector pESC-HIS-AtUGD2-GW.

Example 7: Construction of Yeast Expression Clone

A plasmid (entry clone) having the polynucleotide represented by SEQ ID NO: 2 produced in Example 1 and a destination vector pESC-HIS-AtUGD2-GW produced in Example 6 were mixed with each other and subjected to a nucleotide sequence specific recombination reaction (GATEWAY attLxattR reaction) using Gateway LR ClonaseII Enzyme Mix (Thermo Fisher Technologies) to transfer the DNA fragment represented by SEQ ID NO: 2 to pESC-HIS. In this manner, a yeast expression vector pESC-HIS-AtUGD2-Glyma.06G324300 for a gene represented by SEQ ID NO: 2 was obtained. In the same manner as described above, yeast expression vectors pESC-HIS-AtUGD2-Glyur003152s00037491 and pESC-HIS-AtUGD2-Lj3g3v1981230, respectively for the genes represented by SEQ ID NOs: 4 and 6 produced in Examples 3 and 5, were respectively obtained.

Figure 3:
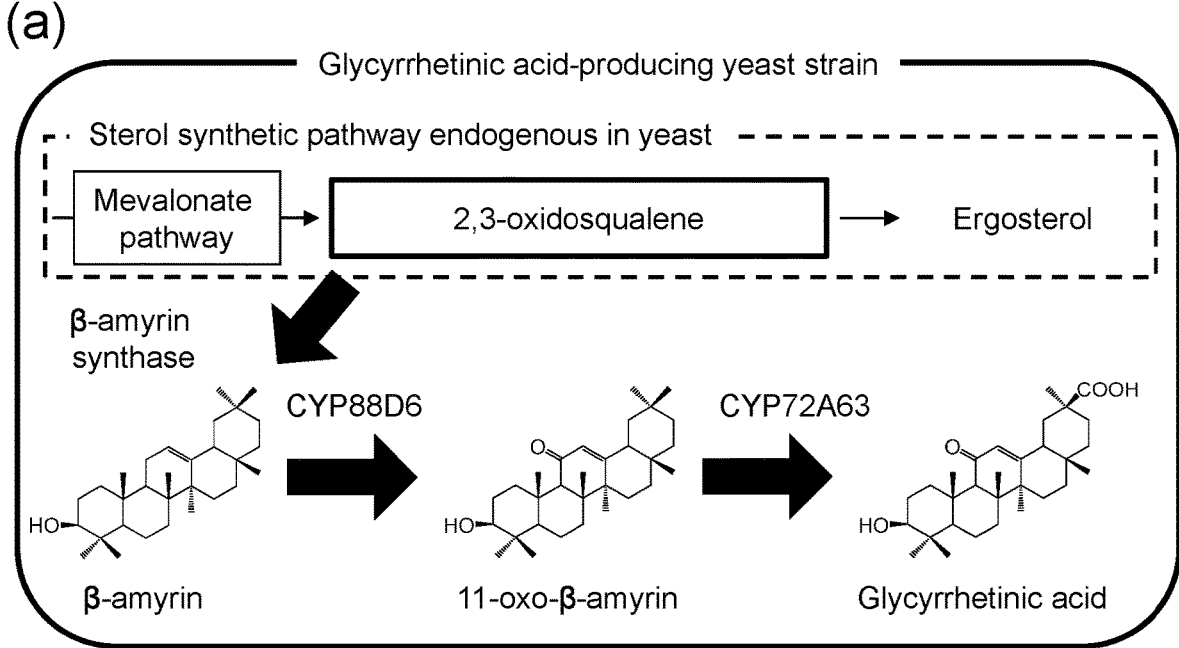
FIG. 3 is a conceptual diagram showing triterpenoid producing yeast strains used for functional analyses of soy bean Glyma.06G324300, and *Glycyrrhiza-* and *Lotus japonicus-*derived Glyma.06G324300 homologous proteins in examples. The yeast strain in (a) can intracellularly produce glycyrrhetinic acid from 2,3-oxidosqualene endogenously in yeast by co-expression of β-amyrin synthase gene (*Lotus japonicus-*derived), CYP88D6 (*Glycyrrhiza-*derived), and CYP72A63 (*M. truncatula-*derived). The yeast strain in (b) can intracellularly produce soyasapogenol B from 2,3-oxidosqualene endogenously in yeast by co-expression of β-amyrin synthase gene (*Lotus japonicus-*derived), CYP93E3 (*Glycyrrhiza-*derived), and CYP72A566 (*Glycyrrhiza-*derived).
Figure 3:
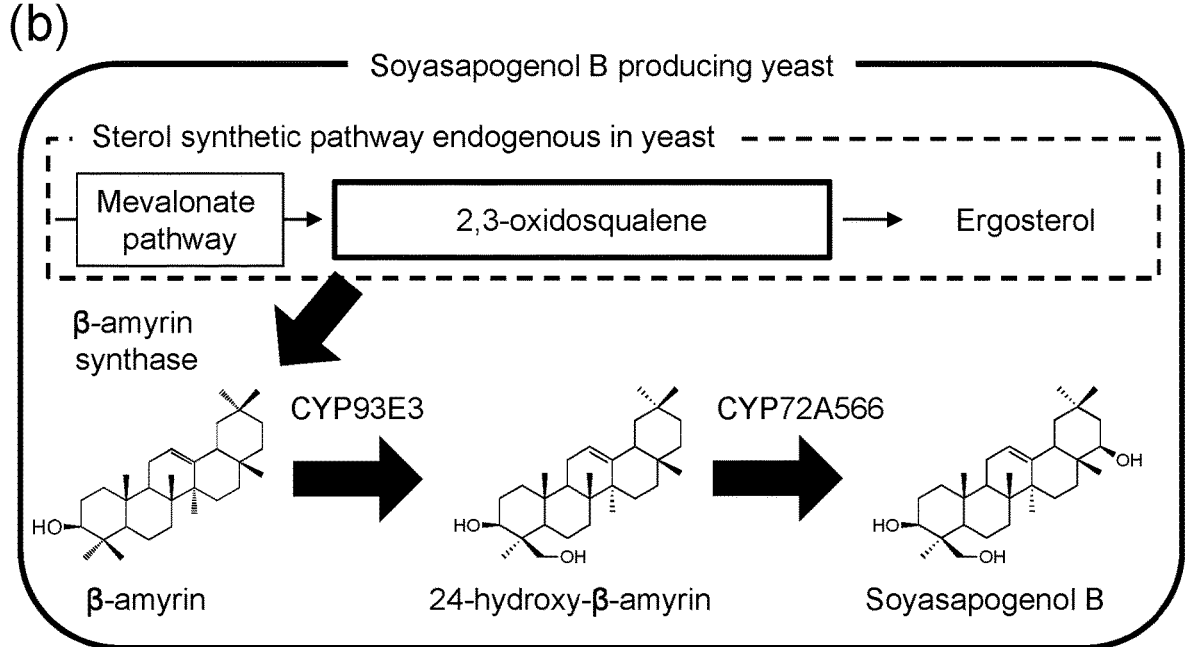

Example 8: Introduction into Glycyrrhetinic Acid and Soyasapogenol B-Producing Yeast Strains To yeast INVScl strain (Thermo Fisher Technologies) (MATa his3D1 leu2 trp1-289 ura3-52 MATAlpha his3D1 leu2 trp1-289 ura3-52), the expression vector pYES3-BAS of the B-amyrin synthase (LjOSC1) gene of *Lotus japonicus*, the co-expression vector pESC-CPR-CYP88D6 of the CYP88D6 gene and the cytochrome P450 reductase (LjCPR1) of *Lotus japonicus*, and the expression vector pDEST52-CYP72A63 of the CYP72A63 gene which is the *M. truncatula* ortholog of the *Glycyrrhiza* CYP72A154 gene were introduced, and co-expressed, to obtain a glycyrrhetinic acid-producing yeast strain (FIG. 3(*a*)). At the same time, the expression vector pYES3-BAS of the β-amyrin synthase gene, the co-expression vector pESC-CPR-CYP93E3 of the CYP93E3 gene and the cytochrome P450 reductase (LjCPR1) of *Lotus japonicus*, and the expression vector pDEST52-CYP72A566 of the CYP72A566 gene were introduced, and co-expressed, to obtain soyasapogenol B-producing yeast (FIG. 3(*b*)). pESC-HIS-AtUGD2-

Glyma.06G324300, pESC-HIS-AtUGD2-Glyur003152s00037491, and pESC-HIS-AtUGD2-Lj3g3v1981230, obtained in Example 7, were respectively introduced into these yeast strains. As a negative control, pESC-HIS-AtUGD2 corresponding to an empty vector was introduced into the glycyrrhetinic acid-producing yeast strain. The yeast was transformed by use of Frozen-EZ Yeast Transformation II (Zymo Research) in accordance with the attached protocol.

Example 9: In Vivo Enzyme Assay Using Recombinant Yeast

Using 1 mL of Yeast nitrogen base (YNB) medium (-Trp/-Leu/-Ura/-His) containing 2% glucose, a glycyrrhetinic acid-producing yeast strain having pESC-HIS-AtUGD2-Glyma.06G324300, pESC-HIS-AtUGD2-Glyur003152s00037491, pESC-HIS-AtUGD2-Lj3g3v1981230, or negative control pESC-HIS-AtUGD2, obtained in Example 8, was cultured while shaking at 30° C., 200 rpm for 24 hours. Thereafter, the culture solution was centrifuged at 3,000 g, 4° C. for 5 minutes to obtain a yeast cell pellet. The yeast cell pellet thus obtained was suspended in 1 mL of Yeast nitrogen base (YNB) medium (-Trp/-Leu/-Ura/-His), thereafter centrifuged again at 3,000 g, 4° C. for 5 minutes to obtain a yeast cell pellet. The yeast cell pellet thus obtained was suspended in 5 mL of Yeast nitrogen base (YNB) medium (-Trp/-Leu/-Ura/-His) containing 2% galactose, and cultured while shaking at 30° C., 200 rpm for 5 days. Thereafter, a volume equivalent to 1 mL of glass beads (SIGMA) and 4 mL of 1-butanol were added to the culture solution. In order to fracture yeast cells, the culture solution was vigorously stirred with a strong shaker for 30 minutes, and the resultant solution was centrifuged at 10,000 g, 4° C. for 10 minutes, thereafter the supernatant was recovered as a yeast metabolite extract. To the remaining solution, 4 mL of 1-butanol was added newly and stirred again for 30 minutes, the resultant solution was centrifuged at 10,000 g, 4° C. for 10 minutes, and the supernatant was extracted. As a result, a metabolite extract derived from the glycyrrhetinic acid-producing yeast strain and expressing the polypeptide represented by SEQ ID NO: 1 (Glyma.06G324300) (sample A), a metabolite extract derived from the glycyrrhetinic acid-producing yeast strain and expressing the polypeptide represented by SEQ ID NO: 3 (Glyur003152s00037491) (sample B), a metabolite extract derived from the glycyrrhetinic acid-producing yeast strain and expressing the polypeptide represented by SEQ ID NO: 5 (Lj3g3v1981230) (sample C), and a metabolite extract derived from the glycyrrhetinic acid-producing yeast strain with an empty vector alone and expressing no gene (sample D) were obtained.

In the same manner, the soyasapogenol B-producing yeast strain having pESC-HIS-AtUGD2-Glyma.06G324300, pESC-HIS-AtUGD2-Glyur003152s00037491, pESC-HIS-AtUGD2-Lj3g3v1981230, or negative control pESC-HIS-AtUGD2 was also cultured, and the metabolite was extracted. As a result, a metabolite extract derived from the soyasapogenol B-producing yeast strain expressing the polypeptide represented by SEQ ID NO: 1 (Glyma.06G324300) (sample E), a metabolite extract derived from the soyasapogenol B-producing yeast strain expressing the polypeptide represented by SEQ ID NO: 3 (Glyur003152s00037491) (sample F), a metabolite extract derived from the soyasapogenol B-producing yeast strain expressing the polypeptide represented by SEQ ID NO: 5 (Lj3g3v1981230) (sample G), and a metabolite extract derived from the soyasapogenol B-producing yeast strain with an empty vector alone and expressing no gene (sample H) were obtained.

Example 10: Analysis of Yeast Metabolite Extract

Samples A, B, C, and D, as well as samples E, F, G, and H, obtained in Example 9, were evaporated using a rotary evaporator. The precipitates were suspended in 300 μL of methanol and filtered using Millex-GV, 0.22 μm, PVDF, 4 mm (Merck & Co., Inc.), and used as samples for LC-MS analysis.

LC-MS analysis was performed by ACQUITY UPLC/TQD-MS (Waters Corp.). As a column, UPLC HSS C18 (2.1 mm×150 mm, 1.7 μm) (Waters Corp.) was used. Analysis was made while supplying solvents containing 0.1% acetic acid-acetonitrile: 0.1% acetic acid-water=30:70 (0 to 5 minutes), 40:60 to 100:0 (5 to 28 minutes), and 100:0 (28 to 31.5 minutes) at a flow rate of 0.2 mL/minute. MS was analyzed using SIM mode with the following parameters: m/z of each compound, glycyrrhetinic acid=469.7, glycyrrhetinic acid monoglycoside=631.9, glycyrrhetinic acid monoglucuronide=645.8, glycyrrhizin=821.9. The metabolite was identified by comparing LC retention times and MS spectra using samples prepared by dissolving commercially available glycyrrhetinic acid monoglucuronide and glycyrrhizin in methanol to a concentration of 1 μM as standards.

Figure 4:
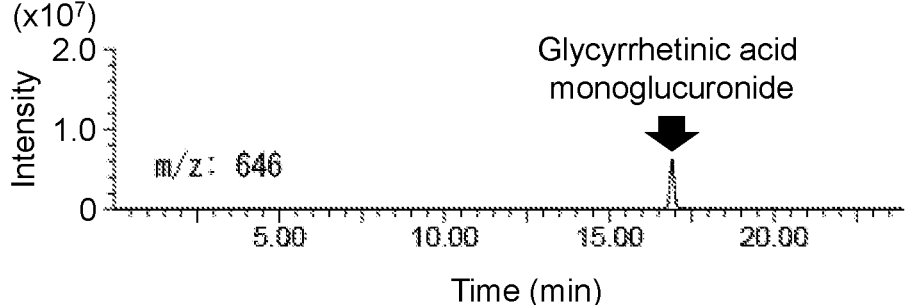
FIG. 4 shows metabolite analysis results of glycyrrhetinic acid producing yeast, into which Glyma.06G324300 and homologous gene were introduced. Sample A in (a) shows detection results of glycyrrhetinic acid monoglucuronide generated by expressing soy bean-derived Glyma.06G324300 in glycyrrhetinic acid-producing yeast: Sample B in (b) shows detection results of glycyrrhetinic acid monoglucuronide generated by expressing *Glycyrrhiza-*derived Glyur003152s00037491 in glycyrrhetinic acid-producing yeast: Sample C in (c) shows detection results of glycyrrhetinic acid monoglucuronide generated by expressing *Lotus japonicus-*derived Lj3g3v1981230 in glycyrrhetinic acid-producing yeast. The peak pointed by a solid arrow shows glycyrrhetinic acid monoglucuronide. Sample D in (d) shows detection results in glycyrrhetinic acid-producing yeast, into which an empty vector was introduced as a negative control.
Figure 4:
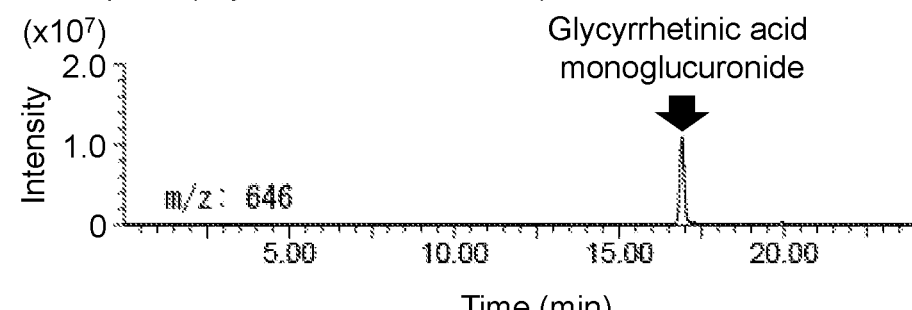
Figure 4:
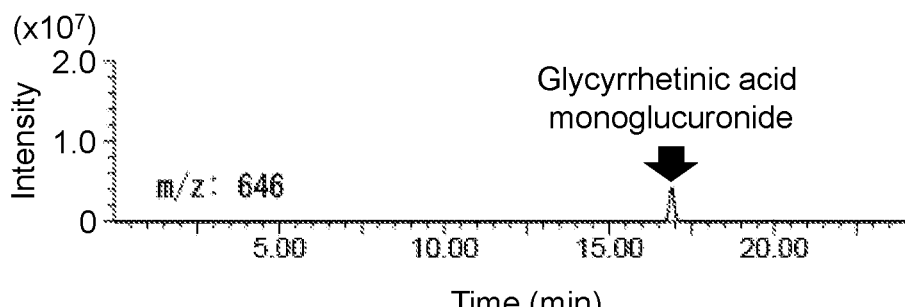
Figure 4:
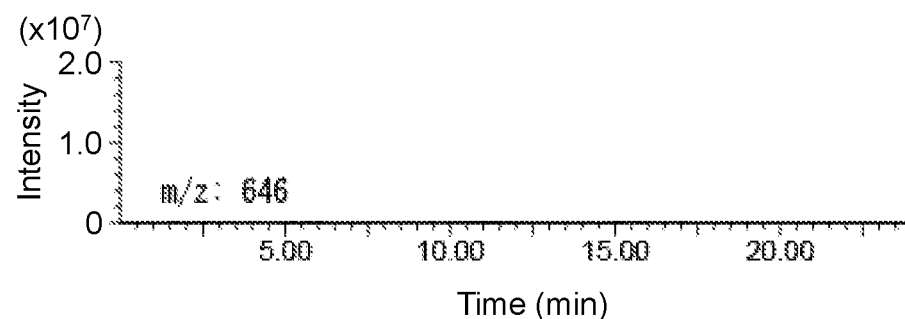
Figure 5:
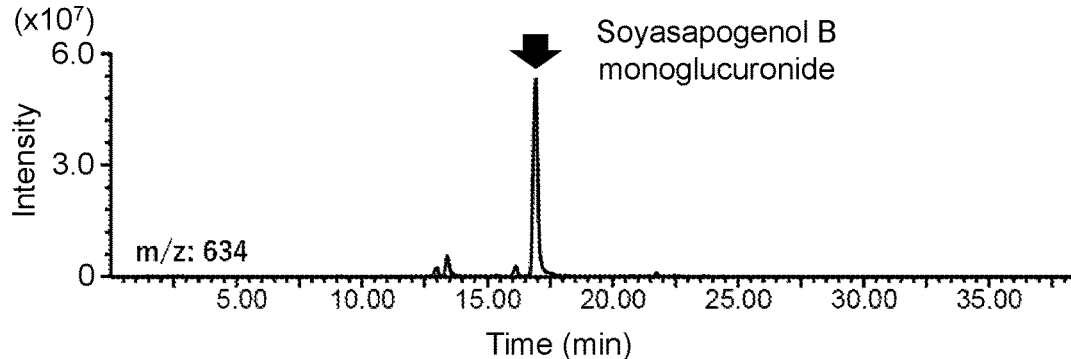
FIG. 5 shows metabolite analysis results of soyasapogenol B producing yeast, into which Glyma.06G324300 and homologous gene were introduced. Sample E in (a) shows detection results of soyasapogenol B monoglucuronide generated by expressing soy bean-derived Glyma.06G324300 in soyasapogenol B-producing yeast: Sample F in (b) shows detection results of soyasapogenol B monoglucuronide generated by expressing *Glycyrrhiza-*derived Glyur003152s00037491 in soyasapogenol B-producing yeast: Sample G in (c) shows detection results of soyasapogenol B monoglucuronide generated by expressing *Lotus japonicus-*derived Lj3g3v1981230 in soyasapogenol B-producing yeast. The peak pointed by a solid arrow shows soyasapogenol B monoglucuronide. Sample H in (d) shows detection results in soyasapogenol B-producing yeast in which an empty vector was introduced as a negative control.
Figure 5:
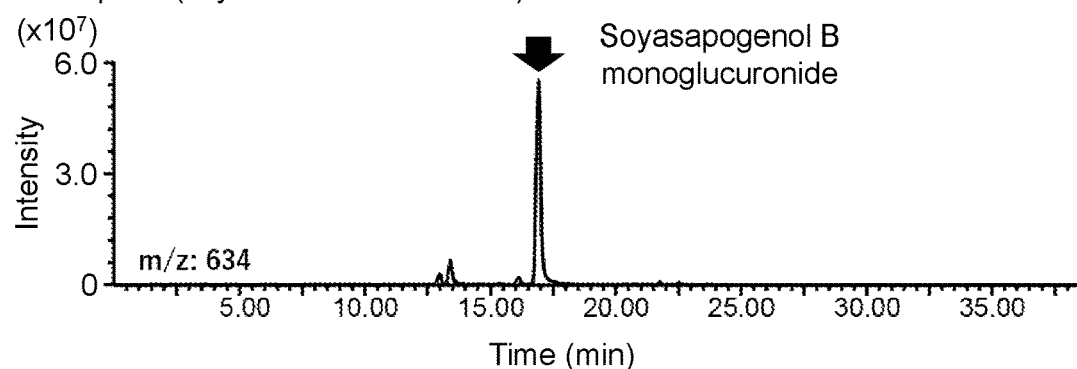
Figure 5:
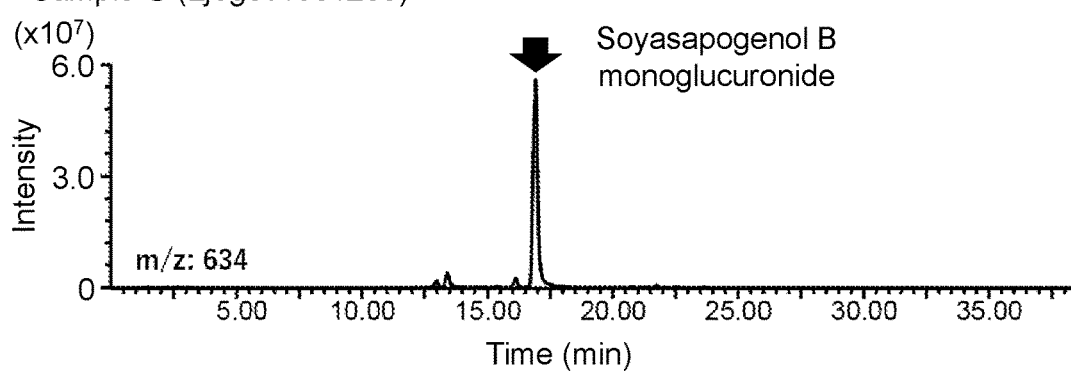
Figure 5:
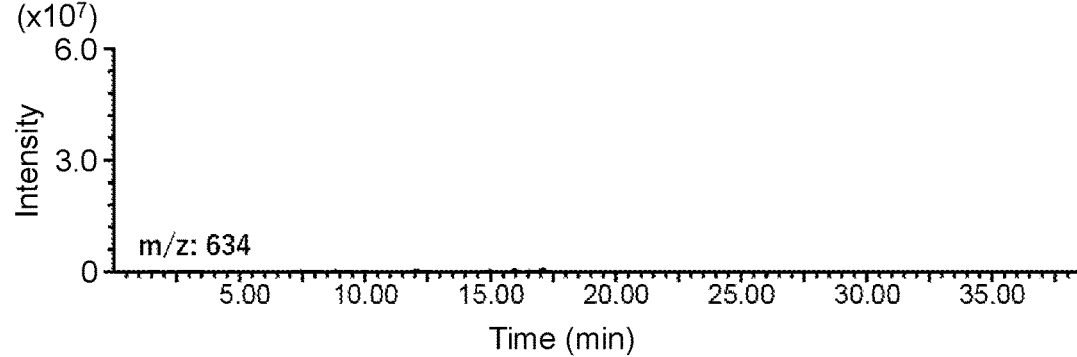
Figure 6:
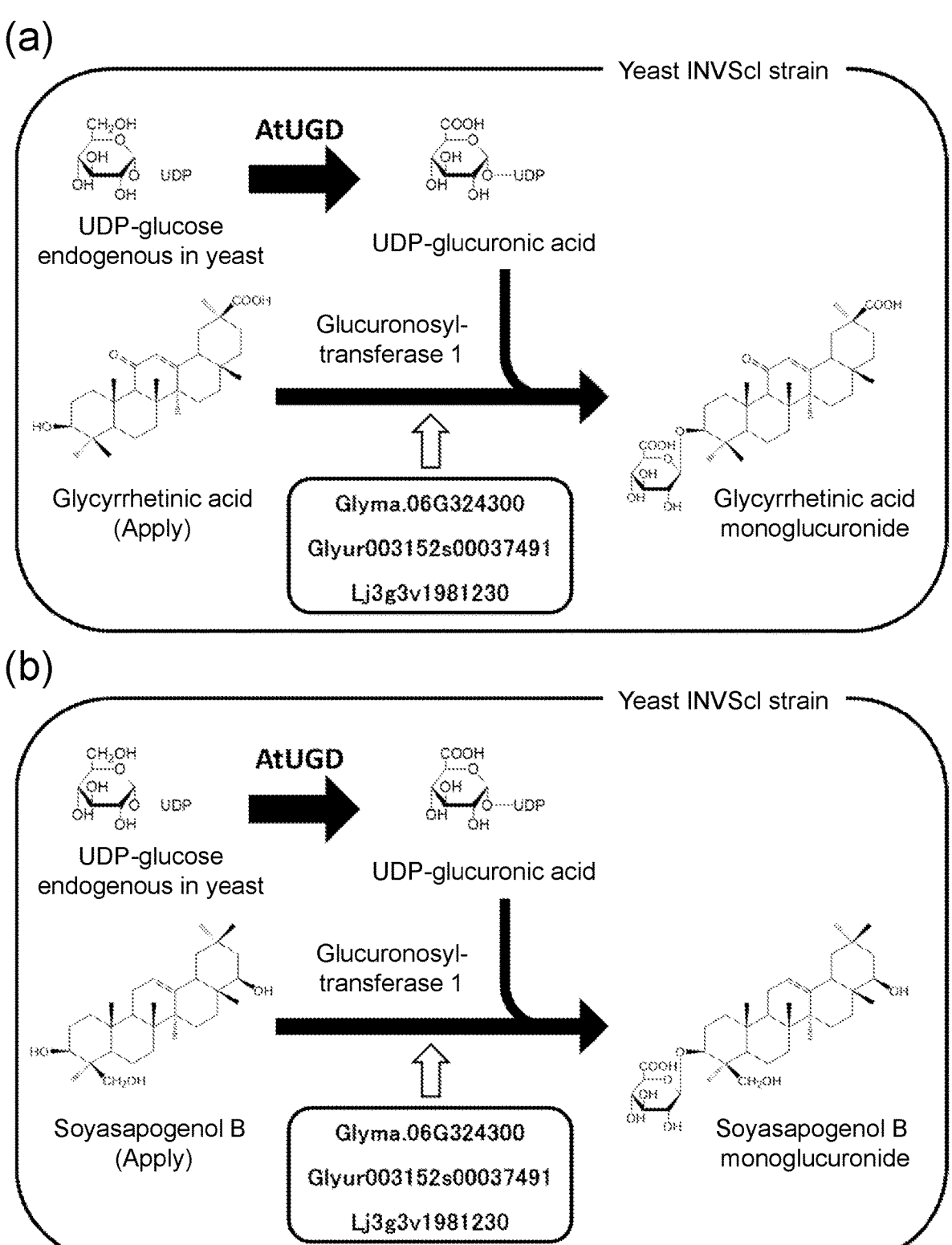
FIG. 6 shows an overview of the substrate feeding experiment. *Arabidopsis thaliana* UDP-glucose dehydrogenase (AtUGD), Glyma.06G324300, and homologous genes thereof were co-expressed in the yeast to intracellularly supply UDP-glucuronic acid which is a sugar donor substrate. (a) shows a conversion reaction to monoglucuronide when glycyrrhetinic acid was added to the yeast culture, and (b) shows a conversion reaction to monoglucuronide when soyasapogenol B was added to the yeast culture.

The results are shown in FIG. 4 and FIG. 5.

FIG. 4 shows the results of the enzymatic activity of Glyma.06G324300 or homologues thereof when glycyrrhetinic acid and glucuronic acid were used as substrates. A peak (solid arrow) corresponding to glycyrrhetinic acid monoglucuronide was detected from sample A in (a). The retention time and mass spectrum of this peak satisfactorily coincided with those of glycyrrhetinic acid monoglucuronide. Similarly, a peak (solid arrow) corresponding to glycyrrhetinic acid monoglucuronide was detected from sample B in (b) and sample C in (c). The retention time and mass spectrum of each peak satisfactorily coincided with those of glycyrrhetinic acid monoglucuronide. In contrast, from sample D in (d) which is a negative control, a peak corresponding to glycyrrhetinic acid monoglucuronide was not detected.

FIG. 5 shows the results of the enzymatic activity of Glyma.06G324300 or homologues thereof when soyasapogenol B and glucuronic acid were used as substrates. A peak (solid arrow) corresponding to soyasapogenol B monoglucuronide was detected from sample E in (a). A peak (solid arrow) corresponding to soyasapogenol B monoglucuronide was also detected from sample F in (b) and sample G in (c). The retention time and mass spectrum of each peak satisfactorily coincided with those of soyasapogenol B monoglucuronide. In contrast, from sample H in (d) which is a negative control, a peak corresponding to soyasapogenol B monoglucuronide was not detected.

Example 11: Preparation of Transformed Yeast for Substrate Feeding Assay pESC-HIS-AtUGD2-Glyma.06G324300, pESC-HIS-AtUGD2-Glyur003152s00037491, and pESC-HIS-AtUGD2-Lj3g3v1981230, obtained in Example 8, were respectively introduced into the yeast INVScl strains. As a negative control, pESC-HIS-AtUGD2 corresponding to an empty vector was introduced into the same yeast INVScl strain. The yeast was transformed by use of Frozen-EZ Yeast Transformation II (Zymo Research) in accordance with the attached protocol.

Example 12: Substrate Feeding Assay Using Recombinant Yeast

Using 2 mL of Yeast nitrogen base (YNB) medium (-His) containing 2% glucose, a transformed yeast having pESC-HIS-AtUGD2-Glyma.06G324300, pESC-HIS-AtUGD2-Glyur003152s00037491, pESC-HIS-AtUGD2-Lj3g3v1981230, or negative control pESC-HIS-AtUGD2, obtained in Example 11, was cultured while shaking at 30° C., 200 rpm for 24 hours. Thereafter, the culture solution was centrifuged at 3,000 g, 4° C. for 5 minutes to obtain a yeast cell pellet. The yeast cell pellet thus obtained was suspended in 2 mL of Yeast nitrogen base (YNB) medium (-His), thereafter centrifuged again at 3,000 g, 4° C. for 5 minutes to obtain a yeast cell pellet. The yeast cell pellet thus obtained was suspended in 10 mL of Yeast nitrogen base (YNB) medium (-His) containing 2% galactose, and divided in equal halves, 5 mL each. Glycyrrhetinic acid at a final concentration of 5 μM was added to one sample, and soyasapogenol B at a final concentration of 5 μM was added to the other sample (FIG. 4). Thereafter, they were cultured while shaking at 30° C., 200 rpm for 10 days. A volume equivalent to 1 mL of glass beads (SIGMA) and 4 mL of 1-butanol were added to the culture solution. In order to fracture yeast cells, the culture solution was vigorously stirred with a strong shaker for 30 minutes to fracture yeast cells, the resultant solution was centrifuged at 10,000 g, 4° C. for 10 minutes, and then the supernatant was recovered as a yeast feeding assay extract. To the remaining solution, 4 mL of 1-butanol was added newly and extracted again. As a result, a feeding assay extract prepared by adding glycyrrhetinic acid to the transformed yeast expressing the polypeptide represented by SEQ ID NO: 1 (Glyma.06G324300) (sample I), a feeding assay extract prepared by adding soyasapogenol B to the transformed yeast expressing the polypeptide represented by SEQ ID NO: 1 (Glyma.06G324300) (sample M), a feeding assay extract prepared by adding glycyrrhetinic acid to the transformed yeast expressing the polypeptide represented by SEQ ID NO: 3 (Glyur003152s00037491) (sample J), a feeding assay extract prepared by adding soyasapogenol B to the transformed yeast expressing the polypeptide represented by SEQ ID NO: 3 (Glyur003152s00037491) (sample N), a feeding assay extract prepared by adding glycyrrhetinic acid to the transformed yeast expressing the polypeptide represented by SEQ ID NO: 5 (Lj3g3v1981230) (sample K), a feeding assay extract prepared by adding soyasapogenol B to the transformed yeast expressing the polypeptide represented by SEQ ID NO: 5 (Lj3g3v1981230) (sample O), a feeding assay extract prepared by adding glycyrrhetinic acid to the transformed yeast with an empty vector alone and expressing no gene (sample L), and a feeding assay extract prepared by adding soyasapogenol B to the transformed yeast with an empty vector alone and expressing no gene (sample P) were obtained.

Example 13: Analysis of Substrate Feeding Assay Extract

Samples I, J, K, L, M, N, O, and P obtained in Example 12 were evaporated using a rotary evaporator. The precipitates were suspended in 300 μL of methanol and filtered using Millex-GV, 0.22 μm, PVDF, 4 mm (Merck & Co., Inc.), and used as samples for LC-MS analysis.

LC-MS analysis was analyzed in the same manner as in Example 10, using SIM mode for MS, with the following parameters: for sample I, J, K, and L, m/z of each compound, glycyrrhetinic acid=469.7, glycyrrhetinic acid monoglycoside=631.9, glycyrrhetinic acid monoglucuronide=645.8, glycyrrhizin=821.9; for sample M, N, O, and P, m/z of each compound, soyasapogenol B=457.8, soyasapogenol B monoglycoside=619.8, soyasapogenol B monoglucuronide=633.8, soyasapogenol B diglucuronide=809.9. The metabolite was identified by comparing LC retention times and MS spectra using samples prepared by dissolving commercially available glycyrrhetinic acid monoglucuronide, glycyrrhizin, and soyasapogenol B monoglucuronide in methanol to a concentration of 1 μM as standards.

Figure 7:
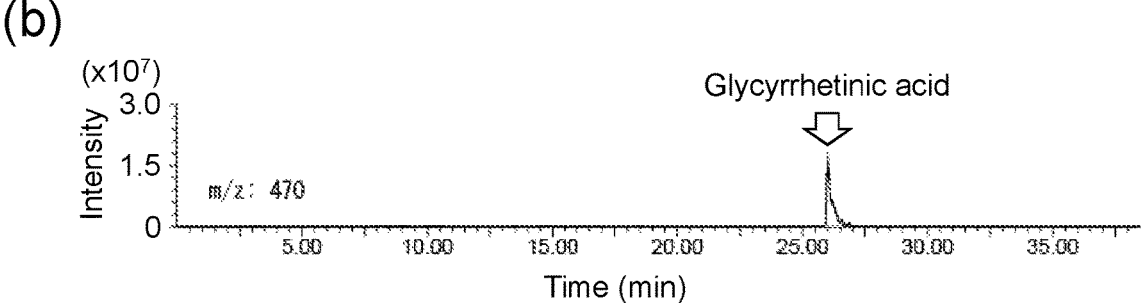
FIG. 7 shows metabolite analysis results in soybean-derived Glyma.06G324300-introduced yeast, to which glycyrrhetinic acid was fed. (a) is a conceptual diagram showing envisaged conversion reactions to glycyrrhetinic acid monoglucuronide when Glyma.06G324300 is used. (b) shows detection results of glycyrrhetinic acid before conversion. The peak pointed by an open arrow shows glycyrrhetinic acid. (c) shows detection results of glycyrrhetinic acid monoglucuronide generated by Glyma.06G324300. The peak pointed by a solid arrow shows glycyrrhetinic acid monoglucuronide.
Figure 7:
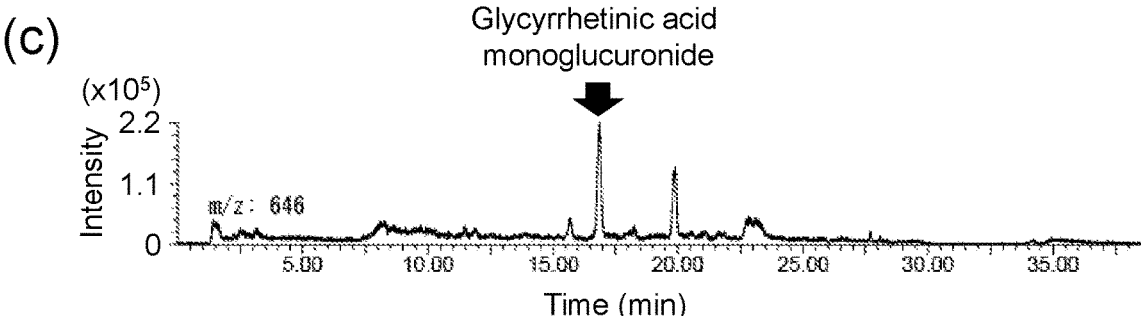

The results of using glycyrrhetinic acid as a sugar acceptor substrate are shown in FIG. 7 to FIG. 10. FIG. 7 shows results of substrate feeding assay in sample I. A peak (open arrow) corresponding to glycyrrhetinic acid as sugar acceptor substrate was detected from (b). In addition, a peak (solid arrow) conceivably derived from glycyrrhetinic acid, to which a single glucuronic acid molecule was added, was detected from (c). The retention time and mass spectrum of this peak satisfactorily coincided with those of glycyrrhetinic acid monoglucuronide.

Figure 8:
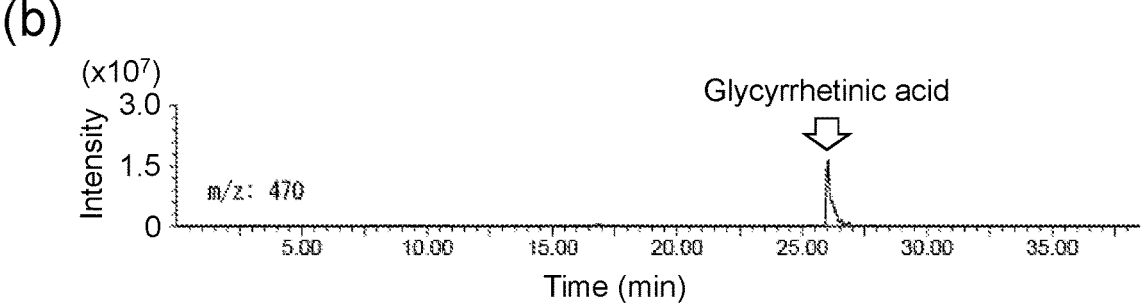
FIG. 8 shows metabolite analysis results in *Glycyrrhiza-*derived Glyur003152s00037491-introduced yeast, to which glycyrrhetinic acid was fed. (a) is a conceptual diagram showing envisaged conversion reactions to glycyrrhetinic acid monoglucuronide when Glyur003152s00037491 is used. (b) shows detection results of glycyrrhetinic acid before conversion. The peak pointed by an open arrow shows glycyrrhetinic acid. (c) shows detection results of glycyrrhetinic acid monoglucuronide generated by Glyur003152s00037491. The peak pointed by a solid arrow shows glycyrrhetinic acid monoglucuronide.
Figure 8:
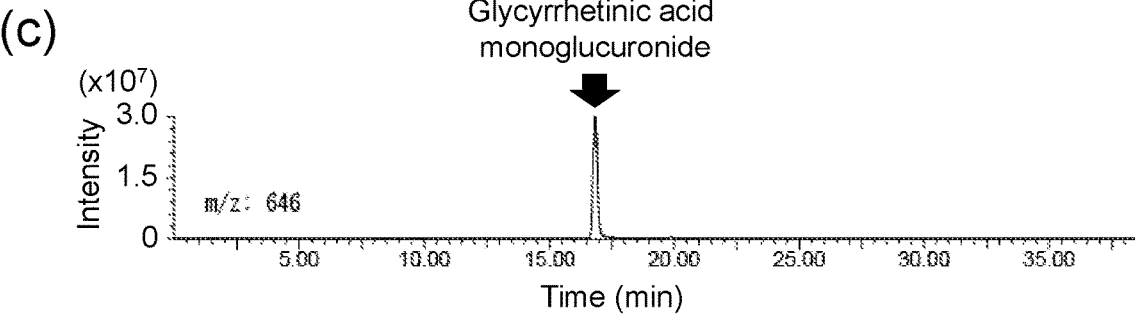
Figure 9:
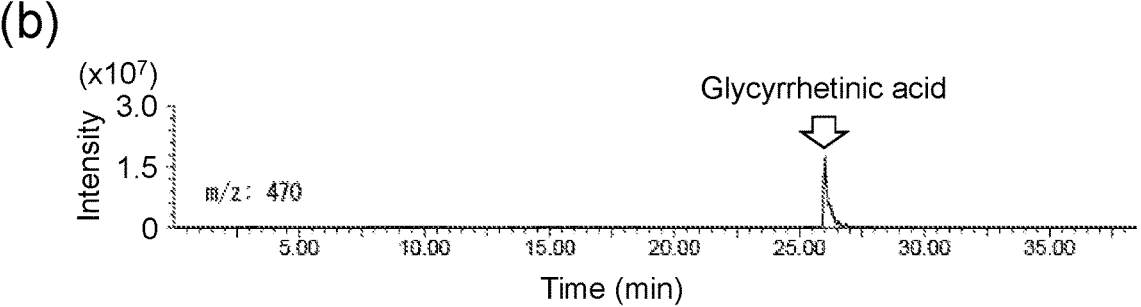
FIG. 9 shows metabolite analysis results in *Lotus japonicus-*derived Lj3g3v1981230-introduced yeast, to which glycyrrhetinic acid was fed. (a) is a conceptual diagram showing envisaged conversion reactions to glycyrrhetinic acid monoglucuronide when Lj3g3v1981230 is used. (b) shows detection results of glycyrrhetinic acid before conversion. The peak pointed by an open arrow shows glycyrrhetinic acid. (c) shows detection results of glycyrrhetinic acid monoglucuronide generated by Lj3g3v1981230. The peak pointed by a solid arrow shows glycyrrhetinic acid monoglucuronide.
Figure 9:
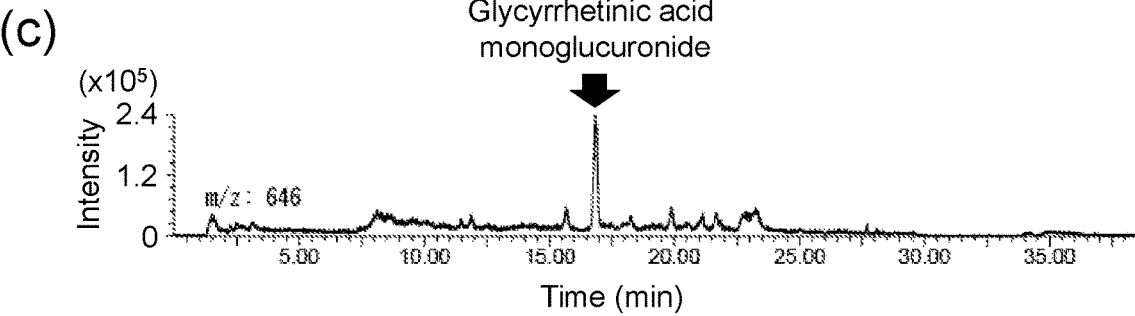

As shown in (b) and (c), respectively, peaks corresponding to glycyrrhetinic acid (open arrow) and glycyrrhetinic acid monoglucuronide (solid arrow) were detected from sample J shown in FIG. 8 and from sample K shown in FIG. 9. The retention time and mass spectrum of each peak satisfactorily coincided with those of glycyrrhetinic acid monoglucuronide.

Figure 10:
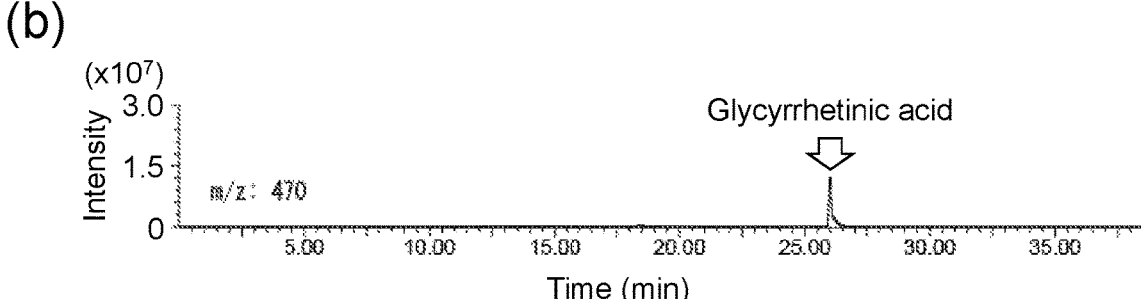
FIG. 10 shows metabolite analysis results in the empty vector-introduced yeast, to which glycyrrhetinic acid was fed, as the negative controls of FIGS. 7 to 9. (a) is a conceptual diagram showing envisaged conversion reactions to glycyrrhetinic acid monoglucuronide when the empty vector is used. It is expected that no glycyrrhetinic acid monoglucuronide is produced due to lack of enzyme activity. (b) shows detection results of glycyrrhetinic acid before reaction. The peak pointed by an open arrow shows glycyrrhetinic acid. (c) shows detection results of glycyrrhetinic acid monoglucuronide after reaction. The peak pointed by a solid arrow shows glycyrrhetinic acid monoglucuronide. A dash line arrow shows a position at which the peak was generated when glycyrrhetinic acid monoglucuronide was produced.
Figure 10:
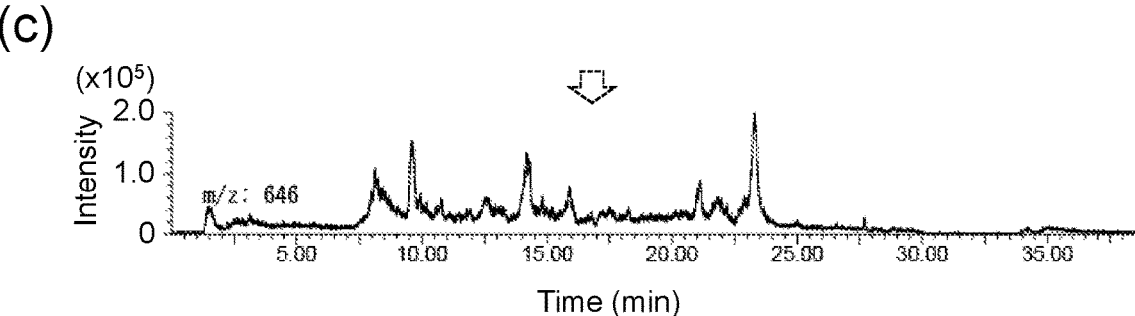

On the other hand, for sample L of a negative control shown in FIG. 10, a peak (open arrow) corresponding to glycyrrhetinic acid as sugar acceptor substrate was detected in (b), but no peak was detected at the position (dash line arrow) corresponding to glycyrrhetinic acid monoglucuronide in (c).

Figure 11:
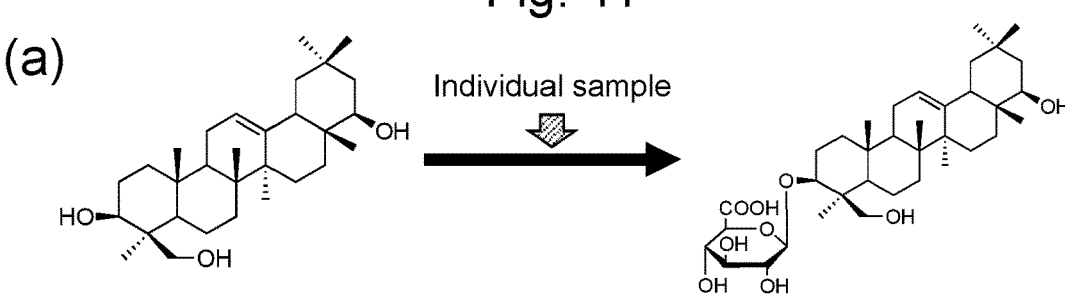
FIG. 11 shows metabolite analysis results in Glyma.06G324300 and its homologous gene-introduced yeast, to which soyasapogenol B was fed. (a) is a conceptual diagram showing envisaged conversion reactions from soyasapogenol B to soyasapogenol B monoglucuronide. (b) shows detection results of soyasapogenol B monoglucuronide generated by soy bean-derived Glyma.06G324300. The peak pointed by a solid arrow shows soyasapogenol B monoglucuronide. (c) shows detection results of soyasapogenol B monoglucuronide generated by *Glycyrrhiza-*derived Glyur003152s00037491. The peak pointed by a solid arrow shows soyasapogenol B monoglucuronide. (d) shows detection results of soyasapogenol B monoglucuronide generated by *Lotus japonicus-*derived Lj3g3v1981230. The peak pointed by a solid arrow shows soyasapogenol B monoglucuronide. (e) shows negative controls of (b) to (d) described above.
Figure 11:
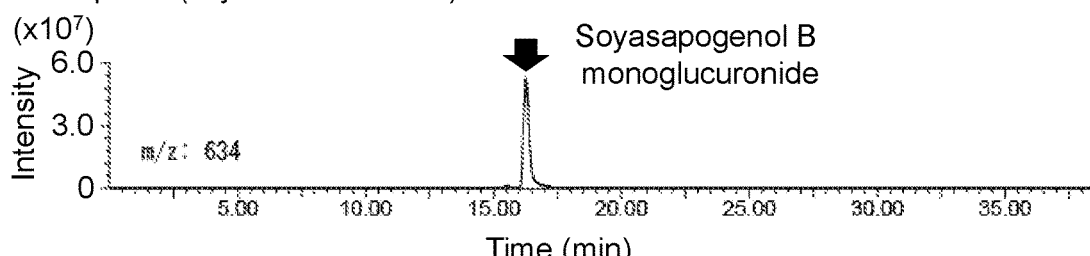
Figure 11:
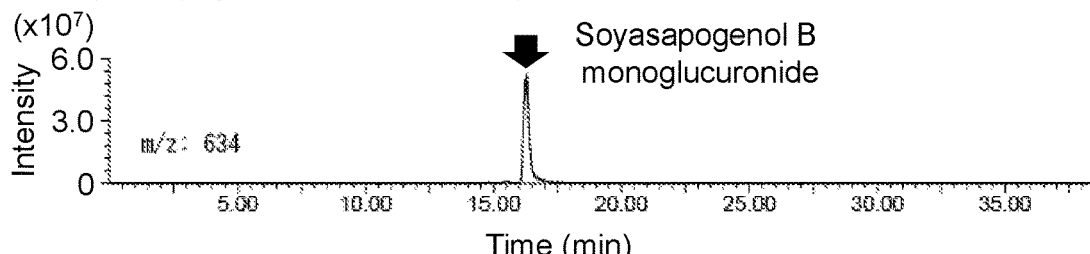
Figure 11:
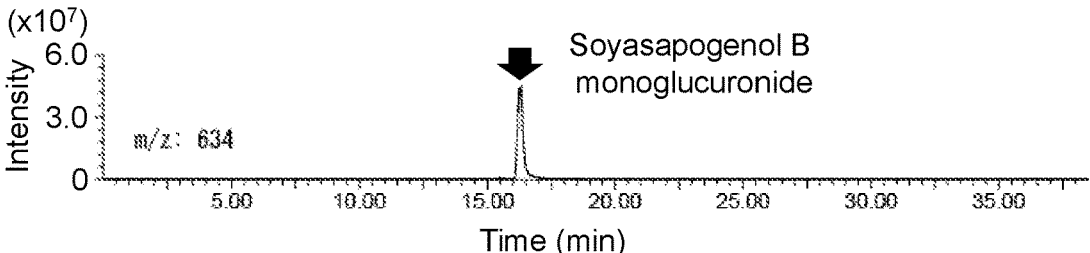
Figure 11:
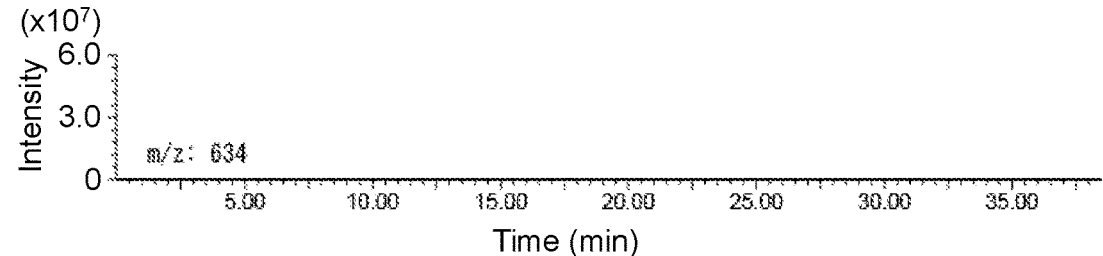

Results of substrate feeding assay using soyasapogenol B as a sugar acceptor substrate are shown in FIG. 11. A peak (solid arrow) corresponding to soyasapogenol B monoglucuronide which is prepared by adding a single glucuronic acid molecule to soyasapogenol B was detected for each of sample M containing soy bean-derived Glyma.06G324300 shown in (b), sample N containing *Glycyrrhiza*-derived Glyur003152s00037491 shown in (c), and sample O containing *L. japonicus*-derived Lj3g3v1981230 shown in (d). The retention time and mass spectrum of the peak satisfactorily coincided with those of soyasapogenol B monoglucuronide. In contrast, from sample P which is a negative control shown in (e), a peak corresponding to soyasapogenol B monoglucuronide was not detected.

The aforementioned results and results obtained in Example 10 show that the aforementioned novel soy bean-derived enzyme Glyma.06G324300 obtained in Example 1, the novel *Glycyrrhiza*-derived enzyme Glyur003152s00037491 obtained in Example 3, and the novel *Lotus japonicus*-derived enzyme Lj3g3v1981230 obtained in Example 5 have a glucuronic acid transfer activity 1 which converts glycyrrhetinic acid to glycyrrhetinic acid monoglucuronide by transferring glucuronic acid to the hydroxy group at the 3-position of the glycyrrhetinic acid. It is also demonstrated that they have glucuronic acid transfer activity 1 which converts soyasapogenol B into soyasapogenol B monoglucuronide by transferring glucuronic acid to the hydroxy group at the 3-position of the soyasapogenol B. Accordingly, the novel enzyme thus obtained was identified as glucuronosyltransferase 1 which transfers glucuronic acid to the hydroxy group at the 3-position of an oleanane-type triterpenoid.

Example 14: Isolation of *Lotus japonicus* Glyma.06G324300 Homologous Gene Loss-of-Function Mutant Based on the sequence information of *Lotus japonicus* gene and protein, and their expression database, *Lotus* Base (https-colon-slash-slash_lotus.au.dk/), mutant lineages having LORE insertion in Lj3g3v1981230 were searched. As a result, 19 lineages were hit. Based on the position of LORE1 insertion in Lj3g3v1981230 and the number of LORE1 insertion in other genes, 2 lineages (30006020, 30115796) were selected from these lineages, and seeds were obtained from a distributor (Aarhus University, Denmark). The seeds were sown, genomic DNA was extracted from some of the unfolded cotyledons, and insertion of LORE1 into Lj3g3v1981230 was confirmed by PCR. A cycle of PCR was repeated 25 times by use of GoTaq (registered trademark) Colorless Master Mix (Promega Corporation) at an annealing temperature of 60° C. and a reaction temperature of 72° C. For PCR, forward primers (30006020 represented by SEQ ID NO: 26, 30115796 represented by SEQ ID NO: 28) and reverse primers (30006020 represented by SEQ ID NO: 27, 30115796 represented by SEQ ID NO: 29) and P2 primer (SEQ ID NO: 30) were used.

Example 15: Triterpenoid Saponin Composition Analysis of Glyma.06G324300 Homologous Gene Loss-of-Function Mutant of *Lotus japonicus*

Whole plants of Glyma.06G324300 homologous gene loss-of-function mutant lineages of *Lotus japonicus* (30006020, 30115796), after 1 month since they had been seeded in Example 14, were freeze-dried, and then 10 times the dry weight of 80% methanol was added, shaken at room temperature for 1 hour, and centrifuged at 15 krpm for 5 minutes. The supernatant obtained by centrifugation was cleaned using a membrane filter with a pore size of 0.45 μm (GL Chromatodisc 4P, GL SCIENCES), and 2 μL of each extract was subjected to LC-PDA/MS/MS analysis. The apparatuses used were Ultimate 3000SD HPLC/LTQ orbitrap discovery MS (both manufactured by Thermo Fisher Scientific). The extracts were applied to a reverse phase column (C30, Develosil C30-UG-3, Nomura Chemical Co., Ltd.), and saponins were eluted by a linear gradient (20 to 80%/60 min) of acetonitrile containing 0.1% (v/v) formic acid at a flow rate of 0.15 ml/min. The eluate was detected by UV absorption and mass spectrometry (orbitrap-type for parent ion, and ion trap type for fragment ion). The eluate vaporized and positively ionized by the electrospray ionization method was injected in a mass spectrometer. Soyasaponin Bb (m/z=943.52) was used as a sample for analysis, and each saponin molecule was annotated by fragment pattern by MS/MS analysis.

Figure 2:
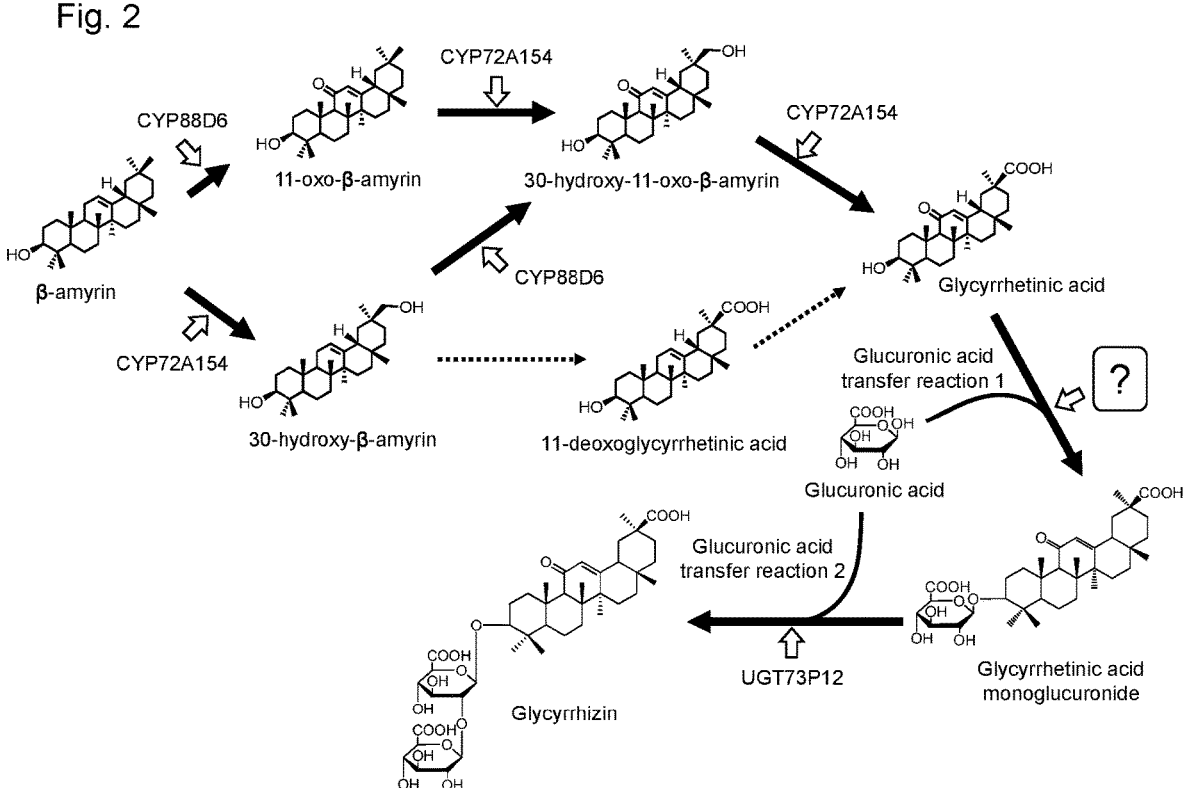
FIG. 2 shows oleanane-type triterpenoids generated as intermediate products in biosynthetic pathways from β-amyrin to glycyrrhizin, known enzymes (CYP88D6, CYP72A154, and UGT73P12) involved in conversion reactions, and the steps catalyzed by glucuronosyltransferase 1 CSyGT newly identified in the specification.

As a result, saponins (Bb, βg, etc.), normally accumulated in the homozygous mutant (mutant homo), is below a detectable level, and abnormalities were observed in the saponin composition, as shown in (b) and (c) in FIG. 12-1 and FIG. 12-2. The results show that Glyma.06G324300 homologous gene (Lj3g3v1981230) of *Lotus japonicus* actually functions in vivo in the saponin biosynthetic system.

Example 16: Construction of Expression Vector for *Lotus japonicus*

A cycle of PCR was repeated 30 times by use of Prime-STAR GXL DNA Polymerase (TAKARA BIO INC.) at an annealing temperature of 60° C. and a reaction temperature of 68° C., using a vector for cloning containing *Glycyrrhiza*-derived Glyma.06G324300 homologous gene produced in Example 4 as a template and a forward primer (SEQ ID NO: 31) and a reverse primer (SEQ ID NO: 32) that amplify from the initiation codon to the stop codon of SEQ ID NO: 4. The DNA fragment, which was amplified, was cloned to pDONR™221 by the nucleotide sequence specific recombination reaction (GATEWAY attB×attP reaction) using Gateway BP Clonase II Enzyme Mix (Thermo Fisher Technologies). The polynucleotide sequences of the resultant three independent clones were determined, and found to coincide with SEQ ID NO: 4. The plasmid pDONR-Glyur003152s00037491 having the polynucleotide was obtained as an entry clone.

Subsequently, using a vector for cloning containing *Lotus japonicus*-derived Glyma.06G324300 homologous gene produced in Example 5 as a template, and the forward primer (SEQ ID NO: 33) and the reverse primer (SEQ ID NO: 34) which amplify from the initiation codon to the stop codon of SEQ ID NO: 6, PCR was performed in the same manner as described above to clone into pDONR™221. The polynucleotide sequences of the resultant three independent clones were determined, and found to coincide with SEQ ID NO: 6. The plasmid pDONR-Lj3g3v 1981230 having the polynucleotide was obtained as an entry clone. Note that 12 nucleotides represented by SEQ ID NO: 35 (AAAAAGCAGGCT) are artificially added to the 5' terminal of the forward primer and 12 nucleotides represented by SEQ ID NO: 36 (AGAAAGCTGGGT) are artificially added to the 5' terminal of the reverse primer, for the reason that the nucleotides are required for nucleotide sequence specific recombination reaction (GATEWAY attB× attP reaction) in cloning into pDONR™221 (Thermo Fisher Technologies). A plasmid (entry clone) pDONR-Glyma.06g324300 having the polynucleotide represented by SEQ ID NO: 2 or a plasmid (entry clone) pDONR-Glyur003152s00037491 having the polynucleotide represented by SEQ ID NO: 4, a plasmid (entry clone) pDONR-Lj3g3v1981230 having the polynucleotide represented by SEQ ID NO: 6, produced in Example 1, and a destination vector pG35NGw were mixed with each other, and subjected to a nucleotide sequence specific recombination reaction (GATEWAY attL×attR reaction) using Gateway LR Clonase II Enzyme Mix (Thermo Fisher Technologies) to transfer the DNA fragment represented by SEQ ID NO: 6 to pCAMBIA-G35NGw. In this manner, a vector pG35N-LjCSL for *Lotus japonicus* transformation containing *Lotus japonicus*-derived Glyma.06G324300 homologous gene represented by SEQ ID NO: 6 was obtained. In the same manner as described above, soy bean-derived Glyma.06G324300 gene represented by SEQ ID NO: 2, and *Glycyrrhiza*-derived Glyma.06G324300 homologous gene represented by SEQ ID NO: 4 were transferred to obtain vectors for transformation of *Lotus japonicus* pG35N-GmCSL and pG35N-GuCSL, respectively.

Example 17: Rescue Experiment by Introduction of Soy Bean Glyma.06G324300, And *Glycyrrhiza* and *Lotus japonicus* Glyma.06G324300 Homologous Genes into *Lotus Japonicus*-Mutant Glyma.06G324300 homologous genes were introduced into *Lotus japonicus* Glyma.06G324300 homologous gene loss-of-function mutant according to the method described in Diaz et al., (2005) Induction of hairy roots for symbiotic gene expression studies. In *Lotus japonicus* Handbook, A. J. Marquez, ed (Dordrecht, The Netherlands: Springer), pp. 261-277. Seeds obtained from a mutant homozygous lineage of *Lotus japonicus* Glyma.06G324300 homologous gene loss-of-function mutant 30006020 obtained in Example 14 were sterilized with hypochlorous acid of effective chlorine concentration of 2% (containing 0.02% Tween20) for 20 minutes, then allowed to absorb water in sterile distilled water overnight. The water absorbed seeds were hulled, seeded on 0.8% water agar medium, shaded with aluminum foil, cultured at 25° C. for 4 days, and then illuminated for 1 day. The vector produced in Example 16 was introduced into *Agrobacterium* (LBA1334), plated on the front surface of L medium, and cultured at 28° C. for 1 day. After *Agrobacterium* cultured for 1 day was suspended in 10 mL of sterile water and placed in a round sterile petri dish, the seedlings of the mutant homozygous lineage of *Lotus japonicus* Glyma.06G324300 homologous gene loss-of-function mutant 30006020 were immersed therein and the hypocotyl was cut with a razor. The cut seedlings were placed on a cocultivation medium, shaded with aluminum foil, and co-cultured at 21° C. for 4 days. After co-cultivation, plants were placed on HRE medium and grown for 2 weeks with 16 hours of light period at 25° C./8 hours of dark period at 23° C. In the plants that developed hairy roots, GFP fluorescence was confirmed under a fluorescent stereomicroscope.

Figure 13:
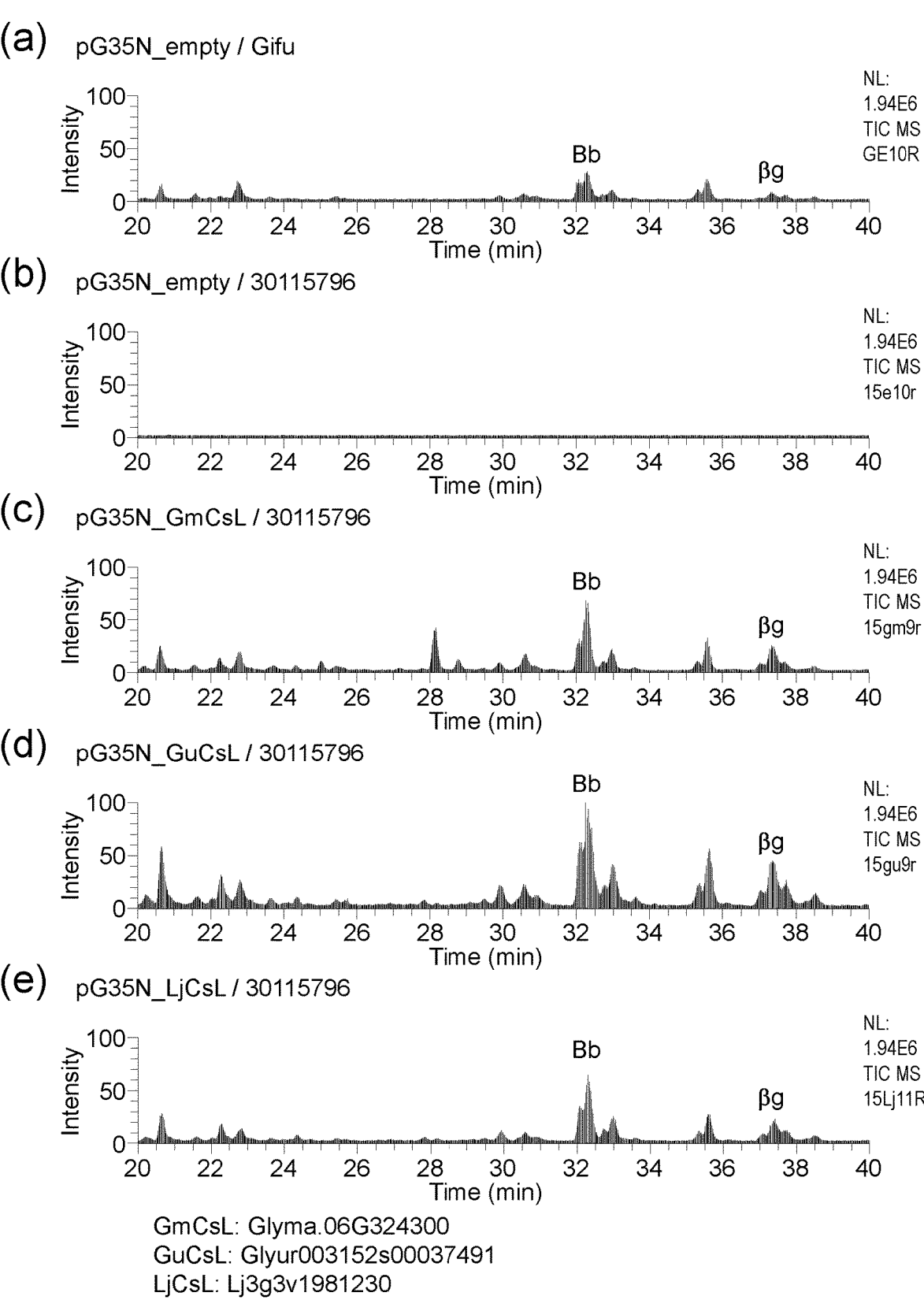
FIG. 13 shows LC-PDA/MS/MS analysis results of Glyma.06G324300 homologous gene-introduced loss-of-function mutant hairy root. This figure shows total ion chromatograms of hairy root extracts derived from: (a) a strain of wild-type (Gifu) into which an empty vector (pG35N_empty) was introduced, and (b) to (e) transformants of Glyma.06G324300 homologous gene loss-of-function homozygous mutant (30115796) strains into which pG35N_empty, expression vectors pG35N-GmCSL, pG35N-GuCSL, and pG35N-LjCSL were introduced, respectively.

Example 18: Triterpenoid Saponin Composition Analysis of *Lotus japonicus* Hairy Root The plants that developed hairy roots obtained in Example 17 were transplanted into pots filled with vermiculite, and B & D hydroponic solution (Diaz et al., 2005) was added and grown for one month. Sufficiently grown plants were freeze-dried and ground in Multi-beads shocker (Yasui Instrument Co., Ltd.) at 2500 rpm for 30 seconds. 80% Methanol, 100 times the weight of the freeze-dried material, was added, and shaken at room temperature for 1 hour, and then centrifuged at 15 krpm for 5 minutes to collect the supernatant. The supernatant was analyzed by LC-PDA/MS/MS using the method shown in Example 15. As a result, the saponins that had disappeared in the mutant were restored in the transformed hairy roots as shown in FIG. 13. Therefore, it was considered that Glyma.06G324300 homologous gene also catalyzes the saponin synthesis reaction in vivo.

Example 19: Search and Isolation of *Astragalus*-Derived Glyma.06G324300 Homologous Gene Glyma.06G324300 homologous gene was searched as a candidate for an orthologue gene of Glyma.06G324300 by gene homology search from *Astragalus* (*Astragalus sinicus*) which belongs to the same Fabaceae plant as soybean. A kind of nucleotide sequence, AsCSyGT, which encodes protein exhibiting high amino acid identity with Glyma.06G324300 was found from a sequence database integrating RNA sequence data obtained from roots, stems, and leaves of *Astragalus*. Using the total RNA (1 μg) obtained, a first-strand cDNA was synthesized by use of SMART RACE cDNA amplification kit (Clontech) in accordance with the attached protocol. A cycle of PCR was repeated 30 times by use of PrimeSTAR Max DNA Polymerase (TAKARA BIO INC.) at an annealing temperature of 55° C. and a reaction temperature of 72° C., using the first-strand cDNA (2 μL) as a template and oligo DNA molecules corresponding to the N terminal and C terminal of the polypeptide estimated from AsCSyGT, respectively, as a forward primer (SEQ ID NO: 39) and a reverse primer (SEQ ID NO: 40). Note that 4 nucleotides (cacc) are artificially added to the 5' terminal of the forward primer, for the reason that the nucleotides are required for cloning into pENTR™/D-TOPO (registered trademark) entry vector (Thermo Fisher Technologies). The DNA fragment, which was amplified, was cloned to pENTR™/D-TOPO entry vector. The polynucleotide sequences of the resultant two independent clones were determined. As a result, the nucleotide sequence of Glyma.06G324300 homologous gene of *Astragalus* thus obtained is represented by SEQ ID NO: 41. The polypeptide sequence estimated from the nucleotide sequence is represented by SEQ ID NO: 42. The amino acid sequence represented by SEQ ID NO: 42 had 77% identity with the amino acid sequence represented by SEQ ID NO: 1.

Example 20: Isolation of Soy Bean-Derived Glyma.06G324300 Homologous Gene

Glyma.06G324300 homologous gene was searched as a candidate for a paralogue gene of Glyma.06G324300 by gene homology search from soy bean. Using BLAST homology search function in genome information database of soy bean, i.e., Soy base (https-colon-slash-slash soy base.org), two types of nucleotide sequences, Glyma.04g255400 and Glyma.11g151800, which may encode proteins having high amino acid identity with Glyma.06G324300, were found. Two types of Glyma.06G324300 homologous gene, Glyma.04g255400 and Glyma.11g151800 were amplified by the method described in Example 1, and cloned into pDONR™221 (Thermo Fisher Technologies). Oligo DNA molecules corresponding to the N terminal and C terminal of the polypeptide estimated from Glyma.04g255400 were respectively used as a forward primer (SEQ ID NO: 43) and a reverse primer (SEQ ID NO: 44), and oligo DNA molecules corresponding to the N terminal and C terminal of the polypeptide estimated from Glyma.11g151800 were respectively used as a forward primer (SEQ ID NO: 45) and a reverse primer (SEQ ID NO: 46). Note that 12 nucleotides (AAAAAGCAGGCT) are artificially added to the 5' terminal of the forward primer and 12 nucleotides (AGAAAGCTGGGT) are artificially added to the 5' terminal of the reverse primer, for the reason that the nucleotides are required for nucleotide sequence specific recombination reaction (GATEWAY attB× attP reaction) in cloning into pDONR™221 (Thermo Fisher Technologies). The DNA fragment, which was amplified from seed-derived first-strand cDNA, was cloned to pDONR™221 by the nucleotide sequence specific recombination reaction (GATEWAY attB× attP reaction) using Gateway BP Clonase II Enzyme Mix (Thermo Fisher Technologies). The polynucleotide sequences of the resultant three independent clones were determined. As a result, the sequences thus obtained are represented by SEQ ID NO: 47 and SEQ ID NO: 49. The polypeptide sequences estimated from the sequences are represented by SEQ ID NO: 48 and SEQ ID NO: 50. The amino acid sequences represented by SEQ ID NO: 48 and SEQ ID NO: 50 had identities of 93.9% and 71.1%, respectively, with the amino acid sequence represented by SEQ ID NO: 1.

Example 21: Introduction of Glyma.06G324300
Homologous Gene of *Astragalus* And Soy Bean
into Glycyrrhetinic Acid and Soyasapogenol
B-Producing Yeast Strain According to the method described in Example 7, pESC-HIS-AsCSyGT, pESC-HIS-AtUGD2-Glyma04g255400, pESC-HIS-AtUGD2-Glyma.11g151800, which are yeast expression clones of Glyma.06G324300 homologous genes of *Astragalus* obtained in Example 19 and soy bean obtained in Example 20, were constructed, and introduced into glycyrrhetinic acid and soyasapogenol B-producing yeast strain, respectively, according to the method shown in Example 8.

Example 22: In Vivo Enzyme Assay Using
Recombinant Yeast into which Glyma.06G324300
Homologous Genes of *Astragalus* and Soybean
were Introduced According to the method described in Example 9, recombinant yeast was cultured, and metabolites were extracted. As a result, a metabolite extract (sample Q) derived from glycyrrhetinic acid-producing yeast strain expressing a polypeptide represented by SEQ ID NO: 42 (AsCSyGT), a metabolite extract (sample R) derived from glycyrrhetinic acid-producing yeast strain expressing a polypeptide represented by SEQ ID NO: 48 (Glyma04g255400), a metabolite extract (sample S) derived from glycyrrhetinic acid-producing yeast strain expressing a polypeptide represented by SEQ ID NO: 50 (Glyma.11g151800) were obtained. In the same manner, soyasapogenol B-producing yeast strains having pESC-HIS-AsCSyGT, pESC-HIS-AtUGD2-Glyma04g255400, pESC-HIS-AtUGD2-Glyma.11g151800 were also cultured, and the metabolites were extracted. As a result, a metabolite extract (sample T) derived from soyasapogenol B-producing yeast strain expressing a polypeptide represented by SEQ ID NO: 42 (AsCSyGT), a metabolite extract (sample U) derived from soyasapogenol B-producing yeast strain expressing a polypeptide represented by SEQ ID NO: 48 (Glyma04g255400), and a metabolite extract (sample V) derived from soyasapogenol B-producing yeast strain expressing a polypeptide represented by SEQ ID NO: 50 (Glyma.11g151800) were obtained.

Example 23: Analysis of Metabolite Extract of
Yeast into which Glyma.06G324300 Homologous
Genes of *Astragalus* and Soy Bean were Introduced According to the method described in Example 10, samples for LC-MS analysis were prepared, and analyzed. The results are shown in FIG. 14 and FIG. 15.

Figure 14:
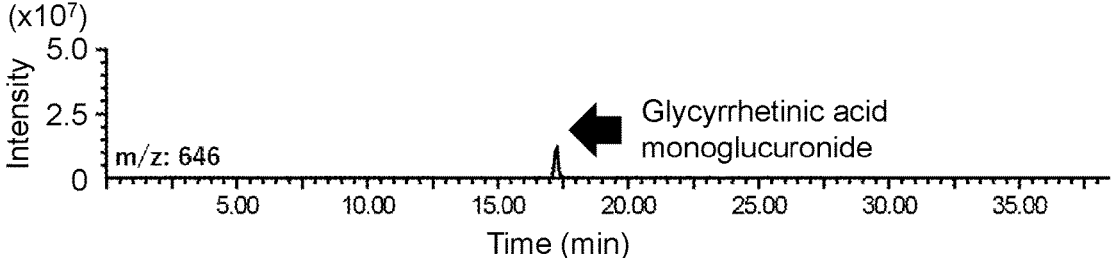
FIG. 14 shows metabolite analysis results in *Astragalus* Glyma.06G324300 orthologue gene- and soy bean Glyma.06G324300 paralogue gene-introduced glycyrrhetinic acid-producing yeast. Sample Q in (a) shows detection results of glycyrrhetinic acid monoglucuronide generated by expressing an AsCSyGT gene, which is an *Astragalus*-derived Glyma.06G324300 orthologue gene, in glycyrrhetinic acid-producing yeast: Sample R in (b) shows detection results of glycyrrhetinic acid monoglucuronide generated by expressing a Glyma04g255400 gene, which is a soy bean-derived Glyma.06G324300 paralogue gene, in glycyrrhetinic acid-producing yeast: Sample S in (c) shows detection results of glycyrrhetinic acid monoglucuronide generated by expressing a Glyma.11g151800 gene, which is a soy bean-derived Glyma.06G324300 paralogue gene, in glycyrrhetinic acid-producing yeast. The peak pointed by a solid arrow shows glycyrrhetinic acid monoglucuronide.
Figure 14:
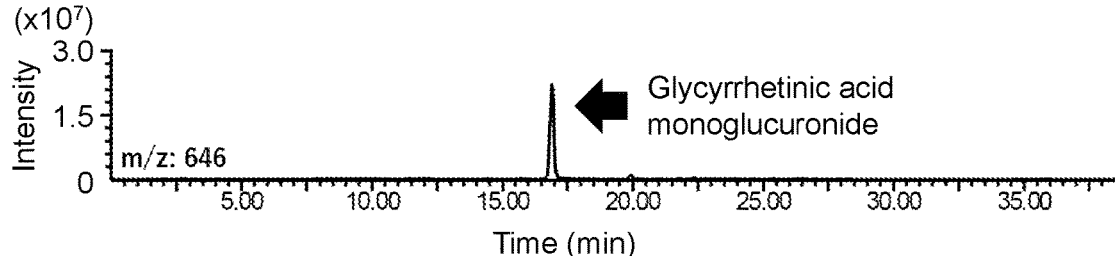
Figure 14:
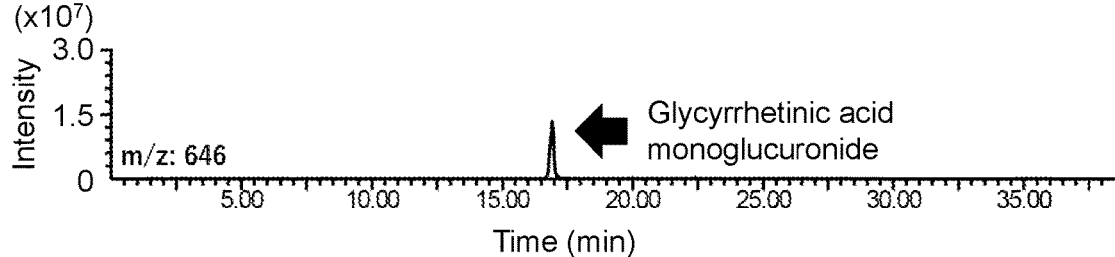

A peak (solid arrow) corresponding to glycyrrhetinic acid monoglucuronide was detected in sample Q in (a) shown in FIG. 14. The retention time and mass spectrum of this peak satisfactorily coincided with those of glycyrrhetinic acid monoglucuronide. Similarly, a peak (solid arrow) corresponding to glycyrrhetinic acid monoglucuronide was detected in sample R in (b) and sample S in (c). The retention time and mass spectrum of each peak satisfactorily coincided with those of glycyrrhetinic acid monoglucuronide.

Figure 15:
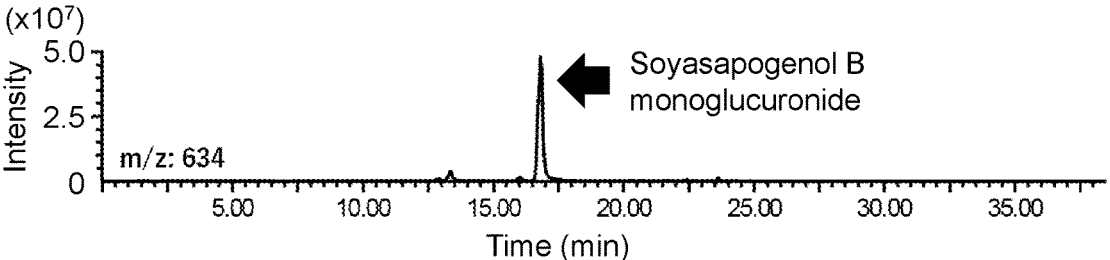
FIG. 15 shows metabolite analysis results in soyasapogenol B-producing yeast, into which *Astragalus* Glyma.06G324300 orthologue gene and soy bean Glyma.06G324300 paralogue gene were introduced. Sample T in (a) shows detection results of soyasapogenol B monoglucuronide generated by expressing an *Astragalus*-derived AsCSyGT gene in soyasapogenol B-producing yeast: Sample U in (b) shows detection results of soyasapogenol B monoglucuronide generated by expressing a soy bean-derived Glyma04g255400 gene in soyasapogenol B-producing yeast: Sample V in (c) shows detection results of soyasapogenol B monoglucuronide generated by expressing a soy bean-derived Glyma.11g151800 gene in soyasapogenol B-producing yeast. The peak pointed by a solid arrow shows soyasapogenol B monoglucuronide.
Figure 15:
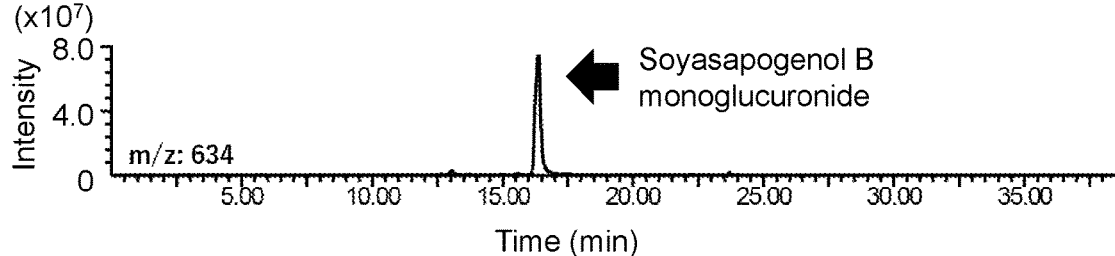
Figure 15:
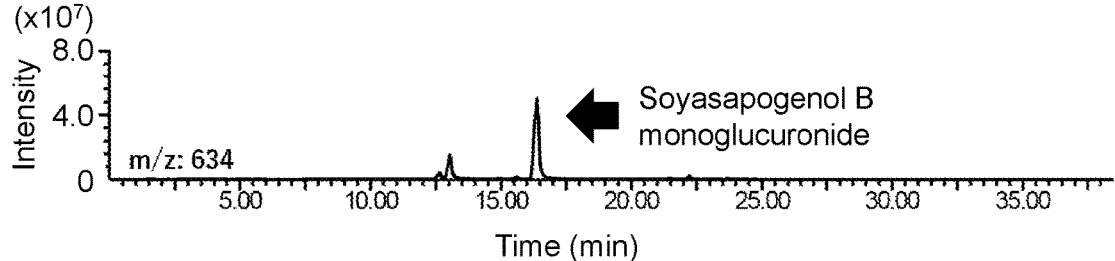

A peak (solid arrow) corresponding to soyasapogenol B monoglucuronide was detected in sample T in (a) shown in FIG. 15. A peak (solid arrow) corresponding to soyasapogenol B monoglucuronide was also detected in sample U in (b) and sample V in (c). The retention time and mass spectrum of each peak satisfactorily coincided with those of soyasapogenol B monoglucuronide.

The aforementioned results show that *Astragalus*-derived AsCSyGT obtained in Example 19, and soy bean-derived Glyma04g255400 and Glyma.11g151800 obtained in Example 20 have a glucuronic acid transfer activity 1 which converts glycyrrhetinic acid into glycyrrhetinic acid monoglucuronide by transferring glucuronic acid to the hydroxy group at the 3-position of the glycyrrhetinic acid. It is also demonstrated that they have glucuronic acid transfer activity 1 which converts soyasapogenol B into soyasapogenol B monoglucuronide by transferring glucuronic acid to the hydroxy group at the 3-position of the soyasapogenol B.

Example 24: Preparation of Transformed Yeast for
Substrate Feeding Assay of Glyma.06G324300
Homologous Gene of Soybean pESC-HIS-AtUGD2-Glyma04g255400 and pESC-HIS-AtUGD2-Glyma.11g151800 obtained in Example 21, were respectively introduced into the yeast INVSc1 strains. The yeast was transformed by use of Frozen-EZ Yeast Transformation II (Zymo Research) in accordance with the attached protocol.

Example 25: Substrate Feeding Assay Using
Transformed Yeast into which Glyma.06G324300
Homologous Gene of Soy Bean was Introduced The recombinant yeast obtained in Example 24 was cultured by the method shown in Example 12. The resulting suspension of each yeast cell was aliquoted and ursolic acid of ursane-type triterpenoid or betulinic acid of lupin-type triterpenoid at a final concentration of 5 M was added, respectively. Thereafter, culture and extraction of metabolite were performed again using the method shown in Example 12. As a result, feeding assay extracts including a transformed yeast expressing polypeptide represented by SEQ ID NO: 48 (Glyma04g255400) or polypeptide represented by SEQ ID NO: 50 (Glyma.11g151800), with an ursane-type triterpenoid, i.e., ursolic acid, added thereto, and those with lupane-type triterpenoid, i.e., betulinic acid, added thereto, were obtained.

Figure 16:
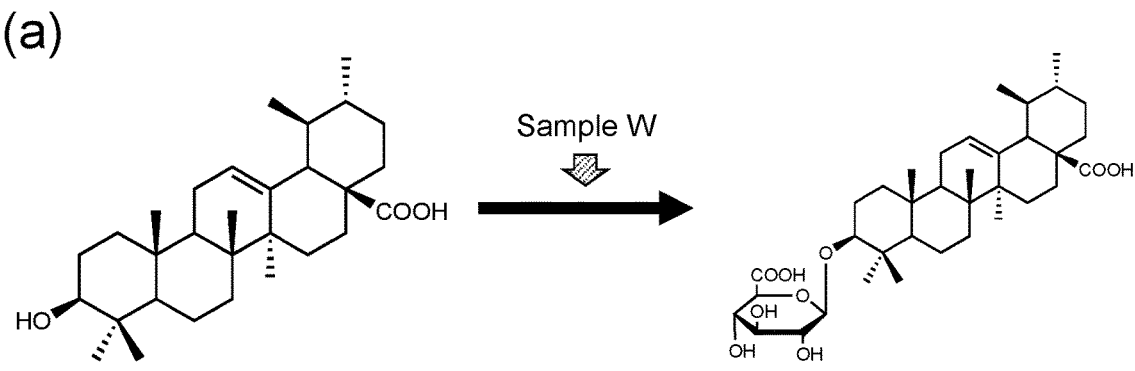
FIG. 16 shows metabolite analysis results in soy bean-derived Glyma.11g151800 gene-introduced yeast, to which ursolic acid was fed. (a) is a conceptual diagram showing envisaged conversion reactions to ursolic acid monoglucuronide when Glyma.11g151800 feeding assay extract (sample W) was used. (b) shows detection results of ursolic acid monoglucuronide generated by Glyma.11g151800 when sample W was added. The peak pointed by a solid arrow shows ursolic acid monoglucuronide. (c) shows detection results of ursolic acid monoglucuronide when sample X as a negative control was added.
Figure 16:
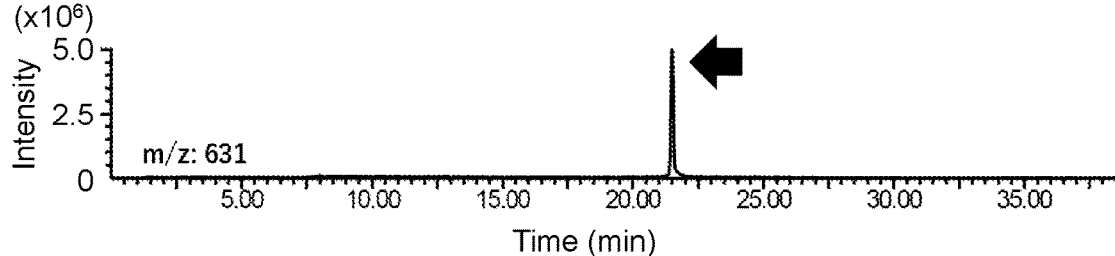
Figure 16:
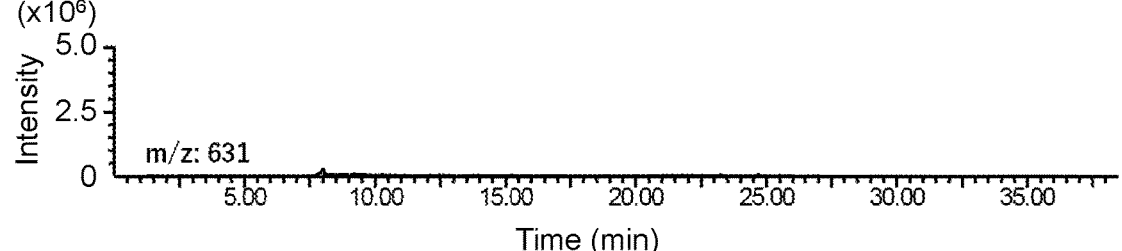

Example 26: Analysis of Substrate Feeding Assay
Extract Using Transformed Yeast Into which
Glyma.06G324300 Homologous Gene of Soybean
was Introduced Samples obtained in Example 25 were analyzed in the same manner as in Example 10, using SIM mode with the following parameters in MS: m/z of each expected reaction product, ursolic acid monoglucuronide=631 (FIG. 16, a), betulinic acid monoglucuronide=631 (FIG. 17, a). FIG. 16 shows analysis results of a feeding assay extract (sample W) including a transformed yeast expressing a polypeptide represented by SEQ ID NO: 50 (Glyma.11g151800) to which ursolic acid was added. A peak estimated as ursolic acid monoglucuronide was detected in sample W shown in (b). In contrast, in sample X which is a negative control shown in (c), a peak estimated as ursolic acid monoglucuronide was not detected.

FIG. 17 shows analysis results of a feeding assay extract (sample Y) including a transformed yeast expressing a polypeptide represented by SEQ ID NO: 50 (Glyma.11g151800) to which betulinic acid was added. A peak estimated as betulinic acid monoglucuronide was detected in sample Y shown in (b). In contrast, from sample Z which is a negative control shown in (c), a peak estimated as betulinic acid monoglucuronide was not detected.

Based on the above, it is considered that the polypeptide (Glyma.11g151800) represented by SEQ ID NO: 50 is glucuronosyltransferase 1 capable of transferring glucuronic acid to the hydroxy group at the 3-position not only of oleanane-type triterpenoid, but also of ursane-type triterpenoid such as ursolic acid and β-boswellic acid, and of lupane-type triterpenoid such as betulinic acid.

All publications, patents and patent applications cited in the specification as references are incorporated in their entirety herein.

The invention claimed is:

1. A recombinant cell for producing glycyrrhizin, wherein the recombinant cell is obtained from a non-animal, capable of biologically synthesizing β-amyrin, and comprises all of the following polynucleotides (1) to (4):

(1) a polynucleotide encoding a polypeptide having an activity of oxidizing the 11-position in an oleanane-type triterpenoid and consisting of an amino acid sequence of the following (a) or (b):
        (a) the amino acid sequence of SEQ ID NO:7, or
        (b) an amino acid sequence having at least 90% sequence identity with the amino acid sequence of SEQ ID NO:7;

(2) a polynucleotide encoding a polypeptide having an activity of oxidizing the 30-position in an oleanane-type triterpenoid and consisting of an amino acid sequence of the following (c) or (d):
        (c) the amino acid sequence of SEQ ID NOs: 9, 11, or 13, or
        (d) an amino acid sequence having at least 90% sequence identity with the amino acid sequence of SEQ ID NOs: 9, 11, or 13;

(3) a polynucleotide encoding a polypeptide having an activity to transfer glucuronic acid to the hydroxy group at the 2-position of glucuronic acid in an oleanane-type triterpenoid monoglucuronide and consisting of an amino acid sequence of the following (e) or (f):
        (e) the amino acid sequence of SEQ ID NO:15, or
        (f) an amino sequence having at least 90% sequence identity with the amino acid sequence of SEQ ID NO: 15; and (4) a polynucleotide encoding a polypeptide having an activity to transfer glucuronic acid to the hydroxy group at the 3-position in an oleanane-type triterpenoid, and consisting of an amino acid sequence of the following (g) or (h):
        (g) the amino acid sequence of SEQ ID NOs: 3 or 5, or
        (h) an amino acid sequence polypeptide having at least 95% sequence identity with the amino acid sequence of SEQ ID NOs: 3 or 5.

2. The recombinant cell according to claim 1, wherein the cell is from a Fabaceae plant.

3. A method for producing glycyrrhizin from β-amyrin, comprising culturing the recombinant cell according to claim 1.

\* \* \* \* \*

SEQUENCE LISTING

```
<160> NUMBER OF SEQ ID NOS: 52

<210> SEQ ID NO 1
<211> LENGTH: 699
<212> TYPE: PRT
<213> ORGANISM: Glycine max

<400> SEQUENCE: 1

Met Ala Met Phe Thr Tyr His Val Glu Thr Val Gln Ser Trp Leu Ala
1               5                   10                  15

Leu Ser Arg Leu His Ile Leu Ile His Leu Val Ala Val Leu Ser Leu
                20                  25                  30

Cys Tyr Tyr Arg Ile Thr His Leu Leu Leu Glu Pro Pro Thr Ala Pro
            35                  40                  45

Trp Leu Leu Met Thr Val Ala Glu Leu Leu Leu Ser Val Leu Trp Phe
        50                  55                  60

Phe Asn Gln Ala Phe Arg Trp Arg Pro Val Ser Arg Ser Val Met Thr
65                  70                  75                  80

Glu Lys Leu Pro Arg Asp Glu Lys Leu Pro Gly Leu Asp Ile Phe Val
                85                  90                  95

Cys Thr Leu Asp Pro Glu Lys Glu Pro Thr Val Glu Val Met Asp Thr
            100                 105                 110

Ile Ile Ser Ala Val Ala Met Asp Tyr Pro Ser Asp Lys Leu Ala Val
            115                 120                 125

Tyr Leu Ser Asp Asp Gly Gly Cys Asp Val Thr Leu Tyr Gly Ile Arg
        130                 135                 140

Glu Ala Ala Glu Phe Ala Lys Glu Trp Val Pro Phe Cys Asn Ile Tyr
145                 150                 155                 160

Gly Val Lys Ser Arg Cys Pro Lys Val Phe Phe Ser Pro Phe Gly Glu
                165                 170                 175

Glu Asp Gln His Thr Leu Arg His Asp Gly Phe Ser Thr Gln Arg Asp
                180                 185                 190

Leu Ile Lys Ala Lys Tyr Glu Lys Met Gln Lys Asn Ile Glu Lys Phe
            195                 200                 205

Gly Ser Asp Pro Lys Asn Arg Arg Ile Val Ser Asp Arg Pro Pro Arg
        210                 215                 220

Ile Glu Ile Ile Asn Asp Gln Pro Gly Met Pro Leu Val Val Tyr Val
225                 230                 235                 240

Ser Arg Glu Arg Arg Pro Ser Leu Pro His Lys Phe Lys Gly Gly Ala
                245                 250                 255

Leu Asn Ala Leu Leu Arg Val Ser Gly Leu Ile Ser Asn Gly Pro Tyr
            260                 265                 270

Val Leu Ala Val Asp Cys Asp Met Tyr Ser Asn Asp Pro Thr Ser Ala
            275                 280                 285

Lys Gln Ala Met Cys Phe Phe Leu Asp Pro Glu Thr Ser Lys Tyr Ile
        290                 295                 300

Ala Phe Val Gln Phe Pro Gln Met Phe His Asn Leu Ser Lys Lys Asp
305                 310                 315                 320
```

-continued

```
Ile Tyr Asp Asn Gln Ser Arg Thr Ala Phe Lys Thr Met Trp Gln Gly
            325                 330                 335

Met Asp Gly Leu Arg Gly Pro Gly Leu Ser Gly Ser Gly Asn Tyr Leu
        340                 345                 350

Ser Arg Ser Ala Leu Leu Phe Gly Ser Pro Asn Gln Lys Asp Asp Tyr
        355                 360                 365

Leu Lys Asp Ala Gln Lys Tyr Phe Gly Lys Ser Thr Ala Tyr Ile Glu
    370                 375                 380

Ser Leu Lys Ala Ile Arg Gly Gln Lys Ser Ser Lys Lys Asn Ile Ser
385                 390                 395                 400

Arg Asp Glu Met Leu Arg Glu Ala Gln Val Val Ala Ser Cys Ser Tyr
                405                 410                 415

Glu Asn Asn Thr Asn Trp Gly Thr Glu Val Gly Phe Ser Tyr Gly Ile
            420                 425                 430

Leu Leu Glu Ser Thr Ile Thr Gly Tyr Leu Leu His Ser Arg Gly Trp
        435                 440                 445

Lys Ser Ala Tyr Leu Tyr Pro Lys Thr Pro Cys Phe Leu Gly Cys Ala
    450                 455                 460

Pro Thr Asp Ile Lys Glu Gly Met Leu Gln Leu Val Lys Trp Leu Ser
465                 470                 475                 480

Glu Leu Leu Leu Leu Gly Val Ser Ser Lys Tyr Ser Pro Phe Thr Tyr
                485                 490                 495

Gly Phe Ser Arg Met Ser Ile Ile His Thr Phe Thr Tyr Cys Phe Met
            500                 505                 510

Thr Met Ser Ser Leu Tyr Ala Val Val Phe Ile Leu Tyr Gly Ile Val
        515                 520                 525

Pro Gln Val Cys Leu Leu Lys Gly Ile Thr Val Phe Pro Lys Ala Thr
    530                 535                 540

Asp Pro Trp Phe Ala Val Phe Ala Phe Val Tyr Val Ser Thr Gln Ile
545                 550                 555                 560

Gln His Leu Ile Glu Val Leu Ser Gly Asp Gly Ser Val Ala Met Trp
                565                 570                 575

Trp Asp Glu Gln Arg Ile Trp Ile Leu Lys Ser Val Thr Ser Ile Phe
            580                 585                 590

Ala Ile Ile Asp Gly Ile Lys Lys Trp Leu Gly Leu Asn Lys Val Lys
        595                 600                 605

Phe Asn Leu Ser Asn Lys Ala Ile Asp Lys Glu Lys Leu Lys Lys Tyr
    610                 615                 620

Glu Gln Gly Arg Phe Asp Phe Gln Gly Ala Ala Val Phe Met Ala Pro
625                 630                 635                 640

Leu Val Leu Leu Leu Ile Ala Asn Ile Val Ser Phe Phe Val Gly Ile
                645                 650                 655

Trp Arg Leu Phe Asn Phe Asn Val Lys Asp Phe Glu Glu Met Phe Gly
            660                 665                 670

Gln Leu Phe Leu Val Thr Tyr Val Met Leu Leu Ser Tyr Pro Ile Leu
        675                 680                 685

Glu Ala Ile Val Thr Met Lys Ser Lys Ser Gly
    690                 695
```

<210> SEQ ID NO 2
<211> LENGTH: 2100
<212> TYPE: DNA
<213> ORGANISM: Glycine max

<400> SEQUENCE: 2

```
atggcaatgt tcacgtacca cgttgaaacg gttcaatcat ggttggcact gagcagactt      60
cacatactga tccacttagt ggcagtgttg tcgctgtgtt actaccgcat aactcacttg     120
ttactggaac ctccaacagc gccatggctt ctgatgaccg tagcggagct tcttctctcg     180
gtgctctggt tcttcaacca agccttccgg tggcggccgg tgtcgcgag cgtcatgacg     240 gagaagctgc cgagggatga gaagctgccg gggcttgaca tcttcgtgtg cacgctggat     300
cccgagaagg agcccaccgt ggaggtcatg gacaccatca tctccgcggt ggccatggat     360
tacccctccg acaagcttgc cgtgtatctc tccgacgacg cggctgtga cgttactctc     420 tatgggatca gagaggctgc tgagttcgcc aaggagtggg ttccgttctg taacatttat     480
ggggtcaagt caaggtgtcc caaggtcttc ttctctccct ttggggagga ggatcaacac     540
actcttcgcc acgatggatt cagtacacaa cgagacctca tcaaggctaa atacgagaag     600
atgcagaaaa atatcgagaa atttggctca gaccctaaaa atcgtcgtat tgtgagtgac     660
agacctcctc gtattgagat tataaatgac caaccgggaa tgccacttgt tgtttatgtg     720
tctcgcgaaa gaaggccatc ccttcctcac aaattcaaag gaggagccct caacgcattg     780
ctcagagtct caggtttaat cagtaatgga cctttatgttc tagcagtgga ttgtgatatg     840
tatagcaatg atccaacctc tgccaaacaa gccatgtgct tctttcttga tcctgaaacg     900
tccaaatata ttgcatttgt tcaattccct caaatgtttc acaaccttag caaaaaagac     960
atctatgata atcaatctag aactgctttt aagactatgt ggcaaggcat ggatggacta    1020
agaggtccag gtctttcagg cagcggcaat tacttaagta gaagtgcttt actatttgga    1080
agtccaaacc aaaaagacga ctatctgaag gatgcacaaa agtactttgg caagtctacc    1140
gcatacattg aatcactgaa ggccatccgt ggacagaaaa gtagcaaaaa gaatatttca    1200
agagatgaaa tgttaagaga agctcaagta gtggcctctt gttcctacga aaataacaca    1260
aattggggca cagaggtggg attctcatat ggcatattac tagagagtac tattactggc    1320
tatcttcttc acagcagagg atggaaatca gcatatcttt accccaaaac accatgtttc    1380
ttaggttgtg ctcccactga catcaaggaa ggcatgcttc agttggttaa gtggttgtct    1440
gaacttttgt tgcttggtgt ctcctccaaa tacagcccat tcacttatgg attttcaaga    1500
atgtccataa ttcacacctt cacttattgc ttcatgacaa tgtcatccct ttatgctgtt    1560
gtcttcatcc tctatggcat tgtacctcaa gtgtgcctcc tcaaaggaat cactgtgttt    1620
ccaaaggcca cggacccttg gtttgcagtg tttgcatttg tgtatgtatc tactcaaatt    1680
caacatttga ttgaggttct atctggggat ggctctgtgg ctatgtggtg ggatgaacaa    1740
agaatttgga ttctgaagtc agttaccagc atatttgcaa ttatagatgg aatcaagaag    1800
tggctggggt tgaacaaggt gaaattcaac ttgtcaaaca aagccattga caaggagaag    1860
ctcaagaaat atgagcaagg taggttcgat ttccaaggtg cagctgtgtt catggctcca    1920
ttggtcctat tactcatagc caacattgtt agcttctttg ttggtatatg gagactattc    1980
aatttcaatg tgaaggattt tgaagaaatg tttggtcaac ttttcctagt cacctatgta    2040
atgcttctta gttatcccat tcttgaggcc atagtaacaa tgaaaagcaa aagtggatag    2100
```

<210> SEQ ID NO 3
<211> LENGTH: 695
<212> TYPE: PRT
<213> ORGANISM: Glycyrrhiza uralensis

<400> SEQUENCE: 3

-continued

```
Met Ala Ser Phe Thr Leu His Thr Glu Thr Val Gln Ser Trp Leu Leu
1               5                  10                 15

Leu Ser Arg Leu His Ile Leu Leu His Leu Ala Val Val Leu Leu Leu
            20                 25                 30

Leu Tyr Tyr Arg Ile Thr Arg Phe Pro Phe His Ala Pro Thr Leu Pro
        35                 40                 45

Trp Thr Leu Met Thr Val Gly Glu Ala Ile Met Ala Val Leu Trp Phe
    50                 55                 60

Phe Asn Gln Ala Phe Arg Trp Arg Pro Val Ser Arg Ser Val Met Thr
65                 70                 75                 80

Glu Lys Leu Pro Ser Asp Ala Lys Leu Pro Gly Leu Asp Ile Phe Val
                85                 90                 95

Cys Thr Leu Asp Pro Glu Lys Glu Pro Thr Val Glu Val Met Asn Thr
            100                105                110

Leu Val Ser Ala Leu Ala Met Asp Tyr Pro Pro Asp Lys Leu Ser Val
            115                120                125

Tyr Leu Ser Asp Asp Gly Ala Ala Pro Val Thr Leu Tyr Gly Val Arg
    130                135                140

Glu Ala Ser Glu Phe Ala Arg Val Trp Val Pro Phe Cys Lys Lys Tyr
145                150                155                160

Gly Ile Lys Ser Arg Cys Pro Lys Val Phe Phe Ser Pro Ser Ala Glu
            165                170                175

Asp Glu His Leu Leu Arg Thr Asp Glu Phe Arg Ser Glu Arg Asp Leu
            180                185                190

Ile Lys Ala Lys Tyr Glu Lys Met Gln Lys Asn Ile Glu Lys Phe Gly
            195                200                205

Ser Asp Ala Lys Asn Cys Arg Met Val Thr Asp Arg Pro Pro Arg Ile
    210                215                220

Glu Ile Leu Ile Asp Gln Pro Asp Met Pro Arg Val Val Tyr Val Ser
225                230                235                240

Arg Glu Arg Arg Pro Ser Leu Pro His Lys Phe Lys Gly Gly Ala Leu
            245                250                255

Asn Thr Leu Leu Arg Val Ser Gly Leu Ile Ser Asn Gly Pro Tyr Val
            260                265                270

Leu Val Val Asp Cys Asp Met Tyr Cys Asn Asp Pro Ser Ser Ala Lys
            275                280                285

Gln Ala Met Cys Phe Phe Leu Asp Pro Glu Thr Ser Lys Tyr Ile Ala
    290                295                300

Phe Val Gln Phe Pro Gln Met Phe His Asn Leu Gly Lys Lys Asp Ile
305                310                315                320

Tyr Asp Asn Gln Ser Arg Thr Ala Phe Lys Thr Met Trp Gln Gly Met
            325                330                335

Asp Gly Leu Arg Gly Pro Gly Leu Ser Gly Ser Gly Asn Tyr Leu Asn
            340                345                350

Arg Ser Ala Leu Leu Phe Gly Ser Pro Asn Gln Lys Asp Asp Tyr Leu
            355                360                365

Asp Asp Ala Gln Asn Tyr Phe Gly Lys Ser Thr Met Tyr Ile Glu Ser
    370                375                380

Leu Glu Ala Ile Arg Gly Gln Lys Thr Met Lys Lys Asn Ile Ser Arg
385                390                395                400

Asp Glu Ile Leu Arg Glu Ala Gln Val Leu Ala Ser Cys Ser Tyr Glu
            405                410                415

Thr Asn Thr Glu Trp Gly Ala Glu Val Gly Phe Ser Tyr Gly Ile Leu
```

-continued

```
                     420              425              430
Leu Glu Ser Ser Ile Thr Gly Tyr Leu Leu His Cys Arg Gly Trp Lys
         435              440              445
Ser Ala Tyr Leu Tyr Pro Lys Thr Pro Cys Phe Leu Gly Cys Ala Pro
         450              455              460
Thr Asp Ile Lys Glu Gly Met Leu Gln Leu Val Lys Trp Leu Ser Glu
465              470              475              480
Tyr Cys Leu Leu Gly Phe Ser Lys Tyr Ser Pro Phe Thr Tyr Gly Phe
             485              490              495
Ser Arg Met Pro Ile Met Pro Thr Leu Val Tyr Cys Phe Leu Thr Thr
             500              505              510
Thr Thr Leu Tyr Ser Ile Val Phe Ile Leu Tyr Gly Ile Val Pro Gln
         515              520              525
Val Cys Phe Leu Lys Gly Ile Pro Val Phe Pro Lys Val Thr Asp Pro
         530              535              540
Trp Phe Ala Val Phe Ala Thr Leu Tyr Ile Ser Thr Gln Ile Gln His
545              550              555              560
Leu Ile Glu Val Leu Ser Gly Asp Gly Ser Val Ala Met Trp Trp Asp
             565              570              575
Glu Gln Arg Ile Trp Ile Leu Lys Ser Val Thr Ser Val Phe Ala Ile
             580              585              590
Ile Glu Ala Ala Lys Lys Gly Leu Gly Leu Asn Lys Lys Lys Phe Met
         595              600              605
Leu Ser Asn Lys Ala Ile Asp Lys Glu Lys Leu Lys Lys Tyr Glu Gln
         610              615              620
Gly Arg Phe Asp Phe Gln Gly Ala Ala Leu Phe Met Ser Pro Met Val
625              630              635              640
Val Leu Leu Ile Val Asn Val Val Ser Phe Ile Gly Gly Ile Trp Arg
             645              650              655
Leu Phe Asn Ala Lys Asp Ile Glu Asp Met Phe Gly Gln Leu Phe Leu
         660              665              670
Val Ser Tyr Val Met Ala Leu Ser Tyr Pro Ile Phe Glu Gly Ile Ile
         675              680              685
Thr Met Lys Ser Lys Ser Gly
690              695
```

```
<210> SEQ ID NO 4
<211> LENGTH: 2088
<212> TYPE: DNA
<213> ORGANISM: Glycyrrhiza uralensis

<400> SEQUENCE: 4
atggcaagct tcacccttca cacagaaacc gttcagtcat ggctactcct cagcagactt        60
cacatactgc tgcacctcgc agttgtactg ctcctcttat actaccgcat cacacgtttc       120
cccttccatg ctccgactct accgtggact ctgatgaccg taggtgaggc tattatggca       180
gtgctgtggt tcttcaacca ggccttccgg tggcggccgg tgagccgctc ggtgatgacg       240
gagaagctgc ccagcgacgc gaagctgccg gggcttgaca tattcgtgtg cacgcttgac       300
cccgagaagg agcccaccgt ggaggtgatg aacactctgg tctctgccct tgccatggac       360
tacccccctg acaagctctc cgtttacctc tccgacgatg gcgccgcccc ggtcactctt       420
tacggcgtga gagaggcttc tgagttcgcg agggtgtggg tccctttctg caaaaagtat       480
gggatcaagt caaggtgtcc caaggttttc ttctctccca gtgctgagga tgaacacctt       540
```

-continued

```
cttcgcaccg acgagttcag gtcagagcga gacctcatca aggctaaata cgagaaaatg      600
cagaaaaata tcgagaaatt tggttcggat gccaaaaatt gtcgtatggt gaccgacaga      660
cctcctcgga tcgagatatt gattgaccaa ccagacatgc cacgtgttgt ttacgtgtct      720
cgggaaagaa ggccatcact ccctcacaag ttcaaaggag gagccctcaa tacattgctc      780
agagtctcag gtctaatcag caatgggcct tatgtacttg tagtggactg tgatatgtat      840
tgcaatgacc catcctcagc caaacaagcc atgtgtttct ttcttgatcc tgaaacctct      900
aaatatattg catttgtcca attccctcaa atgtttcaca accttggcaa aaaagacatc      960
tatgacaatc aatctaggac tgcttttaag acaatgtggc aagggatgga tggactaaga     1020
ggtcctggtc tttctggcag cggtaattac ttgaatagaa gtgcattact atttggaagt     1080
ccaaatcaaa aagatgacta tctggatgat gcccaaaact acttcggcaa gtctaccatg     1140
tacatagaat cactagaggc cattcgtgga caaaaaacta tgaaaaagaa tatttcaaga     1200
gatgaaattt tacgagaagc tcaagtatta gcctcttgtt cctatgagac aaacacagaa     1260
tggggcgcag aggtaggatt ctcatatggc atcttactgg agagttcaat cactggctat     1320
cttttgcact gcagaggatg gaaatcagca tatctttacc caaagacacc atgtttctta     1380
gggtgtgccc caactgacat caaggaagga atgctccaat ggtgaagtg  gttgtctgaa     1440 tactgcttgc ttggattctc taaatacagc cctttcactt atggctttttc aagaatgccc     1500 attatgccta cctagtctaa ttgcttcttg acaactacaa cccttattc cattgtcttc      1560 atcctttatg gcattgtccc ccaagtttgc ttcttaaaag gaatacccgt gtttccaaag     1620
gtcacagacc cttggtttgc agtgtttgca acactgtata tatccaccca gattcaacat     1680
ttgatagagg tcctttctgg tgatggctct gtggcaatgt ggtgggatga acagcgaatc     1740
tggattctga agtcagtcac tagcgtgttc gcaatcatag aggcagctaa gaaagggtta     1800
ggattgaaca agaagaaatt catgttgtca aacaaagcaa ttgacaagga gaagctcaag     1860
aagtatgagc aaggtaggtt tgatttccaa ggtgcagctc tgttcatgtc cccaatggtt     1920
gtgttgctca tagtgaacgt tgtttccttc attggtggca tatggagact attcaatgca     1980
aaggatattg aagatatgtt tggtcagctt ttcctagtta gttatgtaat ggcccttagt     2040
tatcccattt ttgaagggat aataaccatg aaaagcaaga gtggataa                 2088
```

<210> SEQ ID NO 5
<211> LENGTH: 694
<212> TYPE: PRT
<213> ORGANISM: Lotus japonicus

<400> SEQUENCE: 5

```
Met Ala Asn Phe Thr Leu His Thr Glu Thr Val Gln Ala Trp Leu Pro
1               5                   10                  15

Leu Ser Arg Leu His Ile Leu Ile His Ser Val Phe Val Ile Leu Leu
            20                  25                  30

Leu Tyr Tyr Arg Thr Thr Arg Leu Ile His Ala Pro Thr Ala Pro Trp
        35                  40                  45

Ile Leu Met Thr Val Ala Glu Ala Leu Leu Ala Val Leu Trp Leu Phe
    50                  55                  60

Asn Gln Ala Phe Arg Trp Arg Pro Val Ser Arg Ser Val Lys Thr Glu
65                  70                  75                  80

Lys Leu Pro Arg Asp Glu Asn Leu Pro Gly Leu Asp Ile Phe Val Cys
                85                  90                  95

Thr Ile Asp Pro Glu Lys Glu Pro Thr Ala Gly Val Met Asp Thr Val
```

-continued

```
                100                 105                 110

Val Ser Ala Val Ala Met Asp Tyr Pro Pro Asp Lys Leu Ser Val Tyr
            115                 120                 125

Leu Ser Asp Asp Gly Gly Cys Ala Val Thr Glu Tyr Gly Ile Arg Glu
        130                 135                 140

Ala Cys Glu Phe Ala Lys Val Trp Val Pro Phe Cys Arg Lys Tyr Gly
145                 150                 155                 160

Ile Lys Ser Arg Cys Pro Lys Val Phe Phe Ser Pro Met Gly Glu Asp
                165                 170                 175

Glu Glu Ile Leu Arg Thr Asp Glu Phe Arg Ala Glu Gln Glu Lys Ile
            180                 185                 190

Lys Ala Gln Tyr Glu Thr Met Gln Lys Asn Ile Glu Lys Phe Gly Ser
        195                 200                 205

Asp Pro Lys Asn Cys Arg Ile Val Thr Asp Arg Pro Ser Lys Ile Glu
    210                 215                 220

Ile Ile Asn Glu Gln Ser Glu Ile Pro Arg Val Val Tyr Val Ser Arg
225                 230                 235                 240

Glu Arg Arg Pro Ser Leu Pro His Lys Phe Lys Gly Gly Ala Leu Asn
                245                 250                 255

Thr Leu Leu Arg Val Ser Gly Leu Ile Ser Asn Gly Pro Tyr Val Leu
            260                 265                 270

Ala Val Asp Cys Asp Met Tyr Cys Asn Asp Pro Ser Ser Ala Lys Gln
        275                 280                 285

Ala Met Cys Phe Phe Leu Asp Pro Glu Thr Ser Lys Tyr Ile Ala Phe
    290                 295                 300

Val Gln Phe Pro Gln Met Phe His Asn Leu Ser Lys Lys Asp Ile Tyr
305                 310                 315                 320

Asp Asn Gln Ser Arg Thr Ala Phe Lys Thr Met Trp Gln Gly Met Asp
                325                 330                 335

Gly Leu Ser Gly Pro Gly Leu Ser Gly Ser Gly Asn Tyr Leu Ser Arg
            340                 345                 350

Ser Ala Leu Leu Phe Gly Ser Pro Asn Gln Lys Asp Asp Tyr Leu Leu
        355                 360                 365

Asp Ala Gln Asn Tyr Phe Gly Glu Ser Pro Leu Tyr Ile Glu Ser Leu
    370                 375                 380

Lys Ala Ile Arg Gly Gln Gln Thr Thr Lys Lys Asn Ile Ser Arg Asp
385                 390                 395                 400

Glu Ser Leu Leu Glu Ala Lys Val Val Ala Ser Ala Ser Tyr Glu Thr
                405                 410                 415

Asn Thr Glu Trp Gly Ser Glu Val Gly Phe Ser Tyr Gly Ile Leu Leu
            420                 425                 430

Glu Ser Thr Ile Thr Gly Tyr Leu Leu His Cys Arg Gly Trp Lys Ser
        435                 440                 445

Ala Tyr Leu Tyr Pro Lys Thr Pro Cys Phe Leu Gly Cys Ala Pro Thr
    450                 455                 460

Asp Ile Lys Glu Gly Met Leu Gln Leu Val Lys Trp Leu Ser Glu Leu
465                 470                 475                 480

Cys Leu Phe Ala Val Ser Lys Tyr Ser Pro Phe Thr Tyr Gly Phe Ser
                485                 490                 495

Arg Leu Pro Ile Met Pro Thr Phe Thr Tyr Cys Phe Leu Ala Ala Ser
            500                 505                 510

Ser Leu Tyr Ala Ile Val Phe Ile Leu Tyr Gly Ile Val Pro Gln Val
        515                 520                 525
```

```
Cys Phe Leu Lys Gly Ile Pro Val Phe Pro Lys Ala Thr Asp Pro Trp
    530             535             540

Phe Ala Val Phe Ala Val Leu Tyr Val Ala Thr Gln Ile Gln His Leu
545             550             555             560

Ile Glu Val Leu Ser Gly Asn Gly Ser Val Ser Met Trp Trp Asp Glu
                565             570             575

Gln Arg Ile Trp Ile Leu Lys Ser Val Thr Ser Val Phe Ala Met Ile
            580             585             590

Glu Gly Ile Lys Lys Trp Leu Gly Leu Asn Lys Lys Lys Phe Asn Leu
            595             600             605

Ser Asn Lys Ala Val Asp Lys Glu Lys Val Lys Lys Tyr Glu Gln Gly
    610             615             620

Arg Phe Asp Phe Gln Gly Ala Ala Leu Tyr Met Ser Pro Met Val Val
625             630             635             640

Leu Leu Leu Val Asn Ile Val Cys Phe Phe Gly Gly Leu Trp Arg Leu
            645             650             655

Phe Lys Glu Lys Asp Phe Ala Asp Met Phe Gly Gln Leu Phe Leu Leu
            660             665             670

Ser Tyr Val Met Ala Leu Ser Tyr Pro Ile Leu Glu Gly Ile Val Thr
            675             680             685

Met Lys Met Lys Ser Gly
    690
```

```
<210> SEQ ID NO 6
<211> LENGTH: 2085
<212> TYPE: DNA
<213> ORGANISM: Lotus japonicus

<400> SEQUENCE: 6
atggccaatt tcactctcca cacagaaacc gttcaagcat ggctccctct aagcagactc        60
cacattctta tacactcagt gttcgtcatc cttctcctct actaccgcac aacgcgtctc       120
atccacgcgc cgaccgcgcc gtggatcctg atgaccgttg cggaggctct cctcgccgtg       180
ctttggctct tcaaccaggc cttccggtgg cgaccggtga ccgctccgt gaagacagag        240 aagctgccgc gcgacgagaa tctccccggg ctggacatat ttgtgtgcac gattgatcct       300
gagaaggagc caacggcagg ggtgatggac acggttgttt ccgccgtggc gatggattac       360
ccgccggata agctatccgt gtatctttct gatgatggtg gttgcgccgt gacggagtat       420
gggattagag aggcttgtga gtttgccaag gtgtgggttc ctttttgtag aaagtatggg       480
atcaagtcga ggtgtccaaa agtttttcttc tctccgatgg gggaagatga agagattcta       540
aggacagatg agttcagagc agagcaagag aagatcaagg cccaatacga gactatgcag       600
aaaaacatcg agaaatttgg ttcagacccc aaaaattgtc gtattgtcac tgacagaccc       660
tctaagatcg agattataaa tgagcaatca gaaatcccac gtgttgtgta cgtctctcgt       720
gaaagaaggc catcacttcc tcacaagttc aaaggaggag ctctcaacac attgctcaga       780
gtgtcaggtc taatcagcaa tggaccttat gtgcttgcag tggattgtga tatgtattgc       840
aatgatccat cctctgccaa gcaagcaatg tgcttcttcc ttgatccaga acatctaaa        900 tacattgcat ttgtccaatt ccctcaaatg tttcacaacc ttagtaagaa agacatctat       960
gataatcaat ctaggactgc tttttaagaca atgtggcaag gcatggatgg actcagtggt      1020
ccaggtcttt ctggcagtgg taactacttg agtagaagtg cattgctatt tggaagtcca      1080
aaccaaaaag atgactatct gcttgatgct caaaactact ttggcgagtc tcccttgtac      1140
```

-continued

```
attgaatcat tgaaggccat ccgtggacaa caaactacca aaaagaatat ctcaagagac   1200
gaaagtttac tagaagctaa agtggtggcc tctgcttcct acgagacaaa cacagaatgg   1260
ggctcagagg ttggattctc atatggcatc ttactggaga gtactattac tggttacctt   1320
ttgcactgca gaggatggaa atcagcttat ctttacccaa aaacaccatg tttcttaggg   1380
tgtgccccca ctgacattaa agaaggcatg cttcagttgg tgaagtggtt gtctgagctt   1440
tgcttgtttg ctgtctctaa gtacagccct tttacatatg ggttttcaag attgcccatt   1500
atgcctacct tcacttattg tttcctggca gcttcatccc tatatgctat tgtcttcatc   1560
ctttatggca ttgtacctca agtgtgcttc ttgaaaggaa tccctgtgtt tccaaaggcc   1620
acagaccctt ggtttgcagt gtttgcagta ttgtatgtag ccacccagat tcaacatttg   1680
attgaagtcc tttctggcaa tggctcggtc tcgatgtggt gggatgaaca aagaatttgg   1740
attctgaagt cagttactag cgtatttgca atgatagagg gaatcaagaa atggttagga   1800
ttgaacaaga aaaaattcaa cctgtcaaac aaagcggttg acaaggagaa ggtcaagaaa   1860
tatgagcaag gtaggtttga tttccaagga gcagctctgt acatgtctcc aatggttgtg   1920
ttgctcctag tgaacattgt ttgcttcttt ggcggtttat ggagactgtt taaggagaaa   1980
gattttgcag atatgtttgg tcaacttttc ctactcagct atgtgatggc tctcagttat   2040
cccattcttg aggggatagt aactatgaaa atgaagagtg ggtag              2085
```

<210> SEQ ID NO 7
<211> LENGTH: 493
<212> TYPE: PRT
<213> ORGANISM: Glycyrrhiza uralensis

<400> SEQUENCE: 7

```
Met Glu Val His Trp Val Cys Met Ser Ala Ala Thr Leu Leu Val Cys
1               5                   10                  15

Tyr Ile Phe Gly Ser Lys Phe Val Arg Asn Leu Asn Gly Trp Tyr Tyr
            20                  25                  30

Asp Val Lys Leu Arg Arg Lys Glu His Pro Leu Pro Pro Gly Asp Met
        35                  40                  45

Gly Trp Pro Leu Ile Gly Asp Leu Leu Ser Phe Ile Lys Asp Phe Ser
    50                  55                  60

Ser Gly His Pro Asp Ser Phe Ile Asn Asn Leu Val Leu Lys Tyr Gly
65                  70                  75                  80

Arg Ser Gly Ile Tyr Lys Thr His Leu Phe Gly Asn Pro Ser Ile Ile
                85                  90                  95

Val Cys Glu Pro Gln Met Cys Arg Arg Val Leu Thr Asp Asp Val Asn
            100                 105                 110

Phe Lys Leu Gly Tyr Pro Lys Ser Ile Lys Glu Leu Ala Arg Cys Arg
        115                 120                 125

Pro Met Ile Asp Val Ser Asn Ala Glu His Arg Leu Phe Arg Arg Leu
    130                 135                 140

Ile Thr Ser Pro Ile Val Gly His Lys Ala Leu Ala Met Tyr Leu Glu
145                 150                 155                 160

Arg Leu Glu Glu Ile Val Ile Asn Ser Leu Glu Glu Leu Ser Ser Met
                165                 170                 175

Lys His Pro Val Glu Leu Leu Lys Glu Met Lys Lys Val Ser Phe Lys
            180                 185                 190

Ala Ile Val His Val Phe Met Gly Ser Ser Asn Gln Asp Ile Ile Lys
        195                 200                 205
```

```
Lys Ile Gly Ser Ser Phe Thr Asp Leu Tyr Asn Gly Met Phe Ser Ile
    210                 215                 220

Pro Ile Asn Val Pro Gly Phe Thr Phe His Lys Ala Leu Glu Ala Arg
225                 230                 235                 240

Lys Lys Leu Ala Lys Ile Val Gln Pro Val Val Asp Glu Arg Arg Leu
                245                 250                 255

Met Ile Glu Asn Gly Pro Gln Glu Gly Ser Gln Arg Lys Asp Leu Ile
                260                 265                 270

Asp Ile Leu Leu Glu Val Lys Asp Glu Asn Gly Arg Lys Leu Glu Asp
            275                 280                 285

Glu Asp Ile Ser Asp Leu Leu Ile Gly Leu Leu Phe Ala Gly His Glu
    290                 295                 300

Ser Thr Ala Thr Ser Leu Met Trp Ser Ile Thr Tyr Leu Thr Gln His
305                 310                 315                 320

Pro His Ile Leu Lys Lys Ala Lys Glu Glu Gln Glu Glu Ile Thr Arg
                325                 330                 335

Thr Arg Phe Ser Ser Gln Lys Gln Leu Ser Leu Lys Glu Ile Lys Gln
                340                 345                 350

Met Val Tyr Leu Ser Gln Val Ile Asp Glu Thr Leu Arg Cys Ala Asn
            355                 360                 365

Ile Ala Phe Ala Thr Phe Arg Glu Ala Thr Ala Asp Val Asn Ile Asn
    370                 375                 380

Gly Tyr Ile Ile Pro Lys Gly Trp Arg Val Leu Ile Trp Ala Arg Ala
385                 390                 395                 400

Ile His Met Asp Ser Glu Tyr Tyr Pro Asn Pro Glu Glu Phe Asn Pro
                405                 410                 415

Ser Arg Trp Asp Asp Tyr Asn Ala Lys Ala Gly Thr Phe Leu Pro Phe
                420                 425                 430

Gly Ala Gly Ser Arg Leu Cys Pro Gly Ala Asp Leu Ala Lys Leu Glu
            435                 440                 445

Ile Ser Ile Phe Leu His Tyr Phe Leu Arg Asn Tyr Arg Leu Glu Arg
    450                 455                 460

Ile Asn Pro Glu Cys His Val Thr Ser Leu Pro Val Ser Lys Pro Thr
465                 470                 475                 480

Asp Asn Cys Leu Ala Lys Val Ile Lys Val Ser Cys Ala
                485                 490
```

<210> SEQ ID NO 8
<211> LENGTH: 1482
<212> TYPE: DNA
<213> ORGANISM: Glycyrrhiza uralensis

<400> SEQUENCE: 8

```
atggaagtac attgggtttg catgtccgct gccactttgt tggtatgcta catttttgga        60
agcaagtttg tgaggaattt gaatgggtgg tattatgatg taaaactaag aaggaaagaa       120
cacccactac ccccaggtga catgggatgg cctcttatcg gcgatctatt gtccttcatc       180
aaagatttct catcgggtca ccctgattca ttcatcaaca accttgttct caaatatgga       240
cgaagtggta tctacaagac tcacttgttt gggaatccaa gcatcattgt ttgtgagcct       300
cagatgtgta ggcgagttct cactgatgat gtgaacttta gcttggttta ccaaaatct        360 atcaaagagt ggcacgatg tagacccatg attgatgtct ctaatgcgga acataggctt        420
tttcgacgcc tcattacttc cccaatcgtg ggtcacaagg cgctagcaat gtacctagag       480
```

```
cgtcttgagg aaattgtgat caattcgttg gaagaattgt ccagcatgaa gcaccccgtt      540
gagctcttga aagagatgaa gaaggtttcc tttaaagcca ttgtccacgt cttcatgggc      600
tcttccaatc aggacatcat taaaaaaatt ggaagttcgt ttactgattt gtacaatggc      660
atgttctcta tccccattaa cgtacctggt tttacattcc acaaagcact cgaggcacgt      720
aagaagctag ccaaaatagt tcaacccgtt gtggatgaaa ggcggttgat gatagaaaat      780
ggtccacaag aagggagcca agaaaaagat cttattgata ttcttttgga agtcaaagat      840
gagaatggac gaaaattgga ggacgaggat attagcgatt tattaatagg gctttttgttc      900 gctggccatg aaagtacagc aaccagttta atgtggtcaa ttacgtatct tacacagcat      960
ccccatatct tgaaaaaggc taaggaagag caggaagaaa taacgaggac aagatttttcc     1020 tcgcagaaac aattaagtct taaggaaatt aagcaaatgg tttatctttc tcaggtaatt     1080
gatgaaactt tacgatgtgc caatattgcc tttgcaactt ttcgagaggc aactgctgat     1140
gtgaacatca atggttatat cataccaaag ggatggagag tgctaatttg ggcaagagcc     1200
attcatatgg attctgaata ttacccaaat ccagaagaat ttaatccatc gagatgggat     1260
gattacaatg ccaaagcagg aaccttcctt cctttttggag caggaagtag actttgtcct     1320
ggagccgact tggcgaaact tgaaatttcc atatttcttc attatttcct ccgtaattac     1380
aggttggaga gaataaatcc agaatgtcac gttaccagct taccagtatc taaacccaca     1440
gacaattgtc tcgctaaggt gataaaggtt tcatgtgctt ag                        1482
```

<210> SEQ ID NO 9
<211> LENGTH: 523
<212> TYPE: PRT
<213> ORGANISM: Glycyrrhiza uralensis

<400> SEQUENCE: 9

```
Met Asp Ala Ser Ser Thr Pro Gly Ala Ile Trp Val Val Leu Thr Val
1               5                   10                  15

Ile Leu Ala Ala Ile Pro Ile Trp Val Cys His Met Val Asn Thr Leu
            20                  25                  30

Trp Leu Arg Pro Lys Arg Leu Glu Arg His Leu Arg Ala Gln Gly Leu
        35                  40                  45

His Gly Asp Pro Tyr Lys Leu Ser Leu Asp Asn Ser Lys Gln Thr Tyr
    50                  55                  60

Met Leu Lys Leu Gln Gln Glu Ala Gln Ser Lys Ser Ile Gly Leu Ser
65                  70                  75                  80

Lys Asp Asp Ala Ala Pro Arg Ile Phe Ser Leu Ala His Gln Thr Val
                85                  90                  95

His Lys Tyr Gly Lys Asn Ser Phe Ala Trp Glu Gly Thr Ala Pro Lys
            100                 105                 110

Val Ile Ile Thr Asp Pro Glu Gln Ile Lys Glu Val Phe Asn Lys Ile
        115                 120                 125

Gln Asp Phe Pro Lys Pro Lys Leu Asn Pro Ile Ala Lys Tyr Ile Ser
    130                 135                 140

Ile Gly Leu Val Gln Tyr Glu Gly Asp Lys Trp Ala Lys His Arg Lys
145                 150                 155                 160

Ile Ile Asn Pro Ala Phe His Leu Glu Lys Leu Lys Gly Met Leu Pro
                165                 170                 175

Ala Phe Ser His Ser Cys His Glu Met Ile Ser Lys Trp Lys Gly Leu
            180                 185                 190

Leu Ser Ser Asp Gly Thr Cys Glu Val Asp Val Trp Pro Phe Leu Gln
```

```
           195                 200                 205
Asn Leu Thr Cys Asp Val Ile Ser Arg Thr Ala Phe Gly Ser Ser Tyr
    210                 215                 220
Ala Glu Gly Ala Lys Ile Phe Glu Leu Leu Lys Arg Gln Gly Tyr Ala
225                 230                 235                 240
Leu Met Thr Ala Arg Tyr Ala Arg Ile Pro Leu Trp Trp Leu Leu Pro
                245                 250                 255
Ser Thr Thr Lys Arg Arg Met Lys Glu Ile Glu Arg Gly Ile Arg Asp
                260                 265                 270
Ser Leu Glu Gly Ile Ile Arg Lys Arg Glu Lys Ala Leu Lys Ser Gly
                275                 280                 285
Lys Ser Thr Asp Asp Asp Leu Leu Gly Ile Leu Leu Gln Ser Asn His
    290                 295                 300
Ile Glu Asn Lys Gly Asp Glu Asn Ser Lys Ser Ala Gly Met Thr Thr
305                 310                 315                 320
Gln Glu Val Met Glu Glu Cys Lys Leu Phe Tyr Leu Ala Gly Gln Glu
                325                 330                 335
Thr Thr Ala Ala Leu Leu Ala Trp Thr Met Val Leu Leu Gly Lys His
                340                 345                 350
Pro Glu Trp Gln Ala Arg Ala Arg Gln Glu Val Leu Gln Val Phe Gly
                355                 360                 365
Asn Gln Asn Pro Asn Phe Glu Gly Leu Gly Arg Leu Lys Ile Val Thr
    370                 375                 380
Met Ile Leu Tyr Glu Val Leu Arg Leu Tyr Pro Pro Gly Ile Tyr Leu
385                 390                 395                 400
Thr Arg Ala Leu Arg Lys Asp Leu Lys Leu Gly Asn Leu Leu Leu Pro
                405                 410                 415
Ala Gly Val Gln Val Ser Val Pro Ile Leu Leu Ile His His Asp Glu
                420                 425                 430
Gly Ile Trp Gly Asn Asp Ala Lys Glu Phe Asn Pro Glu Arg Phe Ala
                435                 440                 445
Glu Gly Ile Ala Lys Ala Thr Lys Gly Gln Val Cys Tyr Phe Pro Phe
    450                 455                 460
Gly Trp Gly Pro Arg Ile Cys Val Gly Gln Asn Phe Ala Leu Leu Glu
465                 470                 475                 480
Ala Lys Ile Val Leu Ser Leu Leu Leu Gln Asn Phe Ser Phe Glu Leu
                485                 490                 495
Ser Pro Thr Tyr Ala His Val Pro Thr Thr Val Leu Thr Leu Gln Pro
                500                 505                 510
Lys His Gly Ala Pro Ile Ile Leu His Lys Leu
    515                 520
```

```
<210> SEQ ID NO 10
<211> LENGTH: 1572
<212> TYPE: DNA
<213> ORGANISM: Glycyrrhiza uralensis

<400> SEQUENCE: 10
atggatgcat cttccacacc aggggctatc tgggttgttc tgacagtgat actagctgcg      60
attcccatat gggtatgcca tatggtgaac acgctgtggc tgaggccaaa gaggttggaa     120
aggcatctca gagctcaagg tcttcatggc gacccttaca agctctcact tgacaactcc     180
aagcaaacct atatgctcaa gttgcaacaa gaagcacaat caaaatccat tggtctctcc     240
aaagatgatg ctgcaccacg aatcttctcc cttgcccatc aaactgtaca caaatatgga     300
```

-continued

```
aagaactcct ttgcatggga agggacagca ccaaaggtga tcatcacaga cccagagcaa     360
attaaggaag tctttaacaa gattcaggac ttccccaaac caaaattaaa tcccatcgcc     420
aagtatatta gcatcggtct agtacagtat gagggtgaca atgggccaa acatcgaaag      480 attatcaatc cggcattcca cttagaaaaa ttgaaaggta tgctgccagc attttctcat     540
agctgccatg aaatgattag caaatggaag gggttattgt catcagatgg aacatgtgag     600
gttgatgttt ggcccttcct tcaaaatctc acttgtgatg taatttctag gacggcattc     660
ggaagcagct atgcagaagg agcaaaaata tttgaacttt tgaaaaggca gggatatgct     720
ttgatgacag cacgatacgc acgcattcca ttatggtggc ttctaccatc aactaccaaa     780
aggaggatga aggaaattga aagaggcata cgtgattcac ttgaaggtat cattagaaaa     840
cgagaaaaag cattgaagag tggcaaaagc accgatgacg acttattagg catactttg     900 caatcaaatc acattgaaaa taaaggagat gaaaacagta agagtgctgg aatgaccacc     960
caagaagtaa tggaggaatg caaacttttt tacctggcag ggcaagagac caccgcggct    1020
ttgctggcct ggacaatggt gttattaggc aagcatcctg aatggcaagc acgtgcaagg    1080
caggaagttt tgcaagtttt tgggaatcaa aatccaaact tcgaagggtt aggtcgcctc    1140
aaaattgtaa ccatgatttt atatgaggta ctcaggctgt acccacctgg gatttacctc    1200
acccgagctc ttcgaaagga tttgaaactt ggaaaccttt tgctacctgc tggagtacag    1260
gtttccgtac caatactttt gattcaccat gatgaaggta tatggggcaa tgatgcaaag    1320
gagttcaatc ctgaaaggtt tgctgaagga attgcaaagg caacaaaagg ccaagtttgc    1380 tatttcccctt ttggatgggg tcctagaata tgtgttgggc aaaactttgc cttattagaa    1440
gccaagattg tattgtcatt gctgctgcag aatttctcat ttgagctatc tccgacttat    1500
gcacatgttc ctaccacggt gcttactttg cagccaaaac atggggcacc catcattctg    1560
cataaactgt aa                                                        1572
```

<210> SEQ ID NO 11
<211> LENGTH: 523
<212> TYPE: PRT
<213> ORGANISM: Glycyrrhiza glabra

<400> SEQUENCE: 11

```
Met Asp Ala Ser Ser Thr Pro Gly Ala Ile Trp Val Val Leu Thr Val
1               5                   10                  15

Ile Leu Ala Ala Ile Pro Ile Trp Ala Cys His Met Val Asn Thr Leu
            20                  25                  30

Trp Leu Arg Pro Lys Arg Leu Glu Arg His Leu Arg Ala Gln Gly Leu
        35                  40                  45

His Gly Asp Pro Tyr Lys Leu Ser Leu Asp Asn Ser Lys Gln Ile Tyr
    50                  55                  60

Met Leu Lys Leu Gln Gln Glu Ala Gln Ser Lys Ser Ile Gly Leu Ser
65                  70                  75                  80

Lys Asp Asp Ala Ala Pro Arg Ile Phe Ser Leu Ala His Gln Thr Val
                85                  90                  95

His Lys Tyr Gly Lys Asn Ser Phe Ala Trp Glu Gly Thr Thr Pro Lys
            100                 105                 110

Val Ile Ile Thr Asp Pro Glu Gln Ile Lys Glu Val Phe Asn Lys Ile
        115                 120                 125

Gln Asp Phe Pro Lys Pro Lys Leu Asn Pro Ile Ala Lys Tyr Ile Ser
    130                 135                 140
```

-continued

```
Ile Gly Leu Val His Tyr Glu Gly Asp Lys Trp Ala Lys His Arg Lys
145                 150                 155                 160

Ile Ile Asn Pro Ala Phe His Leu Glu Lys Leu Lys Gly Met Leu Pro
                165                 170                 175

Ala Phe Ser His Ser Cys His Glu Met Ile Ser Lys Trp Lys Gly Leu
            180                 185                 190

Leu Ser Val Asp Gly Thr Cys Glu Val Asp Val Trp Pro Phe Leu Gln
            195                 200                 205

Asn Leu Thr Cys Asp Val Ile Ser Arg Thr Ala Phe Gly Ser Ser Tyr
        210                 215                 220

Ala Glu Gly Ala Ile Ile Phe Glu Leu Leu Lys Arg Gln Gly Tyr Ala
225                 230                 235                 240

Leu Met Thr Ala Arg Tyr Ala Arg Ile Pro Leu Trp Trp Leu Leu Pro
                245                 250                 255

Ser Thr Thr Lys Arg Arg Met Lys Glu Ile Glu Arg Gly Ile Arg Asp
                260                 265                 270

Ser Leu Glu Gly Ile Ile Arg Lys Arg Glu Lys Ala Leu Lys Ser Gly
            275                 280                 285

Lys Ser Thr Asp Asp Asp Leu Leu Gly Ile Leu Leu Gln Ser Asn His
        290                 295                 300

Ile Glu Asn Lys Gly Asp Glu Asn Ser Lys Ser Ala Gly Met Thr Thr
305                 310                 315                 320

Gln Glu Val Met Glu Glu Cys Lys Leu Phe Tyr Leu Ala Gly Gln Glu
                325                 330                 335

Thr Thr Ala Ala Leu Leu Ala Trp Thr Met Val Leu Leu Gly Lys His
                340                 345                 350

Pro Glu Trp Gln Ala Arg Ala Arg Gln Glu Val Leu Gln Val Phe Gly
            355                 360                 365

Asn Gln Asn Pro Asn Phe Glu Gly Leu Gly Arg Leu Lys Ile Val Thr
        370                 375                 380

Met Ile Leu Tyr Glu Val Leu Arg Leu Tyr Pro Pro Gly Ile Tyr Leu
385                 390                 395                 400

Thr Arg Ala Leu Gln Lys Asp Leu Lys Leu Gly Asn Leu Leu Leu Pro
                405                 410                 415

Ala Gly Val Gln Val Ser Val Pro Ile Leu Leu Ile His His Asp Glu
                420                 425                 430

Gly Ile Trp Gly Asn Asp Ala Lys Glu Phe Asn Pro Glu Arg Phe Ala
            435                 440                 445

Glu Gly Ile Ala Lys Ala Thr Lys Gly Gln Val Cys Tyr Phe Pro Phe
        450                 455                 460

Gly Trp Gly Pro Arg Ile Cys Val Gly Gln Asn Phe Ala Leu Leu Glu
465                 470                 475                 480

Ala Lys Ile Val Leu Ser Leu Leu Leu Gln Asn Phe Ser Phe Glu Leu
                485                 490                 495

Ser Pro Ser Tyr Ala His Val Pro Thr Thr Val Leu Thr Leu Gln Pro
            500                 505                 510

Lys His Gly Ala Pro Ile Ile Leu His Lys Leu
        515                 520
```

<210> SEQ ID NO 12
<211> LENGTH: 1572
<212> TYPE: DNA
<213> ORGANISM: Glycyrrhiza glabra -continued

```
<400> SEQUENCE: 12
atggatgcat cttccacacc aggggctatc tgggttgttc taacagtgat actagctgcg      60
attcccatat gggcatgcca tatggtcaac acgctgtggc tgaggccaaa gaggttggaa     120
aggcatctca gagctcaagg tcttcatggt gacccttaca agctctcact tgacaactcc     180
aagcaaatct atatgctcaa gttgcaacaa gaagcacaat caaaatccat tggtctctcc     240
aaagatgatg ctgcaccacg aatcttctcc cttgcccatc aaactgtaca caaatatgga     300
aagaactcct ttgcatggga agggacaaca ccaaaggtga tcatcacaga cccagagcaa     360
attaaggaag tctttaacaa gattcaggac ttccccaaac caaaattaaa tcccatcgcc     420
aagtatatta gcatcggtct agtacattat gagggtgaca atgggccaa  acatcgaaag     480 attatcaatc cggcattcca cttagaaaaa ttgaaaggta tgctgccagc attttctcat     540
agctgccatg aaatgattag caaatggaag gggttattgt cagtagatgg aacgtgtgag     600
gttgatgttt ggcccttcct tcaaaatctc acttgtgatg taatttctag gacggcattc     660
ggaagcagct atgcagaagg agcaataata tttgaacttt tgaaaaggca gggatatgct     720
ttgatgacag cacgatacgc gcgcattcca ttatggtggc ttctaccatc aactaccaaa     780
aggaggatga aggaaattga aagaggcata cgtgattcac ttgaaggtat cattagaaaa     840
cgagaaaaag cattgaagag tggcaaaagc accgatgacg acttattagg catacttttg     900
caatcaaatc acattgaaaa taaaggagat gaaaacagta agagtgctgg aatgaccacc     960
caagaagtaa tggaggaatg caaactttt  tacctggcag ggcaagagac caccgcggct    1020
ttgctggcct ggacaatggt gttattaggc aagcatcctg aatggcaagc acgtgcaagg    1080
caggaagttt tgcaagtttt tgggaatcaa aatccaaact tcgaagggtt aggtcgcctc    1140
aaaattgtaa ccatgatttt tatatgaggta ctcaggctgt acccacctgg gatttacctc    1200
acccgagctc ttcaaaagga tttgaaactt ggaaaccttt tgctacctgc tggagtacag    1260
gtttccgtac caatactttt gattcaccat gatgaaggta tatggggcaa tgatgcaaag    1320
gagttcaatc ctgaaaggtt tgctgaagga attgcaaagg caacaaaagg ccaagtttgc    1380
tatttccctt ttggatgggg tcctagaata tgtgttgggc aaaactttgc cttattagaa    1440
gccaagattg tattgtcatt gctgctgcag aatttctcat ttgagttatc tccgagttat    1500
gcacatgttc ctaccacggt gcttactttg cagccaaaac atggggcacc catcattctg    1560
cataaactgt aa                                                        1572

<210> SEQ ID NO 13
<211> LENGTH: 524
<212> TYPE: PRT
<213> ORGANISM: Medicago truncatula

<400> SEQUENCE: 13

Met Glu Val Phe Met Phe Pro Thr Gly Thr Thr Val Ile Ile Ser Val
1               5                   10                  15

Leu Ser Val Leu Leu Ala Val Ile Pro Trp Tyr Leu Leu Asn Lys Leu
            20                  25                  30

Trp Leu Lys Pro Lys Arg Phe Glu Lys Leu Leu Lys Ala Gln Gly Phe
        35                  40                  45

Gln Gly Glu Pro Tyr Asn Leu Ser Val Leu Lys Asp Lys Ser Lys Gln
    50                  55                  60

Asn Tyr Met Leu Lys Leu Gln Gln Glu Asp Lys Ser Lys Ser Ile Gly
65                  70                  75                  80
```

```
Leu Ser Lys Glu Ala Ala Pro Ser Ile Phe Thr Pro Val His Gln Thr
            85                  90                  95

Val Arg Lys Tyr Gly Asn Asn Ser Phe Leu Trp Glu Gly Thr Thr Pro
            100                 105                 110

Arg Val Ile Ile Thr Asp Pro Asp Gln Ile Lys Asp Val Phe Asn Lys
            115                 120                 125

Ile Asp Asp Phe Pro Lys Pro Lys Leu Arg Ser Ile Ala Lys Tyr Leu
    130                 135                 140

Ser Val Gly Ile Leu Asp His Glu Gly Lys Lys Trp Ala Lys His Arg
145                 150                 155                 160

Lys Ile Ala Asn Pro Ala Phe His Leu Glu Lys Leu Lys Val Met Leu
                165                 170                 175

Pro Ala Phe Ser His Ser Cys Asn Glu Met Ile Ser Lys Trp Lys Glu
            180                 185                 190

Leu Leu Ser Ser Asp Gly Thr Cys Glu Ile Asp Val Trp Pro Ser Leu
            195                 200                 205

Gln Asn Phe Thr Cys Asp Val Ile Ser Arg Thr Ala Phe Gly Ser Ser
    210                 215                 220

Tyr Ala Glu Gly Thr Lys Leu Phe Gln Leu Leu Lys Lys Gln Gly Phe
225                 230                 235                 240

Leu Leu Met Thr Gly Arg His Thr Asn Asn Pro Leu Trp Gly Leu Leu
                245                 250                 255

Ala Thr Thr Thr Lys Thr Lys Met Lys Glu Ile Asp Arg Glu Ile His
            260                 265                 270

Asp Ser Leu Glu Gly Ile Ile Glu Lys Arg Glu Lys Ala Leu Lys Asn
            275                 280                 285

Gly Glu Thr Thr Asn Asp Asp Leu Leu Gly Ile Leu Leu Gln Ser Asn
    290                 295                 300

His Ala Glu Lys Gln Gly Gln Gly Asn Ser Lys Asn Ile Gly Met Thr
305                 310                 315                 320

Thr Gln Asp Val Ile Asp Glu Cys Lys Leu Phe Tyr Leu Ala Gly Gln
                325                 330                 335

Glu Thr Thr Ser Ser Leu Leu Val Trp Thr Met Val Leu Leu Gly Arg
            340                 345                 350

Tyr Pro Glu Trp Gln Ala Arg Ala Arg Glu Glu Val Leu Gln Val Phe
            355                 360                 365

Gly Asn Gln Asn Pro Asn Asn Glu Gly Leu Ser Gln Leu Lys Ile Val
    370                 375                 380

Thr Met Ile Leu Tyr Glu Val Leu Arg Leu Phe Pro Pro Leu Ile Tyr
385                 390                 395                 400

Phe Asn Arg Ala Leu Arg Lys Asp Leu Lys Leu Gly Asn Leu Leu Leu
                405                 410                 415

Pro Glu Gly Thr Gln Ile Ser Leu Pro Ile Leu Leu Ile His Gln Asp
            420                 425                 430

His Asp Leu Trp Gly Asp Asp Ala Lys Glu Phe Lys Pro Glu Arg Phe
            435                 440                 445

Ala Glu Gly Ile Ala Lys Ala Thr Lys Gly Gln Val Ser Tyr Phe Pro
    450                 455                 460

Phe Gly Trp Gly Pro Arg Ile Cys Leu Gly Gln Asn Phe Ala Leu Leu
465                 470                 475                 480

Glu Ala Lys Ile Ala Val Ser Leu Leu Leu Gln Asn Phe Ser Phe Glu
                485                 490                 495

Leu Ser Pro Asn Tyr Val His Val Pro Thr Thr Val Leu Thr Leu Gln
```

-continued

```
            500             505             510

Pro Lys Asn Gly Ala Ser Ile Ile Leu His Lys Leu
        515             520

<210> SEQ ID NO 14
<211> LENGTH: 1575
<212> TYPE: DNA
<213> ORGANISM: Medicago truncatula

<400> SEQUENCE: 14
atggaagtgt ttatgtttcc cacaggaaca acagtaatca tctctgttct ttcagttcta     60
cttgctgtga ttccatggta tcttctcaac aagttatggc ttaagccaaa gaggtttgag    120
aaacttctca agctcaagg ttttcaaggt gaaccttata acctttcagt attaaaggac     180
aaatcaaaac aaaattatat gttgaagttg caacaagaag ataaatctaa atccattggt    240
ctctccaaag aagctgcacc gtctatcttc actcctgttc atcaaactgt acgcaaatat    300
ggaaacaatt cctttttatg ggaaggtaca acaccaaggg ttatcatcac agaccctgat    360
caaattaagg atgtatttaa caagattgat gacttcccca aaccaaaact aagatccatc    420
gccaagtatt tgagcgttgg tatactagat catgagggta agaaatgggc taaacatagg    480
aagatcgcca atccagcatt ccacctagaa aaattgaaag ttatgctgcc tgcattttct    540
cacagttgca atgaaatgat aagcaaatgg aaggaactat tgtcatcaga tggaacatgt    600
gagattgatg tttggccttc ccttcagaat tttacctgtg atgtaatttc tcggacggca    660
tttggaagca gctacgcaga aggaacaaaa ctatttcaac ttctaaagaa gcagggattt    720
cttttgatga cagggcgaca cacgaacaat ccattatggg ggcttctagc aacaactacc    780
aagacgaaga tgaaagaaat tgatagagaa atccatgatt cacttgaggg aatcattgaa    840
aaacgagaaa aagcactgaa gaatggtgaa accaccaatg acgatttatt aggcattctt    900
ttgcaatcaa atcatgccga aaacaagga caaggaaata gtaagaatat tgggatgacc    960
acccaagatg tgatagatga atgcaaattg ttttaccttg ctgggcaaga gacgacttca   1020
agtttgctgg tttggacaat ggtgttatta ggcaggtatc ctgaatggca agcacgtgca   1080
agggaggaag ttttgcaagt ttttgggaac caaaatccta acaacgaagg attaagtcaa   1140
cttaaaattg ttaccatgat tttgtacgag gtactaaggt tattcccacc tttaatttac   1200
ttcaaccgag ctcttcgaaa ggatttgaaa cttggaaacc ttttgctacc tgaaggaaca   1260
caaatttccc taccaatact attgattcac aagatcatg atctatgggg tgatgatgca   1320
aaggagttca aacctgaaag gtttgctgaa ggaattgcga aggcaacaaa aggacaagtt   1380
tcttatttcc ctttttggatg gggtcctaga atttgtcttg acaaaacttt gccttatta   1440 gaagcaaaga tagcagtatc attgttgctg cagaatttct cattcgaact ttctccaaat   1500
tatgtgcatg ttcctaccac ggtgcttact ttgcagccaa aaaatggggc aagcatcatt   1560
ttgcataaac tgtaa                                                   1575

<210> SEQ ID NO 15
<211> LENGTH: 506
<212> TYPE: PRT
<213> ORGANISM: Glycyrrhiza uralensis

<400> SEQUENCE: 15

Met Asp Ser Phe Gly Val Glu Gly Asp His Gln Ala Asp Thr Thr Val
1               5                   10                  15

Leu Lys Ala Val Phe Leu Pro Phe Ile Ser Lys Ser His Leu Ile Arg
```

-continued

```
            20                  25                  30
Val Val Asp Lys Ala Arg Ile Phe Ala Met His Gly Val Asp Val Thr
            35                  40                  45
Ile Ile Thr Thr Pro Ala Asn Ala Ala Ala Phe Gln Thr Ser Ile Asp
        50                  55                  60
His Asp Ser Ser Arg Ser Arg Ser Ile Lys Thr His Ile Val Pro Phe
65                  70                  75                  80
Pro Gln Val Pro Gly Leu Pro Gln Gly Phe Glu Arg Leu Asp Ala Asp
                85                  90                  95
Thr Pro Gln His Leu Leu Pro Lys Ile Tyr Gln Gly Leu Ser Ile Leu
                100                 105                 110
Gln Glu Gln Phe Gln Gln Leu Phe Arg Glu Met Arg Pro Asp Phe Ile
            115                 120                 125
Val Thr Asp Met Tyr Tyr Pro Trp Ser Val Asp Ala Ala Ala Glu Leu
        130                 135                 140
Gly Ile Pro Arg Leu Val Cys Asn Gly Gly Ser Tyr Phe Ala Gln Ser
145                 150                 155                 160
Ala Val Asn Ser Ile Glu Leu Phe Ser Pro Gln Ala Lys Val Asp Ser
                165                 170                 175
Asn Thr Glu Thr Phe Leu Leu Pro Gly Leu Pro His Glu Val Glu Met
                180                 185                 190
Thr Arg Leu Gln Leu Pro Asp Trp Leu Arg Gly Ala Pro Asn Glu Tyr
            195                 200                 205
Thr Tyr Leu Met Lys Met Ile Lys Asp Ser Glu Arg Lys Ser Tyr Gly
        210                 215                 220
Ser Leu Phe Asn Ser Phe Tyr Glu Leu Glu Gly Thr Tyr Glu Glu His
225                 230                 235                 240
Tyr Lys Lys Ala Met Gly Thr Lys Ser Trp Ser Val Gly Pro Val Ser
                245                 250                 255
Leu Trp Val Asn Gln Asp Ala Ser Asp Lys Ala Cys Arg Gly Asp Val
                260                 265                 270
Lys Glu Gly Lys Gly Asp Gly Val Val Leu Thr Trp Leu Asp Ser Lys
            275                 280                 285
Thr Glu Asp Ser Val Leu Tyr Val Ser Phe Gly Ser Met Asn Lys Phe
        290                 295                 300
Pro Lys Thr Gln Leu Val Glu Ile Ala His Ala Leu Glu Asp Ser Gly
305                 310                 315                 320
His Asp Phe Ile Trp Val Val Gly Lys Ile Glu Glu Gly Glu Gly Gly
                325                 330                 335
Ala Asp Phe Leu Arg Glu Phe Glu Lys Lys Val Lys Glu Lys Asn Arg
                340                 345                 350
Gly Tyr Leu Ile Trp Gly Trp Ala Pro Gln Leu Leu Ile Leu Glu His
            355                 360                 365
Pro Ala Val Gly Ala Val Val Thr His Cys Gly Trp Asn Thr Val Met
        370                 375                 380
Glu Ser Val Asn Ala Ser Leu Pro Leu Ala Thr Trp Pro Leu Phe Ala
385                 390                 395                 400
Glu Gln Phe Phe Asn Glu Lys Leu Val Val Asp Val Val Lys Ile Gly
                405                 410                 415
Val Pro Val Gly Val Lys Glu Trp Arg Asn Trp Asn Glu Phe Gly Asp
                420                 425                 430
Glu Val Val Lys Arg Glu Asp Ile Gly Lys Ala Ile Ala Phe Leu Met
            435                 440                 445
```

-continued

```
Gly Gly Gly Asp Glu Ser Leu Glu Met Arg Lys Arg Val Lys Val Leu
    450                 455                 460

Ser Gly Ala Thr Lys Lys Ala Ile Gln Val Asp Gly Ser Ser Tyr Thr
465                 470                 475                 480

Lys Leu Lys Glu Leu Ile Glu Glu Leu Lys Ser Ile Lys Leu Gln Lys
                485                 490                 495

Val Asn Asn Lys Leu Met Glu Ala Val Ala
            500                 505
```

<210> SEQ ID NO 16
<211> LENGTH: 1521
<212> TYPE: DNA
<213> ORGANISM: Glycyrrhiza uralensis

<400> SEQUENCE: 16

```
atggactcct ttggggttga aggtgatcac caagccgaca ccacagtgct gaaggcggtt        60
tttcttccct tcatctcgaa aagtcatctc atccgtgtgg tggacaaagc aaggatcttc       120
gccatgcacg gcgtggatgt caccatcatc actacgccgg ccaacgctgc cgcttttccaa      180 acctccattg accacgactc cagccgcagc cgttccatca aaacgcacat cgttccgttc       240
ccccaagtac ccggtctgcc acagggattc gagagactcg atgccgacac tcctcaacac       300
ttgctcccca agatctacca ggggctatcc attctgcaag agcaattcca caactgttc        360 cgtgaaatga gaccagattt catagtcact gacatgtact acccttggag cgtcgatgcc       420
gccgccgagt ggggattcc gaggttggtt tgtaacggtg gaagctactt cgctcagtca       480
gctgttaact ccattgagct attttcacca caagccaagg ttgattcaaa taccgagact       540
tttctgcttc ctgggttacc ccatgaggtt gagatgacac gtttgcaact accggattgg       600
cttagaggag caccgaatga gtacacctat ttgatgaaga tgatcaagga ttcagagagg       660
aagagttatg ggtcattgtt caatagcttt tatgagcttg aagggactta tgaggagcat       720
tacaagaaag ccatgggaac caagagttgg agtgtggggc cagtttcttt gtgggtgaac       780
caagatgctt ctgataaggc ttgtaggggg gatgttaaag aaggaaaagg agatggggtg       840
gtgcttactt ggctggattc taaaacagag gactctgttt tgtatgtgag tttttgggagc      900 atgaacaagt tccctaaaac tcagcttgtt gagatagctc atgccctcga agattctggc       960
catgatttca tttgggtcgt tggcaaaatt gaagaaggtg aaggtggtgc tgatttttttg     1020 agggaatttg agaagaaagt gaaagaaaaa aacagaggtt atctgatatg gggttgggca      1080
ccacagcttg tgattctgga gcatcctgcg gttggagcag tggtgactca ttgtgggtgg      1140
aacaccgtta tggaaagtgt gaatgcaagt ttgccattgg caacttggcc attgtttgcg      1200
gagcagttct tcaatgagaa gctagtggtt gatgtggtga agattggtgt gccagttggg      1260
gttaaggaat ggagaaattg gaatgagttt ggggatgagg ttgtgaagag ggaggacata      1320
ggaaaggcca ttgcttttttt gatggtggt ggagatgagt ccttggaaat gaggaagagg      1380
gtcaaggtgc tcagtggtgc tacaaagaag gctattcagg ttgatgggtc ttcttacacc      1440
aagttgaaag aactcattga ggagctcaag tcaattaagc ttcaaaaggt caacaacaaa     1500
ttaatggagg cagtggctta a                                              1521
```

<210> SEQ ID NO 17
<211> LENGTH: 37
<212> TYPE: DNA
<213> ORGANISM: Artificial
<220> FEATURE:

-continued

<223> OTHER INFORMATION: primer

<400> SEQUENCE: 17
aaaaagcagg ctatggcaat gttcacgtac cacgttg                                37

<210> SEQ ID NO 18
<211> LENGTH: 45
<212> TYPE: DNA
<213> ORGANISM: Artificial
<220> FEATURE:
<223> OTHER INFORMATION: primer

<400> SEQUENCE: 18
agaaagctgg gtctatccac ttttgctttt cattgttact atggc               45

<210> SEQ ID NO 19
<211> LENGTH: 25
<212> TYPE: DNA
<213> ORGANISM: Artificial
<220> FEATURE:
<223> OTHER INFORMATION: primer

<400> SEQUENCE: 19
caccatggca agcttcaccc ttcac                                     25

<210> SEQ ID NO 20
<211> LENGTH: 23
<212> TYPE: DNA
<213> ORGANISM: Artificial
<220> FEATURE:
<223> OTHER INFORMATION: primer

<400> SEQUENCE: 20
ttatccactc ttgctttttca tgg                                      23

<210> SEQ ID NO 21
<211> LENGTH: 37
<212> TYPE: DNA
<213> ORGANISM: Artificial
<220> FEATURE:
<223> OTHER INFORMATION: primer

<400> SEQUENCE: 21
gggcggccgc actagaaaaa tggtgaagat atgttgt                        37

<210> SEQ ID NO 22
<211> LENGTH: 33
<212> TYPE: DNA
<213> ORGANISM: Artificial
<220> FEATURE:
<223> OTHER INFORMATION: primer

<400> SEQUENCE: 22
atccatcgat actagttagg caacggcagg cat                            33

<210> SEQ ID NO 23
<211> LENGTH: 15
<212> TYPE: DNA
<213> ORGANISM: Artificial
<220> FEATURE:
<223> OTHER INFORMATION: synthetic

<400> SEQUENCE: 23
gggcggccgc actag                                                15

-continued

```
<210> SEQ ID NO 24
<211> LENGTH: 15
<212> TYPE: DNA
<213> ORGANISM: Artificial
<220> FEATURE:
<223> OTHER INFORMATION: synthetic

<400> SEQUENCE: 24
atccatcgat actag                                                      15

<210> SEQ ID NO 25
<211> LENGTH: 1443
<212> TYPE: DNA
<213> ORGANISM: Arabidopsis thaliana

<400> SEQUENCE: 25
atggtgaaga tatgttgtat tggagctggg tatgttggtg gaccaacaat ggcagtgatt      60
gcattgaaat gtccagacgt tgaagtagcg gttgttgata tctctgtacc acgtatcaac     120
gcttggaaca gtgacacgct tccgatttac gagcctggtc ttgatgatgt tgtgaagcaa     180
tgccgtggca agaacctttt ctttagtact gatgttgaga aacatgttag ggaagctgat     240
attgtgtttg tttctgtcaa cacaccgact aagactagag gtcttggtgc tggtaaagct     300
gcggatctta cgtactggga gagcgctgcg cgtatgatcg ctgatgtttc ggtatcggat     360
aagattgtcg ttgagaaatc gactgttccg gttaaaacag ctgaagctat tgagaagatt     420
ttgacacata acagtaaagg gattaagttt cagattcttt cgaatcccga gtttttggcg     480
gaaggaaccg cgattaagga cctatttaat ccggaccgtg ttcttatcgg agggcgggaa     540
accccagaag ggtttaaagc ggtgcagact ctcaagaatg tgtatgcaca ctgggttcct     600
gaaggccaaa tcataacaac caatctctgg tctgctgagc tgtccaagct tgcggcaaac     660
gctttcttgg ctcaaaggat ttcatcagtg aatgctatgt cggctctgtg tgaagccaca     720
ggcgcagatg tcacgcaagt gtcttacgcg gttggtacag actcaaggat tggtcccaag     780
ttcttgaact cgagtgttgg attcggtggt tcgtgtttcc agaaggacat tctgaatctt     840
gtctacatct gtgagtgcaa cggactcccg gaagtggcag agtactggaa gcaagtcatc     900
aagatcaatg actaccagaa gagccggttc gtgaaccgtg ttgtttcctc catgttcaac     960
tctgtatcaa acaagaagat tgcggttctc ggtttcgcat tcaagaaaga caccggtgac    1020
acaagggaga ctccagccat cgatgtgtgc aagggtcttt tagaagacaa agcaaggcta    1080
agcatttacg acccacaagt gactgaggat cagatccaga gggatttatc catgaacaag    1140
ttcgactggg accatcctct acatttgcag ccaatgagcc caacaacagt gaaacaagtg    1200
accgttactt gggacgcata cgaagcaact aaggacgctc acggtatctg catcatgacc    1260
gagtgggatg agttcaagaa ccttgatttc cagaagatct ttgacaacat gcagaaacca    1320
gctttcgtgt tcgatggaag aaacattatg aatctgcaaa agctaaggga gattggtttc    1380
attgtttact ccattggtaa gcctctcgac gactggctca aggacatgcc tgccgttgcc    1440
taa                                                                   1443

<210> SEQ ID NO 26
<211> LENGTH: 24
<212> TYPE: DNA
<213> ORGANISM: Artificial
<220> FEATURE:
<223> OTHER INFORMATION: primer

<400> SEQUENCE: 26
```

```
gcggctaggc ttgcgctcaa tttt                                              24

<210> SEQ ID NO 27
<211> LENGTH: 24
<212> TYPE: DNA
<213> ORGANISM: Artificial
<220> FEATURE:
<223> OTHER INFORMATION: primer

<400> SEQUENCE: 27
tgcctgtttg gacacacaac cgtg                                              24

<210> SEQ ID NO 28
<211> LENGTH: 24
<212> TYPE: DNA
<213> ORGANISM: Artificial
<220> FEATURE:
<223> OTHER INFORMATION: primer

<400> SEQUENCE: 28
cgttggttgc tgctggccta acac                                              24

<210> SEQ ID NO 29
<211> LENGTH: 25
<212> TYPE: DNA
<213> ORGANISM: Artificial
<220> FEATURE:
<223> OTHER INFORMATION: primer

<400> SEQUENCE: 29
ccgccaaaga agcaaacaat gttca                                             25

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
ccatggcggt tccgtgaatc ttagg                                             25

<210> SEQ ID NO 31
<211> LENGTH: 33
<212> TYPE: DNA
<213> ORGANISM: Artificial
<220> FEATURE:
<223> OTHER INFORMATION: primer

<400> SEQUENCE: 31
aaaaagcagg ctatggcaag cttcaccctt cac                                    33

<210> SEQ ID NO 32
<211> LENGTH: 35
<212> TYPE: DNA
<213> ORGANISM: Artificial
<220> FEATURE:
<223> OTHER INFORMATION: primer

<400> SEQUENCE: 32
agaaagctgg gtttatccac tcttgctttt catgg                                  35

<210> SEQ ID NO 33
<211> LENGTH: 33
<212> TYPE: DNA
<213> ORGANISM: Artificial
```

```
<220> FEATURE:
<223> OTHER INFORMATION: primer

<400> SEQUENCE: 33
aaaaagcagg ctatggccaa tttcactctc cac                                      33

<210> SEQ ID NO 34
<211> LENGTH: 35
<212> TYPE: DNA
<213> ORGANISM: Artificial
<220> FEATURE:
<223> OTHER INFORMATION: primer

<400> SEQUENCE: 34
agaaagctgg gtctacccac tcttcatttt catag                                    35

<210> SEQ ID NO 35
<211> LENGTH: 12
<212> TYPE: DNA
<213> ORGANISM: Artificial
<220> FEATURE:
<223> OTHER INFORMATION: synthetic

<400> SEQUENCE: 35
aaaaagcagg ct                                                             12

<210> SEQ ID NO 36
<211> LENGTH: 12
<212> TYPE: DNA
<213> ORGANISM: Artificial
<220> FEATURE:
<223> OTHER INFORMATION: synthetic

<400> SEQUENCE: 36
agaaagctgg gt                                                             12

<210> SEQ ID NO 37
<211> LENGTH: 22
<212> TYPE: DNA
<213> ORGANISM: Artificial
<220> FEATURE:
<223> OTHER INFORMATION: primer

<400> SEQUENCE: 37
caccatggcc aatttcactc tc                                                  22

<210> SEQ ID NO 38
<211> LENGTH: 23
<212> TYPE: DNA
<213> ORGANISM: Artificial
<220> FEATURE:
<223> OTHER INFORMATION: primer

<400> SEQUENCE: 38
ctacccactc ttcattttca tag                                                 23

<210> SEQ ID NO 39
<211> LENGTH: 25
<212> TYPE: DNA
<213> ORGANISM: Artificial
<220> FEATURE:
<223> OTHER INFORMATION: primer

<400> SEQUENCE: 39
caccatggca gaattcagtc ttcac                                               25
```

```
<210> SEQ ID NO 40
<211> LENGTH: 23
<212> TYPE: DNA
<213> ORGANISM: Artificial
<220> FEATURE:
<223> OTHER INFORMATION: primer

<400> SEQUENCE: 40
ttacccactc ttgcttttca tag                                               23

<210> SEQ ID NO 41
<211> LENGTH: 2097
<212> TYPE: DNA
<213> ORGANISM: Astragalus sinicus

<400> SEQUENCE: 41
atggcagaat tcagtcttca cacagaaact gttcaatcat ggttaccact aagcagagct        60
cacataatat tccacttcgc atgcgtctta ttactcttct actacagaat cacacgtttc       120
ataccaacac taccatccat tcttatgata gcagctgagt ttatcctttc tgtcttatgg       180
ttcttcaacc aagcatacag gtggcgtcct gttagcaggt ctgtcaaaac acaaaactta       240
ccaaaagatg aaaatcttcc aggattggat atatttgtgt gcaccattga tcctgagaag       300
gaacctacgg ttgaagttat gaatactctt gtttctgcta tttcaatgga ttatcctcct       360
cataaacttt ctgtttatct ttctgatgat ggagctgctc ctgttacttt ttatgggatt       420
aaagaggctt ctgaatttgc aaaggtttgg gtaccttttt gtaataaata tggtgttaag       480
tctaggtgtc ctaaggtttt cttctctcct cttgctgaag atgaacttgt tcctctaagg       540
acacatcaat tcgaggatga caaagaggac atcaaggtta aatacgacaa aatgcagaaa       600
aacattgaaa aatttggttc agaaccaaaa aatgtcagta tggtgaccga cagacctgct       660
cggatcgaga ttataagtga tgaaccagaa atggcacgtg ttgtttatgt gtctcgtgaa       720
agaagaccat cacttgctca caagttcaaa ggaggtgctc tgaatacatt gctaagagtg       780
tcaggtctaa tcagcaatgg aggttatgta cttgcagtgg attgtgatat gtactgcaat       840
gatccaacct cagccaaaca agccatgtgt ttctttcttg atcctgaatc ctctaaatat       900
attgcatttg tccaattccc tcaaatgttt cacaacctta gcaaaaaaga catctatgat       960
aatcaatcta gaactgcttt taagacaatg tggcaaggga tggatggttt gagaggtcca      1020
ggtctttctg gcagtggcaa ttacttgagt agagctgctt tgttatttgg aagtccaaat      1080
caaaaagatg actatcttct agatgctgaa aactactatg gcaagtctag cacatacata      1140
gaatcactga gggaaatccg tggacaagaa gaacaaacta caaaaagaa taatctttca      1200 agagaacaaa ttttaagaga agctcaagta gtagcctctt gttcctatga gacaaacaca      1260
aaatggggaa cagaggtagg attctcatat gggatattac tagagagtac cataactggg      1320
tatctattgc attctagagg atggaaatca gcatatctat acccaaaaac accatgtttc      1380
ttaggctgtg ctcctactga catcaaggaa gggatgcttc aattggtcaa gtggttgtct      1440
gaactttgct tgcttgcagt ctctaaatac agccctttta cctatggatt ttcaacaatc      1500
tccactattc ataacttcac ttattgcttc atgtctattt cttccttata tgctattggc      1560
ttcatccttt atggcattgt acctcaagtt tgcttcctca aaggaatacc tgtctttcca      1620
aaggtcacag atccttggtt tctagtgttt gcaatactat atatagcgac acagattcaa      1680
catttgatag aggttatttc tggggatgga tcagtgtcaa tgtggtggga tgaacaaaga      1740
atttggattc tcaagtcagt tactagccta tttgcgatga tagaaggagt taagaaatgg      1800
```

```
ttgggattga acaagaaaaa attcaatttg tcaaataaag ctgttgacac agacaaagag    1860
aaaataaaaa aatatgaaca agggaggttt gattttcaag gtgcagcttt gtatatgtct    1920
ccaatggttg tgctgctgat agtcaacaca gtttgcttct ttggtggttt gtggagacta    1980
ttgagtacta gagattttga agatatgttt ggtcaactat tcctacttgg ttatgtaatg    2040
gctcttagtt atccaatatt tgagggcata ataactatga aaagcaagag tgggtaa      2097
```

<210> SEQ ID NO 42
<211> LENGTH: 698
<212> TYPE: PRT
<213> ORGANISM: Astragalus sinicus

<400> SEQUENCE: 42

```
Met Ala Glu Phe Ser Leu His Thr Glu Thr Val Gln Ser Trp Leu Pro
1               5                   10                  15

Leu Ser Arg Ala His Ile Ile Phe His Phe Ala Cys Val Leu Leu Leu
            20                  25                  30

Phe Tyr Tyr Arg Ile Thr Arg Phe Ile Pro Thr Leu Pro Ser Ile Leu
        35                  40                  45

Met Ile Ala Ala Glu Phe Ile Leu Ser Val Leu Trp Phe Phe Asn Gln
    50                  55                  60

Ala Tyr Arg Trp Arg Pro Val Ser Arg Ser Val Lys Thr Gln Asn Leu
65                  70                  75                  80

Pro Lys Asp Glu Asn Leu Pro Gly Leu Asp Ile Phe Val Cys Thr Ile
            85                  90                  95

Asp Pro Glu Lys Glu Pro Thr Val Glu Val Met Asn Thr Leu Val Ser
            100                 105                 110

Ala Ile Ser Met Asp Tyr Pro Pro His Lys Leu Ser Val Tyr Leu Ser
            115                 120                 125

Asp Asp Gly Ala Ala Pro Val Thr Phe Tyr Gly Ile Lys Glu Ala Ser
        130                 135                 140

Glu Phe Ala Lys Val Trp Val Pro Phe Cys Asn Lys Tyr Gly Val Lys
145                 150                 155                 160

Ser Arg Cys Pro Lys Val Phe Phe Ser Pro Leu Ala Glu Asp Glu Leu
                165                 170                 175

Val Pro Leu Arg Thr His Gln Phe Glu Asp Asp Lys Glu Asp Ile Lys
            180                 185                 190

Val Lys Tyr Asp Lys Met Gln Lys Asn Ile Glu Lys Phe Gly Ser Glu
        195                 200                 205

Pro Lys Asn Val Ser Met Val Thr Asp Arg Pro Ala Arg Ile Glu Ile
        210                 215                 220

Ile Ser Asp Glu Pro Glu Met Ala Arg Val Val Tyr Val Ser Arg Glu
225                 230                 235                 240

Arg Arg Pro Ser Leu Ala His Lys Phe Lys Gly Gly Ala Leu Asn Thr
                245                 250                 255

Leu Leu Arg Val Ser Gly Leu Ile Ser Asn Gly Gly Tyr Val Leu Ala
            260                 265                 270

Val Asp Cys Asp Met Tyr Cys Asn Asp Pro Thr Ser Ala Lys Gln Ala
        275                 280                 285

Met Cys Phe Phe Leu Asp Pro Glu Ser Ser Lys Tyr Ile Ala Phe Val
    290                 295                 300

Gln Phe Pro Gln Met Phe His Asn Leu Ser Lys Lys Asp Ile Tyr Asp
305                 310                 315                 320
```

```
Asn Gln Ser Arg Thr Ala Phe Lys Thr Met Trp Gln Gly Met Asp Gly
                325             330             335

Leu Arg Gly Pro Gly Leu Ser Gly Ser Gly Asn Tyr Leu Ser Arg Ala
            340             345             350

Ala Leu Leu Phe Gly Ser Pro Asn Gln Lys Asp Asp Tyr Leu Leu Asp
            355             360             365

Ala Glu Asn Tyr Tyr Gly Lys Ser Ser Thr Tyr Ile Glu Ser Leu Arg
        370             375             380

Glu Ile Arg Gly Gln Glu Gln Thr Asn Lys Lys Asn Asn Leu Ser
385             390             395             400

Arg Glu Gln Ile Leu Arg Glu Ala Gln Val Val Ala Ser Cys Ser Tyr
            405             410             415

Glu Thr Asn Thr Lys Trp Gly Thr Glu Val Gly Phe Ser Tyr Gly Ile
            420             425             430

Leu Leu Glu Ser Thr Ile Thr Gly Tyr Leu Leu His Ser Arg Gly Trp
            435             440             445

Lys Ser Ala Tyr Leu Tyr Pro Lys Thr Pro Cys Phe Leu Gly Cys Ala
        450             455             460

Pro Thr Asp Ile Lys Glu Gly Met Leu Gln Leu Val Lys Trp Leu Ser
465             470             475             480

Glu Leu Cys Leu Leu Ala Val Ser Lys Tyr Ser Pro Phe Thr Tyr Gly
            485             490             495

Phe Ser Thr Ile Ser Thr Ile His Asn Phe Thr Tyr Cys Phe Met Ser
            500             505             510

Ile Ser Ser Leu Tyr Ala Ile Gly Phe Ile Leu Tyr Gly Ile Val Pro
            515             520             525

Gln Val Cys Phe Leu Lys Gly Ile Pro Val Phe Pro Lys Val Thr Asp
        530             535             540

Pro Trp Phe Leu Val Phe Ala Ile Leu Tyr Ile Ala Thr Gln Ile Gln
545             550             555             560

His Leu Ile Glu Val Ile Ser Gly Asp Gly Ser Val Ser Met Trp Trp
            565             570             575

Asp Glu Gln Arg Ile Trp Ile Leu Lys Ser Val Thr Ser Leu Phe Ala
            580             585             590

Met Ile Glu Gly Val Lys Lys Trp Leu Gly Leu Asn Lys Lys Lys Phe
            595             600             605

Asn Leu Ser Asn Lys Ala Val Asp Thr Asp Lys Glu Lys Ile Lys Lys
        610             615             620

Tyr Glu Gln Gly Arg Phe Asp Phe Gln Gly Ala Ala Leu Tyr Met Ser
625             630             635             640

Pro Met Val Val Leu Leu Ile Val Asn Thr Val Cys Phe Phe Gly Gly
            645             650             655

Leu Trp Arg Leu Leu Ser Thr Arg Asp Phe Glu Asp Met Phe Gly Gln
            660             665             670

Leu Phe Leu Leu Gly Tyr Val Met Ala Leu Ser Tyr Pro Ile Phe Glu
            675             680             685

Gly Ile Ile Thr Met Lys Ser Lys Ser Gly
        690             695
```

```
<210> SEQ ID NO 43
<211> LENGTH: 37
<212> TYPE: DNA
<213> ORGANISM: Artificial
<220> FEATURE:
<223> OTHER INFORMATION: primer
```

<400> SEQUENCE: 43
aaaaagcagg ctatggcaac gttcacatac cacgtag                                    37

<210> SEQ ID NO 44
<211> LENGTH: 35
<212> TYPE: DNA
<213> ORGANISM: Artificial
<220> FEATURE:
<223> OTHER INFORMATION: primer

<400> SEQUENCE: 44
agaaagctgg gtctatccac tcttgctttt cattg                                      35

<210> SEQ ID NO 45
<211> LENGTH: 34
<212> TYPE: DNA
<213> ORGANISM: Artificial
<220> FEATURE:
<223> OTHER INFORMATION: primer

<400> SEQUENCE: 45
aaaaagcagg ctatggcgac cttccacaca gaaa                                       34

<210> SEQ ID NO 46
<211> LENGTH: 35
<212> TYPE: DNA
<213> ORGANISM: Artificial
<220> FEATURE:
<223> OTHER INFORMATION: primer

<400> SEQUENCE: 46
agaaagctgg gtctattgca ccttgctttt catgg                                      35

<210> SEQ ID NO 47
<211> LENGTH: 2100
<212> TYPE: DNA
<213> ORGANISM: Glycine max

<400> SEQUENCE: 47
atggcaacgt tcacatacca cgtagaaaca gttcaatcat tcttagccct aagcagactt          60
cacatactca tccacttagt ggcagtgttg tctctctgtt actaccgcat cacccacttc          120
ttcctccaac ctccaacagc gccatggctt ctcatgactg ctgcggagct tcttctctcg          180
ctgctctggt tcttcaacca agccttccgg tggcgaccgg tgtcgcggag cgtcatgact          240
gagaagcttc cgagtgagga gaagctgccg gggcttgaca tcttcgtgtg cacgctcgat          300
cccgagaagg agcccaccgt ggaggtcatt gacaccatca tctccgccgt gtccatggat          360
tacccctccg acaagctttc cgtctatctc tccgacgacg cggggtgcga cgtgactctc          420
tatgggatcc gagaggctgc tgagttcgcc aaggagtggg ttccgttctg taaaaagtat          480
ggggtgaagt caaggtgtcc caaagtcttc ttctctccct tggggatga ggatcaagag          540 actcttcggg acgatcaatt cagaacacag agagacctcg tcaaggctaa atacgagaaa          600
atgcagaaaa atatcgagaa atttggttca gaccctaaaa gtcgtcgtac tgtgagtgac          660
agacaacctc gtattgagat tataaatgac caaccgggaa tgccacttat tgtttatgtg          720
tctcgcgaaa gaaggccatc ccttcctcac aaattcaaag gaggagccgt caacacattg          780
ctcagagtct caggtttaat caataatgga ccttatgttc tagtaatgga ctgtgatatg          840
tatagcaatg atccaacctc tgccaaacaa gccatgtgct tctttcttga tcctgaaacg          900

-continued

```
tccaaatata ttgcatttgt tcaattccct caaatgtttc acaaccttag caaaaaggac    960
atttatgata gtcaagctag aactgctttt aagacaatgt ggcaaggcat ggatggacta   1020
agaggtccag gtctttctgg cagcggcaat tacttaagta gaagtgcttt actatttgga   1080
agtccaaacc aaaaagatga ctatctgcaa gatgcacaaa agtacttcgg caagtctacc   1140
gcctacattg aatcactgaa ggccatccgt ggacagaaaa gtagcaaaaa gaatatttca   1200
agagatgaaa tgttaagaga agctcaagta gtggcctctt gttcctacga aaataacaca   1260
aattggggca cagaggtggg attctcatat ggcatattac tagagagttc tattactggc   1320
tatattcttc acagcagagg atggaaatca gcatatcttt acccgaaaac accatgtttc   1380
ttaggttgtg ctcccactga catcaaggaa ggcatgcttc agttggttaa gtggttgtct   1440
gaacttttgt tgcttggtgt ctcctccaaa tacagcccat tcacttatgg attttcaaga   1500
atgtccatac ttcacacatt cacttattgc ttcatcacaa tgtcatccct ttatgctgtt   1560
gtcttcatcc tctacggcat tgtacctcaa gtatgcctcc tcaaaggaat ccctgtgttt   1620
ccaaaggcca cagacccttg gtttgccgtg tttgcatttg tgtatgtatc tactcagatt   1680
caacatttga ttgaggttct ctctggggat ggatctgtga caatgtggtg ggatgaacaa   1740
agaatttgga ttctgaagtc agttaccagc atatttgcaa ttatagatgg agtcaagaag   1800
tggttggggt tgagcaaggt gaaattcaac ttgtcaaaca aagcaattga caaagagaag   1860
ctcaagaaat atgagcaagg tagattcgat ttccaaggtg cagctgtgtt catggctcca   1920
ttggttctat tactcacagc caacattgtt agcttcttag ttggtatatg gagactatttt   1980 aatttcaatg tgaaggattt tgaagaaatg tttggtcaac ttttcctagt tacctatgta   2040
atggttctta gttatccact tcttgaggcc atggtaacaa tgaaaagcaa gagtggatag   2100
```

```
<210> SEQ ID NO 48
<211> LENGTH: 699
<212> TYPE: PRT
<213> ORGANISM: Glycine max

<400> SEQUENCE: 48

Met Ala Thr Phe Thr Tyr His Val Glu Thr Val Gln Ser Phe Leu Ala
1               5                   10                  15

Leu Ser Arg Leu His Ile Leu Ile His Leu Val Ala Val Leu Ser Leu
                20                  25                  30

Cys Tyr Tyr Arg Ile Thr His Phe Phe Leu Gln Pro Pro Thr Ala Pro
            35                  40                  45

Trp Leu Leu Met Thr Ala Ala Glu Leu Leu Leu Ser Leu Leu Trp Phe
        50                  55                  60

Phe Asn Gln Ala Phe Arg Trp Arg Pro Val Ser Arg Ser Val Met Thr
65                  70                  75                  80

Glu Lys Leu Pro Ser Glu Glu Lys Leu Pro Gly Leu Asp Ile Phe Val
                85                  90                  95

Cys Thr Leu Asp Pro Glu Lys Glu Pro Thr Val Glu Val Ile Asp Thr
            100                 105                 110

Ile Ile Ser Ala Val Ser Met Asp Tyr Pro Ser Asp Lys Leu Ser Val
        115                 120                 125

Tyr Leu Ser Asp Asp Gly Gly Cys Asp Val Thr Leu Tyr Gly Ile Arg
    130                 135                 140

Glu Ala Ala Glu Phe Ala Lys Glu Trp Val Pro Phe Cys Lys Lys Tyr
145                 150                 155                 160

Gly Val Lys Ser Arg Cys Pro Lys Val Phe Phe Ser Pro Phe Gly Asp
```

```
                         165                  170                  175
Glu Asp Gln Glu Thr Leu Arg Asp Asp Gln Phe Arg Thr Gln Arg Asp
            180                  185                  190

Leu Val Lys Ala Lys Tyr Glu Lys Met Gln Lys Asn Ile Glu Lys Phe
            195                  200                  205

Gly Ser Asp Pro Lys Ser Arg Thr Val Ser Asp Arg Gln Pro Arg
            210                  215                  220

Ile Glu Ile Ile Asn Asp Gln Pro Gly Met Pro Leu Ile Val Tyr Val
225                  230                  235                  240

Ser Arg Glu Arg Arg Pro Ser Leu Pro His Lys Phe Lys Gly Gly Ala
                245                  250                  255

Val Asn Thr Leu Leu Arg Val Ser Gly Leu Ile Asn Asn Gly Pro Tyr
                260                  265                  270

Val Leu Val Met Asp Cys Asp Met Tyr Ser Asn Asp Pro Thr Ser Ala
                275                  280                  285

Lys Gln Ala Met Cys Phe Phe Leu Asp Pro Glu Thr Ser Lys Tyr Ile
                290                  295                  300

Ala Phe Val Gln Phe Pro Gln Met Phe His Asn Leu Ser Lys Lys Asp
305                  310                  315                  320

Ile Tyr Asp Ser Gln Ala Arg Thr Ala Phe Lys Thr Met Trp Gln Gly
                325                  330                  335

Met Asp Gly Leu Arg Gly Pro Gly Leu Ser Gly Ser Gly Asn Tyr Leu
                340                  345                  350

Ser Arg Ser Ala Leu Leu Phe Gly Ser Pro Asn Gln Lys Asp Asp Tyr
                355                  360                  365

Leu Gln Asp Ala Gln Lys Tyr Phe Gly Lys Ser Thr Ala Tyr Ile Glu
                370                  375                  380

Ser Leu Lys Ala Ile Arg Gly Gln Lys Ser Ser Lys Lys Asn Ile Ser
385                  390                  395                  400

Arg Asp Glu Met Leu Arg Glu Ala Gln Val Val Ala Ser Cys Ser Tyr
                405                  410                  415

Glu Asn Asn Thr Asn Trp Gly Thr Glu Val Gly Phe Ser Tyr Gly Ile
                420                  425                  430

Leu Leu Glu Ser Ser Ile Thr Gly Tyr Ile Leu His Ser Arg Gly Trp
                435                  440                  445

Lys Ser Ala Tyr Leu Tyr Pro Lys Thr Pro Cys Phe Leu Gly Cys Ala
                450                  455                  460

Pro Thr Asp Ile Lys Glu Gly Met Leu Gln Leu Val Lys Trp Leu Ser
465                  470                  475                  480

Glu Leu Leu Leu Leu Gly Val Ser Ser Lys Tyr Ser Pro Phe Thr Tyr
                485                  490                  495

Gly Phe Ser Arg Met Ser Ile Leu His Thr Phe Thr Tyr Cys Phe Ile
                500                  505                  510

Thr Met Ser Ser Leu Tyr Ala Val Val Phe Ile Leu Tyr Gly Ile Val
                515                  520                  525

Pro Gln Val Cys Leu Leu Lys Gly Ile Pro Val Phe Pro Lys Ala Thr
                530                  535                  540

Asp Pro Trp Phe Ala Val Phe Ala Phe Val Tyr Val Ser Thr Gln Ile
545                  550                  555                  560

Gln His Leu Ile Glu Val Leu Ser Gly Asp Gly Ser Val Thr Met Trp
                565                  570                  575

Trp Asp Glu Gln Arg Ile Trp Ile Leu Lys Ser Val Thr Ser Ile Phe
                580                  585                  590
```

-continued

```
Ala Ile Ile Asp Gly Val Lys Lys Trp Leu Gly Leu Ser Lys Val Lys
        595                 600                 605

Phe Asn Leu Ser Asn Lys Ala Ile Asp Lys Glu Lys Leu Lys Lys Tyr
        610                 615                 620

Glu Gln Gly Arg Phe Asp Phe Gln Gly Ala Ala Val Phe Met Ala Pro
625                 630                 635                 640

Leu Val Leu Leu Leu Thr Ala Asn Ile Val Ser Phe Leu Val Gly Ile
                645                 650                 655

Trp Arg Leu Phe Asn Phe Asn Val Lys Asp Phe Glu Glu Met Phe Gly
                660                 665                 670

Gln Leu Phe Leu Val Thr Tyr Val Met Val Leu Ser Tyr Pro Leu Leu
        675                 680                 685

Glu Ala Met Val Thr Met Lys Ser Lys Ser Gly
        690                 695

<210> SEQ ID NO 49
<211> LENGTH: 2091
<212> TYPE: DNA
<213> ORGANISM: Glycine max

<400> SEQUENCE: 49
atggcgacct tccacacaga aaccgtgcaa tcagggttgg ccttgagcag actccacatc      60
ctattccact cggtggcact cttgtttctc tattactacc gcataagcca catcttactg     120
gaaccaagct ttgtatggat tttcatgacc atagcggagc ttatcttcgg cgagctctgg     180
ctcttcaaac aggcgttccg gtggcggccc gtgtcgaggg ccgtcatgcc ggagaagctg     240
ccgagcgacg gcaagcttcc ggcgctcgac atcttcgtct gcacggttga ccccgaaaag     300
gagccgacgg tgcaggtgat ggacaccgtc atctccgcca ttgccatgga ctacccctcc     360
aacaagctcg ccgtgtacct ttccgacgat ggcgggtgtc cggtgactct gtatgggatc     420
agagaggctt ctcggttcgc aaaggagtgg gttccgttct gcagaaagta tgggatcaat     480
tcacggtgcc ccaaggcctt cttctctccc atggggggagg atgaacgtga actgcttctt     540
cttcgcaacc atgaattctt ggcagagcaa gaacaactca aggctaaata caatataatg     600
caaaaaaata ttgacgaatt tggaagagac cctaaaaatc gttccattgt gtttgataga     660
ccagctcgca ttgagattat aaatgagcaa tccgaaatac cactggttgt ttatgtgtct     720
cgtgaaagaa ggccaaatgt tcctcataca tacaaagggg gagccctcaa cacattgctc     780
agagtctcag ggctattcag taacgggccc tatgtacttg tagttgattg tgatatgtat     840
tgcaatgatc catcatcagc taaacaagcc atgtgctttt ttcttgatcc tgaaacctcc     900
aaagatattg ctttttgtcca attccctcaa atgtttcaca accttagcat gaaagacatc     960
tacgatagtc aacataggca tgcttttaca acaatgtggc aaggaatgga tggactaaga    1020
ggtccaggtc tttctggtag tggcaattac ttaagtagaa gtgcattaat ctttccaagc    1080
ccatatgaaa aagacggcta tgaacataat gcccaaaaca aatttggcaa ctctaccatg    1140
tacattgaat cattaaaggc cattcaagga caacaaactt ataaaacgag catttcaaga    1200
aatgtgattt tacaggaagc acaagcagtg gcctcttgtt cctatgaaat agacacaaat    1260 tgggtaatg aggtaggatt ctcatatgtt atattactgg agagtacagt tactggctat    1320
cttcttcact gtagaggatg gagatcaact taccttttacc ccaaaagacc ttgtttcttg    1380
ggatgtgccc ccactgactt catggaaggc atgcttcagt tggtgaaatg gagttctgaa    1440
cttttcttgc taggaatatc caaatacagc cctttcactt atgggatttc aagaattcct    1500
```

-continued

```
attctgcaca actttacctt ttgctacttc acatctacat gtcaatatat tgttgcctta    1560
atagtatatg gcatcattcc tcaagtatgc ttcttgaaag gaactcctgt gtttcctaag    1620
gttacagaac catggtttgt agtttttgca atattatatg tatcctctca aagtcaacat    1680
ttgattgaag tcctttatgg tggtggctct ttgggaacat ggtgggatga acaaagaata    1740
tggattgtaa agtcaattgt tggaggcata tttggatcta tactagcaat caagaaacgt    1800
tttgggttaa acaaagcaaa attcatttta tcaaataaag ttgttgccaa agagaagttt    1860
gagaaatatg aacaaggtaa gttcgagttc gaaggtgcag ctttgttcat gtctccattg    1920
gttggattac tcatagtgaa tattctttgc ttctttggtg gttatggag actatttaat    1980 gtgaaagatt ttgaaaagat gtctggccaa ctttttctac ttggctatct ggcggcgctc    2040
agttatccca ttttgaggg gataataacc atgaaaagca aggtgcaata g           2091
```

<210> SEQ ID NO 50
<211> LENGTH: 696
<212> TYPE: PRT
<213> ORGANISM: Glycine max

<400> SEQUENCE: 50

```
Met Ala Thr Phe His Thr Glu Thr Val Gln Ser Gly Leu Ala Leu Ser
1               5                   10                  15

Arg Leu His Ile Leu Phe His Ser Val Ala Leu Leu Phe Leu Tyr Tyr
            20                  25                  30

Tyr Arg Ile Ser His Ile Leu Leu Glu Pro Ser Phe Val Trp Ile Phe
        35                  40                  45

Met Thr Ile Ala Glu Leu Ile Phe Gly Glu Leu Trp Leu Phe Lys Gln
    50                  55                  60

Ala Phe Arg Trp Arg Pro Val Ser Arg Ala Val Met Pro Glu Lys Leu
65                  70                  75                  80

Pro Ser Asp Gly Lys Leu Pro Ala Leu Asp Ile Phe Val Cys Thr Val
                85                  90                  95

Asp Pro Glu Lys Glu Pro Thr Val Gln Val Met Asp Thr Val Ile Ser
            100                 105                 110

Ala Ile Ala Met Asp Tyr Pro Ser Asn Lys Leu Ala Val Tyr Leu Ser
        115                 120                 125

Asp Asp Gly Gly Cys Pro Val Thr Leu Tyr Gly Ile Arg Glu Ala Ser
    130                 135                 140

Arg Phe Ala Lys Glu Trp Val Pro Phe Cys Arg Lys Tyr Gly Ile Asn
145                 150                 155                 160

Ser Arg Cys Pro Lys Ala Phe Phe Ser Pro Met Gly Glu Asp Glu Arg
                165                 170                 175

Glu Leu Leu Leu Leu Arg Asn His Glu Phe Leu Ala Glu Gln Glu Gln
            180                 185                 190

Leu Lys Ala Lys Tyr Asn Ile Met Gln Lys Asn Ile Asp Glu Phe Gly
        195                 200                 205

Arg Asp Pro Lys Asn Arg Ser Ile Val Phe Asp Arg Pro Ala Arg Ile
    210                 215                 220

Glu Ile Ile Asn Glu Gln Ser Glu Ile Pro Leu Val Val Tyr Val Ser
225                 230                 235                 240

Arg Glu Arg Arg Pro Asn Val Pro His Thr Tyr Lys Gly Gly Ala Leu
                245                 250                 255

Asn Thr Leu Leu Arg Val Ser Gly Leu Phe Ser Asn Gly Pro Tyr Val
            260                 265                 270
```

```
Leu Val Val Asp Cys Asp Met Tyr Cys Asn Asp Pro Ser Ser Ala Lys
        275             280             285

Gln Ala Met Cys Phe Phe Leu Asp Pro Glu Thr Ser Lys Asp Ile Ala
    290             295             300

Phe Val Gln Phe Pro Gln Met Phe His Asn Leu Ser Met Lys Asp Ile
305             310             315             320

Tyr Asp Ser Gln His Arg His Ala Phe Thr Thr Met Trp Gln Gly Met
            325             330             335

Asp Gly Leu Arg Gly Pro Gly Leu Ser Gly Ser Gly Asn Tyr Leu Ser
            340             345             350

Arg Ser Ala Leu Ile Phe Pro Ser Pro Tyr Glu Lys Asp Gly Tyr Glu
            355             360             365

His Asn Ala Gln Asn Lys Phe Gly Asn Ser Thr Met Tyr Ile Glu Ser
    370             375             380

Leu Lys Ala Ile Gln Gly Gln Gln Thr Tyr Lys Thr Ser Ile Ser Arg
385             390             395             400

Asn Val Ile Leu Gln Glu Ala Gln Ala Val Ala Ser Cys Ser Tyr Glu
            405             410             415

Ile Asp Thr Asn Trp Gly Asn Glu Val Gly Phe Ser Tyr Val Ile Leu
            420             425             430

Leu Glu Ser Thr Val Thr Gly Tyr Leu Leu His Cys Arg Gly Trp Arg
        435             440             445

Ser Thr Tyr Leu Tyr Pro Lys Arg Pro Cys Phe Leu Gly Cys Ala Pro
    450             455             460

Thr Asp Phe Met Glu Gly Met Leu Gln Leu Val Lys Trp Ser Ser Glu
465             470             475             480

Leu Phe Leu Leu Gly Ile Ser Lys Tyr Ser Pro Phe Thr Tyr Gly Ile
            485             490             495

Ser Arg Ile Pro Ile Leu His Asn Phe Thr Phe Cys Tyr Phe Thr Ser
            500             505             510

Thr Cys Gln Tyr Ile Val Ala Leu Ile Val Tyr Gly Ile Ile Pro Gln
        515             520             525

Val Cys Phe Leu Lys Gly Thr Pro Val Phe Pro Lys Val Thr Glu Pro
    530             535             540

Trp Phe Val Val Phe Ala Ile Leu Tyr Val Ser Ser Gln Ser Gln His
545             550             555             560

Leu Ile Glu Val Leu Tyr Gly Gly Gly Ser Leu Gly Thr Trp Trp Asp
            565             570             575

Glu Gln Arg Ile Trp Ile Val Lys Ser Ile Val Gly Gly Ile Phe Gly
            580             585             590

Ser Ile Leu Ala Ile Lys Lys Arg Phe Gly Leu Asn Lys Ala Lys Phe
            595             600             605

Ile Leu Ser Asn Lys Val Val Ala Lys Glu Lys Phe Glu Lys Tyr Glu
    610             615             620

Gln Gly Lys Phe Glu Phe Glu Gly Ala Ala Leu Phe Met Ser Pro Leu
625             630             635             640

Val Gly Leu Leu Ile Val Asn Ile Leu Cys Phe Phe Gly Gly Leu Trp
            645             650             655

Arg Leu Phe Asn Val Lys Asp Phe Glu Lys Met Ser Gly Gln Leu Phe
            660             665             670

Leu Leu Gly Tyr Leu Ala Ala Leu Ser Tyr Pro Ile Phe Glu Gly Ile
            675             680             685
```

-continued

```
Ile Thr Met Lys Ser Lys Val Gln
    690                 695

<210> SEQ ID NO 51
<211> LENGTH: 12
<212> TYPE: DNA
<213> ORGANISM: Artificial
<220> FEATURE:
<223> OTHER INFORMATION: synthetic; 12 nucleotides added to the 5'
      terminal of the forward primer

<400> SEQUENCE: 51 aaaaa gcagg ct                                                      12

<210> SEQ ID NO 52
<211> LENGTH: 12
<212> TYPE: DNA
<213> ORGANISM: Artificial
<220> FEATURE:
<223> OTHER INFORMATION: synthetic; 12 nucleotides added to the 5'
      terminal of the reverse primer

<400> SEQUENCE: 52
agaaagctgg gt                                                       12
```